(12) United States Patent
Auberger et al.

(10) Patent No.: US 11,478,366 B2
(45) Date of Patent: Oct. 25, 2022

(54) ACTUATOR-DAMPER UNIT

(71) Applicant: OTTO BOCK HEALTHCARE PRODUCTS GMBH, Vienna (AT)

(72) Inventors: Roland Auberger, Vienna (AT); Harald Sima, Herzogenburg (AT); Martin Seyr, Vienna (AT)

(73) Assignee: OTTO BOCK HEALTHCARE PRODUCTS GMBH, Vienna (AT)

(*) Notice: Subject to any disclaimer, the term of this patent is extended or adjusted under 35 U.S.C. 154(b) by 0 days.

(21) Appl. No.: 15/726,784

(22) Filed: Oct. 6, 2017

(65) Prior Publication Data

US 2018/0098864 A1    Apr. 12, 2018

(30) Foreign Application Priority Data

Oct. 6, 2016   (DE) .......................... 102016118999.5

(51) Int. Cl.
| | |
|---|---|
| *A61F 2/64* | (2006.01) |
| *A61H 3/00* | (2006.01) |
| *A61F 5/01* | (2006.01) |
| *A61F 2/74* | (2006.01) |
| *A61F 2/70* | (2006.01) |
| *B25J 9/00* | (2006.01) |

(Continued)

(52) U.S. Cl.
CPC .................. *A61F 2/70* (2013.01); *A61F 2/64* (2013.01); *A61H 1/0274* (2013.01); *A61H 3/00* (2013.01); *B25J 9/0006* (2013.01); *A61F 2/60* (2013.01); *A61F 2/74* (2021.08); *A61F 2/748* (2021.08); *A61F 2002/503* (2013.01); *A61F 2002/5006* (2013.01); *A61F 2002/5038* (2013.01); *A61F 2002/5073* (2013.01); *A61F 2002/7635* (2013.01); *A61F 2002/7645* (2013.01); *A61F 2005/0155* (2013.01); *A61F 2005/0169* (2013.01)

(58) Field of Classification Search
CPC .......... A61F 2002/485; A61F 2002/745; A61F 2/484; A61F 2/74; A61F 2/748
See application file for complete search history.

(56) References Cited

U.S. PATENT DOCUMENTS

| | | |
|---|---|---|
| 2,480,856 A | 9/1949 | Henschke et al. |
| 3,605,960 A | 9/1971 | Singer |

(Continued)

FOREIGN PATENT DOCUMENTS

| | | |
|---|---|---|
| DE | 9405545 | 3/1994 |
| DE | 20306821 U1 | 6/2003 |

(Continued)

*Primary Examiner* — David H Willse
(74) *Attorney, Agent, or Firm* — Holland & Hart LLP

(57) ABSTRACT

An actuator-damper unit for use in orthotic or prosthetic devices. The actuator-damper unit includes a housing which may be fastened on the orthotic or prosthetic device and in which a cylinder is formed. A first piston is displaceably mounted in the cylinder and is coupled to a piston rod. The piston rod is disposed, via a first end, on the first piston and may be coupled, via a second end, to the orthotic or prosthetic device. The first piston separates two fluid chambers in the cylinder from each other and forms a piston-cylinder unit, wherein at least one further piston is coupled to the first piston in order to form at least one further, variable-volume fluid chamber.

26 Claims, 41 Drawing Sheets

(51) Int. Cl.
  *A61H 1/02* (2006.01)
  *A61F 2/50* (2006.01)
  *A61F 2/60* (2006.01)
  *A61F 2/76* (2006.01)

(56) References Cited

U.S. PATENT DOCUMENTS

| | | |
|---|---|---|
| 5,376,138 A | 12/1994 | Bouchard et al. |
| 5,728,174 A | 3/1998 | Fitzlaff |
| 5,948,021 A | 9/1999 | Radcliffe |
| 6,106,560 A | 8/2000 | Boender |
| 6,997,959 B2 | 2/2006 | Chen et al. |
| 8,928,161 B2 | 1/2015 | Loverich et al. |
| 8,974,543 B2 | 3/2015 | Balboni et al. |
| 2014/0128993 A1 | 5/2014 | Shen |
| 2015/0164660 A1 | 6/2015 | Will et al. |
| 2015/0182354 A1* | 7/2015 | Bonnet ............... A61F 2/64 623/26 |
| 2015/0202057 A1* | 7/2015 | Zahedi ............... A61F 2/64 623/26 |

FOREIGN PATENT DOCUMENTS

| | | | | |
|---|---|---|---|---|
| DE | 10 2008 045 113 A1 * | 3/2010 | ............ | A61F 2/68 |
| DE | 102008045113 A1 | 3/2010 | | |
| DE | 102012013141 A1 | 5/2014 | | |
| JP | H 11-19105 A * | 1/1999 | ............ | A61F 2/68 |
| JP | 2015521506 A | 7/2015 | | |
| SU | 1577785 A1 * | 7/1990 | ............ | A61F 2/74 |
| WO | 2014005709 A2 | 9/2014 | | |

\* cited by examiner

ACTUATOR-DAMPER UNIT

TECHNICAL FIELD

The present disclosure relates to an actuator-damper unit for use in orthotic or prosthetic devices. The actuator-damper unit comprises a housing which may be fastened on the prosthetic device. A cylinder is formed in the housing, in which a first piston is displaceably mounted. The first piston is coupled to a piston rod which is disposed, by a first end, on the first piston and may be coupled, on a second end, to the orthotic or prosthetic device. The first piston separates two fluid chambers formed in the cylinder and forms a piston-cylinder unit. Orthotic or prosthetic devices are understood to mean, in particular, orthoses, prostheses, and exoskeletons. The actuator-damper unit may also be utilized in robotics.

BACKGROUND

In orthotic and prosthetic devices, two components may be displaced relative to each other. For example, an upper part and a lower part are pivoted relative to each other about a joint axis in an orthotic joint or a prosthetic joint. In addition, longitudinally displaceable relative movements can occur between two orthotic or prosthetic components. It may be necessary to dampen the relative movements. Hydraulic and/or pneumatic dampers may dampen an extension or flexion of a rotational joint or a displacement movement in one direction or the other. The dampers may be adjustable to provide changing resistances to the relative movement over the cycle of a user's movement based on sensor data or established control curves. Valves or throttles, which in some embodiments, may be adjustable, may be provided in flow channels.

Actuators, which may be designed as electric motors, for example, may assist a movement of the components of the orthotic or prosthetic device. Hydraulic or pneumatic drives may also be provided. Energy accumulators may store kinetic energy. This stored energy, which may be obtained, for example, by braking a flexion movement, may be fed back to the system over a later cycle of the movement cycle or at another point in time. The orthotic or prosthetic device is driven via the energy return. Energy may be fed in a movement-assisting manner via an actuator.

DE 10 2012 013 141 A1 describes an orthotic or prosthetic joint device comprising an upper part and a lower part pivotably disposed on the upper part. At least one hydraulic unit may be positioned or interposed between the upper part and the lower part. The joint device comprises a piston, which is movable in a housing. The housing includes an extension chamber and a flexion chamber and is coupled to the upper part or the lower part. Pressure may be applied to the piston via a pressure supply device, wherein the pressure supply device comprises at least one pressure accumulator coupled to either the extension chamber or to the flexion chamber via a switching device. The pressure accumulator may be coupled to a pump to fill the pressure accumulator via the pump. The disadvantage of such a design is the relatively large amount of space required by the external pressure accumulator.

One of the problems addressed by the present disclosure is therefore that of providing an actuator-damper unit which may be utilized in variable ways and is robust and compact.

Advantageous embodiments and refinements of the present disclosure are disclosed in the description and the figures.

SUMMARY

An actuator-damper unit for use in orthotic or prosthetic devices includes a housing which may be fastened on the orthotic or prosthetic device. A cylinder is formed in the housing. A first piston is displaceably mounted on the housing and is coupled to a piston rod. The piston rod is disposed, via a first end, on the first piston and may be coupled, via a second end, to the orthotic or prosthetic device. The first piston separates the cylinder into two fluid chambers forming a piston-cylinder unit. At least one further piston is coupled to the first piston forming at least one further variable-volume fluid chamber. The coupling may be a mechanical or fluid coupling, such as a hydraulic coupling. The second piston is displaceable in the cylinder and forms at least one further variable-volume fluid chamber. While the second piston is displaceable within the cylinder, a further third fluid chamber is formed for storing mechanical energy. So, in addition to motion damping controlled by throttle valves during, for example, a controlled release of the stored energy at any point in time, the pure damper function may be supplemented with an actuator function. Additional embodiments for altering the damping properties are introduced when the third fluid chamber has a variable fluid volume.

These damping properties may be combined with the option of a motion support system. In embodiments involving prosthetics or orthotics, particularly prostheses or orthoses of lower extremities, the storage of excess energy occurs during phases of a movement cycle in which there is excess energy, e.g., when a movement must be braked or stopped. The energy is stored during these phases and is released again at an appropriate point in time to minimize the required active power that the user applies to carry out the motion. The actuator-damper unit is disposed on the prosthetic or orthotic device such that two components of the orthotic or prosthetic device, which are displaceable relative to each other, are coupled to each other via the actuator-damper unit. In this case, a part or a component of the device is coupled to the piston rod, while the housing or a component disposed on or in the housing, which is not the first piston or the piston rod, is attached to the other component of the device or is coupled thereto. The coupling between the piston rod and the device may be indirect, with an intermediate element disposed between the piston rod and the device. The intermediate element may comprise a force sensor system or a pressure sensor system. Attachment to the device allows energy to feed from the orthotic or prosthetic device into the actuator-damper unit and to remove energy therefrom.

Energy may be stored in the variable-volume fluid chamber, for example, by the second piston being coupled to the first piston through a compressible energy accumulator. The compressible energy accumulator is preferably disposed in the variable-volume fluid chamber and may be a spring, an elastomeric element, and/or a compressible fluid volume, for example, a gas cushion or gas volume. The energy accumulator may be a tension element and/or a compression element. The storage of the energy may take place by a change of volume in the chamber in which the energy accumulator is disposed, and by the subsequent fixation or retention of the volume by closing the access opening. To release energy from the energy accumulator, the fluid chamber is opened, the accumulator expands, and the volume of the fluid chamber changes. If a spring is tensile loaded, for example, it attempts to reduce the volume of the fluid chamber, which is unsuccessful when a valve is closed. If the valve is opened, the spring contracts, the volume of the chamber is reduced, and the pistons move in the corresponding direction. In some embodiments, the compressible energy accumulator may couple to an outside the cylinder, for example, in a compensating container, to which pressure may be applied, or a pressure accumulator which is spring-loaded. If an energy accumulator is not present or is not activated in the actuator-damper unit, the actuator-damper unit may act as a pure damper having an increased variability of the damper properties due to the further, variable-volume fluid chamber. The actuator-damper unit can therefore also be utilized as a pure damper unit.

Every fluid chamber may have at least one access opening and may be connected to at least one other fluid chamber through fluid lines and/or valves. The fluid lines provide a volume compensation of the variable-volume chambers, for example, an extension chamber or a flexion chamber, as well as the additional, variable-volume fluid chamber. Due to the formation, for example, of an overflow channel from a flexion chamber into an extension chamber in the piston-cylinder unit, the fluid may flow into the particular expanding fluid chamber. During a flexion movement, the volume of the flexion chamber decreases and, correspondingly, the volume of the extension chamber increases, and so the volume pressed out of the flexion chamber may flow, entirely or partially, into the extension chamber.

At least one valve may be assigned to each fluid chamber, allowing the fluid flow into and out of the fluid chamber to be adjusted. The valves may completely block the access or connect fluid lines to each other, and/or disconnect the fluid lines from each other. Different combinations of overflow lines and interconnections of fluid chambers are possible. The valves may be, for example, switching valves, control valves, or non-return valves, to provide the desired fluid flows and resistances within the fluid flows. The flow cross-section may be changed, either in discrete steps or continuously, by means of control valves or regulating valves. Non-return valves block a fluid line in one direction of flow and release it in the opposite direction of flow without the need for any further switching or control actions. Different fluid lines may be interconnected with each other via a switching valve (e.g., a 3-way valve) to provide the level of dampening or energy supply required for the particular movement, and/or to connect chambers to each other or to further devices, and/or to separate chambers from said further devices. Non-return valves may ensure the energy accumulator is loaded only at a sufficient working pressure which may be higher than the storage pressure. A non-return valve may enable implementation of a "loading line," which may limit or prevent an unintended release at insufficient working pressure. If the accumulator volume is connected via two separate lines, each of which is provided with oppositely oriented non-return valves, defined lines for loading and release may be obtained. A pure spring behavior may be implemented by connecting the storage volume to a line without non-return valves. The viscosity of the fluid may change the damping, for example, with the aid of magnetorheological fluids and adjustable magnetic fields.

At least one compensating volume may be coupled to at least one of the fluid chambers to compensate for, in particular, fluctuations in the volume of the third fluid chamber or of the further fluid chamber. The compensating volume may be disposed outside the cylinder. Alternatively, the compensating volume may be integrated in the cylinder. Differences in volumes, for example, due to the piston rod or temperature-induced expansions of the fluid, may also be compensated for by the compensating volume. The compensating volume may be coupled to at least one of the fluid chambers through at least one valve. The compensating volume may be a pressure accumulator. For example, the pressure accumulator may comprise a compressible medium, a spring, or another mechanical energy accumulator, with respect to which the compensating volume must be filled with the fluid. The pressure accumulator may expand to release the fluid. A preliminary pressure in the system may also be implemented by the pressure accumulator. This may reduce a cavitation tendency and may reduce noise.

As an additional component, a pump for increasing the fluid pressure may be assigned to the actuator-damper unit. If power is lost, the pump may store additional energy in the fluid system. The pump may be coupled to an external energy accumulator, in particular a rechargeable battery or a battery, wherein the pump is then driven by an electric motor. The accumulator may be loaded by the pump output, so that the required energy may be obtained from the accumulator. If the energy level in the accumulator is not high enough, an increase in the level is effectuated by the pump. The joint may also be actively moved directly by the pump, without an interconnection of the accumulator. The pump may be advantageously controlled using the control device for loading the accumulator and for the direct movement of the pump.

The pump may not be directly assigned or operably coupled to the first piston-cylinder unit, but rather to a second piston-cylinder unit, which may be unidirectionally connected to the first piston-cylinder unit. The second piston-cylinder unit may be disposed in parallel to the first piston-cylinder unit, at the same fastening points as the first piston-cylinder unit, if necessary, to provide a parallel connection of the two piston-cylinder units. Alternatively, the second piston-cylinder unit may be connected in series to the first piston-cylinder unit, which may increase the length of the actuator-damper unit. The second piston-cylinder unit may facilitate delivery of the force applied via the pump in addition to the energy stored in the first piston-cylinder unit.

The fluid may be a hydraulic fluid, and so a hydraulic actuator-damper is present. Pneumatic components may be provided, for example, for use with a compressible pressure medium and an energy accumulator.

A control device may be connected to the valves for the adjustment or switching thereof, to allow for an electrically or electronically controlled actuation of the valves and the control of the fluid flow. The control device may be coupled to sensors, for example, angle sensors, force sensors, piston position sensors, and/or pressure sensors, which transmit data to the actuator-damper unit and/or the orthotic or prosthetic device of the control device related to the state and/or movement of the device. Based on sensor data, such as sensor data regarding the movement state of the orthotic or prosthetic device on the patient gather using, for example, gyroscopes and/or acceleration sensors, the control device can then carry out a switching of the valves and a regulation of the particular flow-through quantities and reach a decision regarding whether and how stored energy should be released, whether and how a pure damper operation should be carried out, and/or whether and how energy should be stored. The control device functions electronically (e.g., processes electrical or optical signals, or any other type of signals) by, for example, a data processing device, a processor, or a computer. The control unit initiates the adjustment of valves or magnetic fields in order to change resistances or open or close flow paths.

In some embodiments, two further pistons are disposed in the cylinder, which may form two further, variable-volume fluid chambers. As a result, a total of four fluid chambers may be created, whereby both the accumulation as well as the release can take place in both directions of travel. A compact design may include two further pistons disposed on opposite sides of the first piston. In some embodiments, the two further pistons are disposed in cylinders which are fluidically decoupled from the first cylinder but which are mechanically connected to each other. For example, a first further piston may be elastically mounted in a separate chamber of the first cylinder, forming two fluid chambers, while the piston rod of the first piston is disposed on a housing of a second, separate, displaceable housing in which a third piston is elastically mounted, which, in turn, is directly mounted on the device using a piston rod. Therefore, three piston-cylinder units are connected in series and form six fluid chambers, wherein energy storage can take place in two fluid chambers. The three piston-cylinder units may accumulate and release energy in both directions of travel.

BRIEF DESCRIPTION OF DRAWINGS

Illustrative embodiments of the present disclosure are explained in more detailed below with reference to the attached figures, in which.

DETAILED DESCRIPTION

Figure 1:
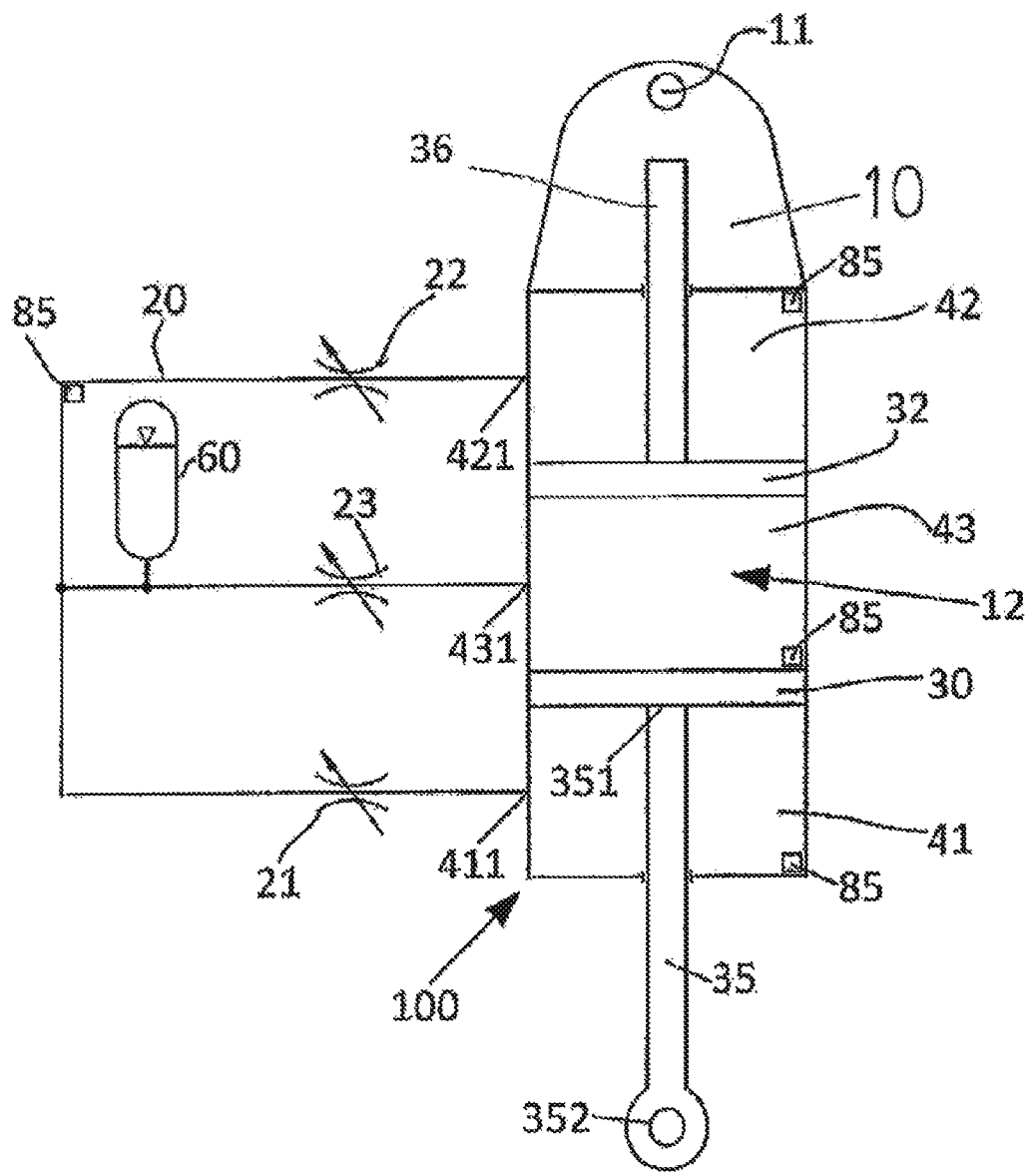
FIG. 1 shows a schematic representation of an exemplary embodiment of an actuator-damper unit.

FIG. 1 is a schematic representation showing an actuator-damper unit 100 for use in a prosthetic or orthotic device, for example, in a prosthesis or orthosis. The actuator-damper unit 100, which is referred to in the following as an "AD unit", comprises a cylinder 12 formed within a housing 10. In one embodiment, the cylinder 12 has a circular cross-section and a first piston 30 is displaceably mounted along an inner wall of the cylinder 12. In some embodiments, the shape of the piston 30 may comprise a non-circular cross-section. A piston rod 35 may be disposed on the first piston 30 and may be a first end 351 of the piston rod 35 may connect to the first piston 30. The second end 352 of the piston rod 35, opposite the first end 351, may be attached to the prosthetic or orthotic device. The housing 10 may comprise a fastening device 11, which can attach the housing 10 to another prosthesis component or orthosis component. If the two orthosis or prosthesis components are displaceable relative to each other, the piston 30 may move within the cylinder 12 and change a volume of a first fluid chamber 41. As the volume of the first fluid chamber 41 is reduced, the opposite volume of the cylinder 12, which is subdivided by the first piston 30, is increased. A second piston 32 may be displaceably disposed in the second fluid chamber 42a long a longitudinal axis of the cylinder 12. The second piston 32 may subdivide the second fluid chamber creating a third variable-volume fluid chamber 43 between the two pistons 30, 32. A sensor 85 in the form of a pressure sensor may be disposed within each fluid chamber 41, 42, 43 to detect a pressure present in the corresponding fluid chamber 41, 42, 43. In another embodiment, additional or alternative sensors may be provided. Sensor data may be transmitted to a control device described in greater detail further below.

A second rod 36 may be disposed on the second piston 32 and extend out of the housing 10. In some embodiments, a compensating volume 60 may be present if the second rod 36 has the same cross-section as the piston rod 35. A compensating volume 60 may accept fluid transported when a pure displacement of the two pistons 30, 32 occurs without a change in volume of the middle fluid chamber 43. In some embodiments, a compensating volume 60 may be necessary when a single piston rod 35 is present and the fluid, which may be a hydraulic fluid, is essentially incompressible. If the second rod 36 is dispensed with, the volume displaced by the piston rod must be compensated for, e.g., by means of a compensating volume 60.

Each of the fluid chambers 41, 42, 43 may include an access opening 411, 421, 431, which may allow the hydraulic fluid to flow in and out of a corresponding fluid chamber 41, 42, 43. The access openings 411, 421, 431 may be interconnected by various fluid lines 20. A switching or control valve 21, 22, 23 may be disposed in the fluid line 20 upstream of each access opening 411, 421, 431. The valves 21, 22, 23 may adjust a flow cross-section of the corresponding fluid line 20 and which may correspond to a hydraulic resistance.

A compressible medium or a spring may be disposed within the variable-volume fluid chamber 43. The volume of the third fluid chamber 43 may then be reduced when valve 22 is closed and valve 23 is at least partially opened. As a result, the compressible medium may be compressed and store energy. A compensating volume 60 may correspond to the AD unit 100 due to the change in volume within the fluid chamber 43. A volume compensation may take place when one of, for example, a leakage, a retracting piston rod, temperature fluctuations, or the like occur. The pressure in the compensating volume 60 may be measured with an optional pressure sensor 85. The pressure sensor 85 may provide information regarding the reduction of the preliminary pressure due to fluid losses. If the valve 23 is closed, the third fluid chamber 43 may behave quasi-rigidly, so a damper hydraulic system may be provided. The damper hydraulic system may comprise a flexion chamber 41 and an extension chamber 42. As soon as the valve 23 is opened, the compressed volume may expand or the spring or the elastic element and the piston 30 may be pressed outwardly, opposite a compression direction, whereby a corresponding movement is effectuated or assisted in the orthotic or prosthetic device. Alternatively, the piston 30 might be pulled towards the other piston 32.

Figure 2:
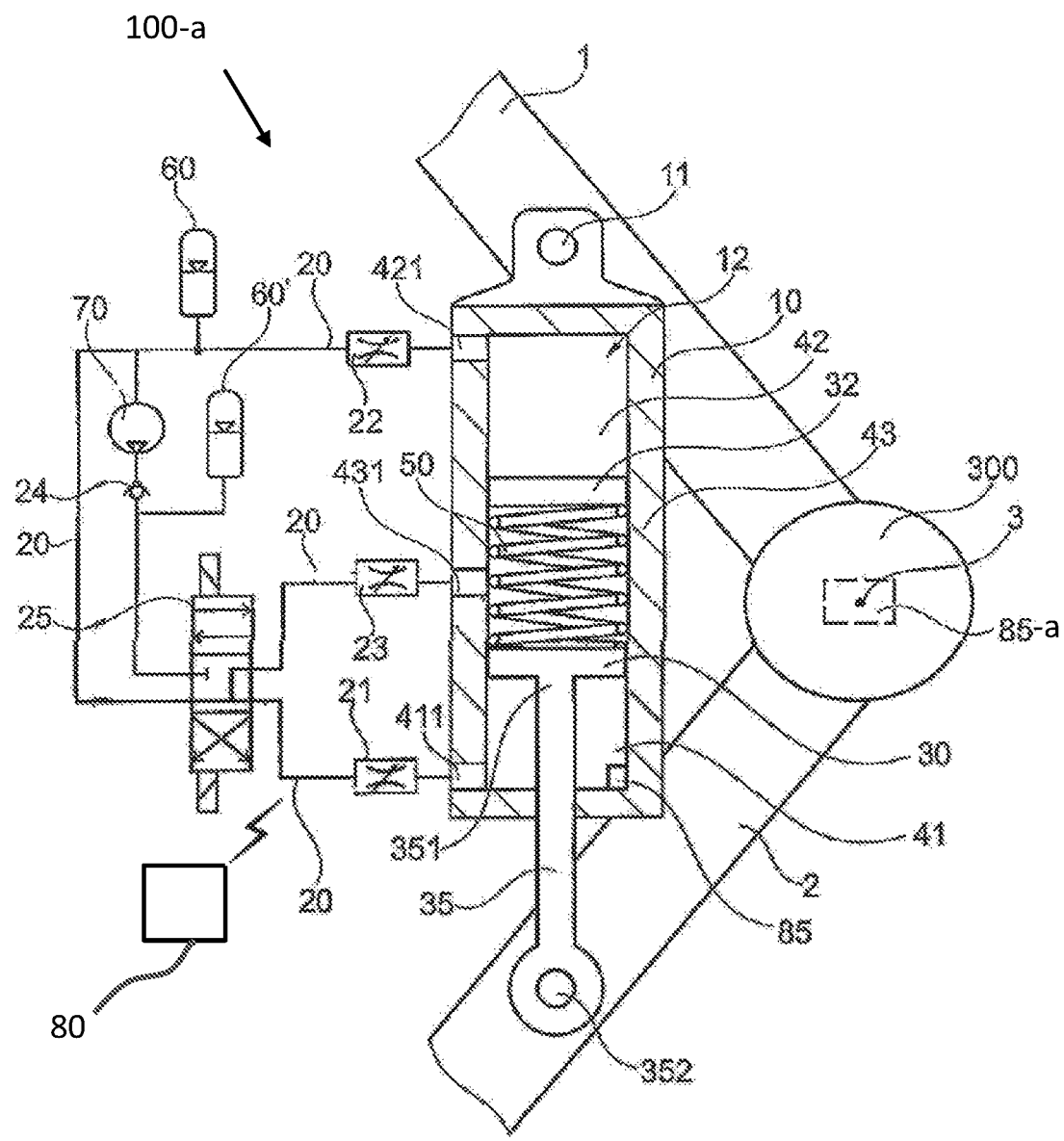
FIG. 2 shows a further embodiment of the exemplary actuator-damper unit in FIG. 1 in an installed state.

Another embodiment is shown in FIG. 2, in which the AD unit 100-a is fastened by the housing 10 to an upper part 1 of an orthotic or prosthetic joint device via a fastening element 11. The fastening element 11 may comprise, for example, a bolt, fastener, plug, or other coupling device. A lower part 2 is rotatably mounted on the upper part 1 about a pivot axis 3 formed in a joint device 300. The joint device 300 may connect the upper part 1 to the lower part 2 and may be a simple pivot axis 3 or a polycentric mechanism. The piston rod 35 of the piston 30 may be pivotably connected to the lower part 2 by the second end 352. The joint device 300 may extend if the piston 30 is moved downward. If the piston 30 is moved upward, the joint angle between the upper and lower part 1, 2 may become smaller causing the joint device 300 to flex. A sensor 85-a may be disposed around the joint axis 3 for detecting position data, e.g., an angle, between the upper part 1 and the lower part 2. The position data may be transmitted to a control device 80. For a polycentric joint, a sensor-based angle measurement may also be detected. In some embodiments, multiple sensors 85-a may detect sensor-based angle measurements. In some embodiments, the sensors 85 may comprise pressure sensors and may deliver control signals to the control device 80 to control a valve block which may be part of the control device 80. Alternatively or additionally, the position of the piston 30 and the force applied by the AD unit may also be measured and transmitted to the control device 80.

As shown in FIG. 2, three access openings 411, 421, 431, are proximate to a corresponding control valve 21, 22, 23. The control valve 21, 22, 23 may be adjusted based at least in part on control signals from the control device 80. For example, the flow cross-section of the fluid line 20 may be increased or decreased, or the flow may be blocked. In the embodiment shown, the compensating volume 60 may comprise a preliminary pressure. In addition, a pump 70 may provide additional energy and may be coupled to a non-return valve 24, in conjunction with a compensating volume 60 or an accumulator 50 and a 3-way valve 25, to the hydraulic system of the AD unit 100-a. The compensation volume 60' on the high pressure side of the pump 70 has a different function than the compensation volume 60 on the low pressure side and acts as a buffer to reduce pressure peaks. Additional potential or kinetic energy may be introduced into the system by the pump 70. The pump 70 may provide additional kinetic energy if the energy stored within the variable-volume fluid chamber 43 is insufficient for initiating or executing the desired movement. The pump 70 may supplement stored mechanical energy. The pump 70 may also introduce energy into the hydraulic system, and so an energy accumulator 50 may be loaded. The energy accumulator 50 may comprise, a spiral coiled spring, an elastic element comprising either a compression element or a tension element. The energy accumulator 50 is not limited to the elastic element As shown in FIG. 2, the pump 70 is decoupled when the 3-way valve 25 is in the central switching position. If the valve 25 is switched downward, the pump 70 connects to the third, further fluid chamber 43, and a build-up of pressure within the chamber 43 forms when the upstream control valve 23 is open. The two other fluid chambers 41, 42 may then be interconnected by the fluid line 20 and the valves 21, 22. If a volume increase occurs within the chamber 43 due to the pressure applied via the pump 70, this volume increase may be absorbed by volume changes of the other chambers 41 or 42 or by volume changes of the compensating volume 60.

If the 3-way valve is displaced upward, the pump 70 may apply hydraulic pressure to the first fluid chamber 41, which may reduce a volume of the third fluid chamber 43. As the volume of the third fluid chamber 43 is reduced, the spring 50, as the energy accumulator, may compress when the valve 23 is open.

If the third valve 23 of the fluid chamber 43 is blocked and the two other valves 23, 22 of the fluid chambers 41, 42 at the ends are open, the AD unit 100-a may move freely. The energy in the accumulator 50 may dissipate when the valve 21 of the first fluid chamber 41 is blocked and the two other valves 22, 23 are open. Energy may be stored or released when the valve 22 of the upper fluid chamber 42 is closed and the two other valves 21, 23 are open. If the upper valve 22 is open and the valve 23 of the central fluid chamber 43 is throttled to a greater extent than the valve 21 of the first fluid chamber 41, energy is released in a direction of travel opposite the storage direction.

Figure 3:
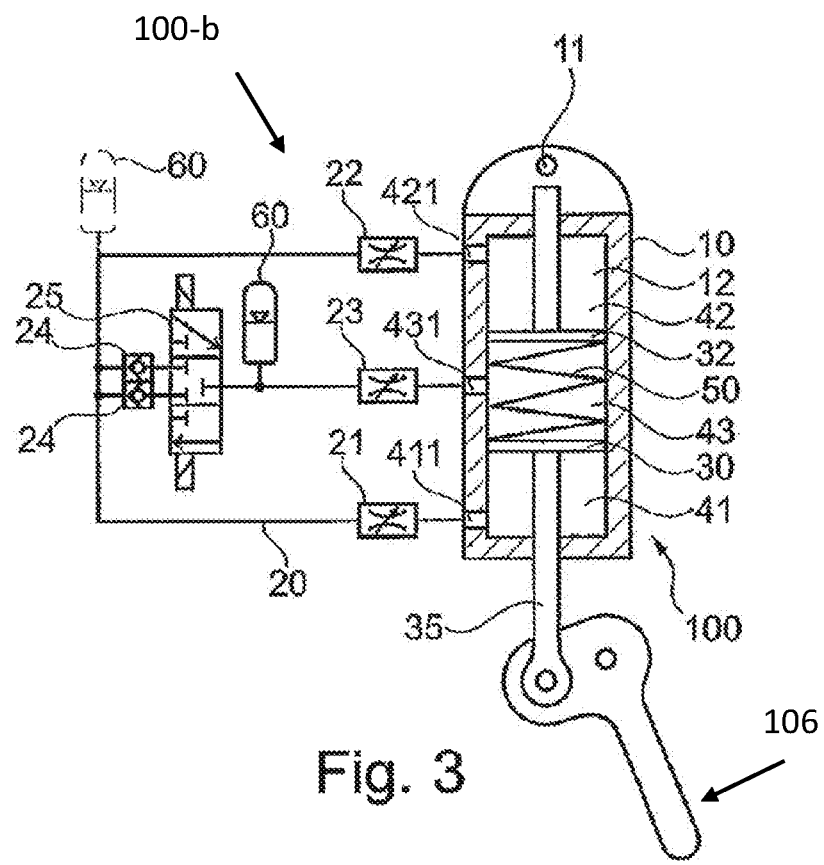
FIG. 3 shows a further embodiment of the exemplary actuator-damper unit of FIG. 2 without a pump.

Another embodiment is shown in FIG. 3 having a hydraulic design which is similar, in principle, to the design of FIG. 2. Instead of a pump 70, as represented in FIG. 2, which can be driven by an electric motor, the AD unit 100-b may provide purely mechanical energy storage in the energy accumulator 50. The energy accumulator 50 may comprise a spring in the enclosed fluid chamber 43. The spring 50 may connect the two pistons 30, 32 together and may couple them in terms of force. The piston rod 35 may be coupled to a lever 106, and so the lever 106 may pivot in the counterclockwise direction during an extension motion, i.e., a movement of the piston rod 35 out of the cylinder 12. During a flexion motion, i.e., during an insertion of the piston rod 35 into the cylinder 12, the lever 106 may rotate in the clockwise direction. Another embodiment is shown with a compensating volume 60. The optional compensating volume 60 is depicted using dashed lines; the compensating volume 60 may be loaded with a preliminary pressure.

Two non-return valves 24 may be assigned to the 3-way valve 25 to enable or block inflow to the additional fluid chamber 43 or from the additional fluid chamber 43 to the two external fluid chambers 41, 42. As shown in FIG. 2, the switching position of the 3-way valve 25 prevents a volume exchange between the two external fluid chambers 41, 42 and the fluid volume in the third fluid chamber 43. If the spring 50 is compressed when the third valve 23 is opened, the fluid is displaced into the compensating volume 60. The 3-way valve 25 allows for a decoupling of the middle fluid chamber 43. When the 3-way valve 25 is in the lower position, an inlet is formed from the two surrounding fluid chambers 41, 42 into the middle, enclosed fluid chamber 43. This may allow an inflow into the chamber 43 by the upper non-return valve 24. When the 3-way valve 25 is in a reversed position, the flow of the fluid from the additional chamber 43 may only return to the two surrounding chambers 41, 42. The position of the particular control valves 21, 22 may control the amount of the volume that flows out of the enclosed chamber 43 into the particular surrounding chambers 41, 42, and where the volume flows.

Figure 4:
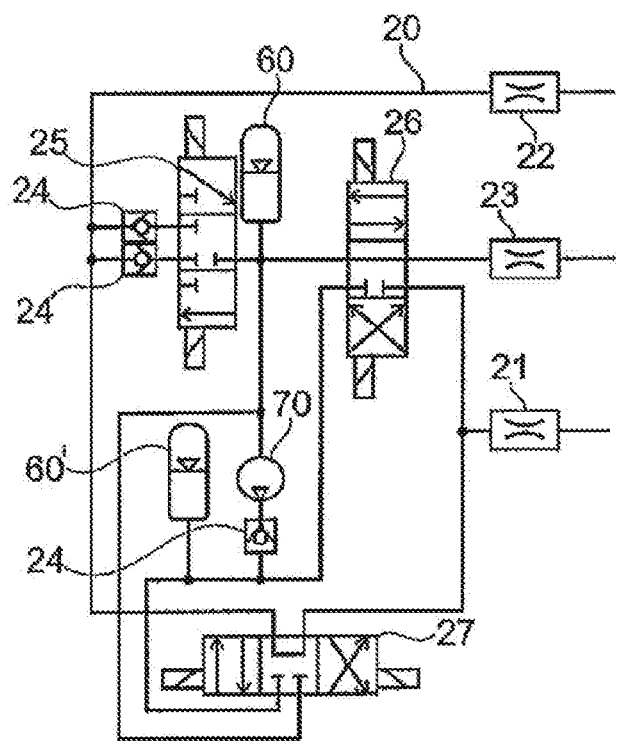
FIG. 4 shows an exemplary embodiment of a hydraulic diagram.

An embodiment of the valve configuration in which the piston-cylinder unit 100 is no longer represented, is shown in FIG. 4. The mechanical design is similar to that shown in FIG. 3. The particular control valves 21, 22, 23 are provided at the access openings 411, 421, 431 in this case as well. The switching carried out by the 3-way valve 25 and the two upstream, contradirectionally oriented non-return valves 24 and the compensating volume 60 are similar to that shown in FIG. 3. As shown in FIG. 4, an additional 3-way valve 26 may be disposed between the first 3-way valve and the control valve 23 of the enclosed fluid chamber 43. The second 3-way valve 26 may either couple or block a hydraulic path to the first chamber 41 and, in the middle position shown in FIG. 4, may provide a passage as well as a hydraulic separation between the first fluid chamber 41 and the third fluid chamber 43. A pump 70 may be coupled to a third 3-way valve 27 via a non-return valve 24 and an optional buffer volume 60' in the form of an additional pressure accumulator. The third 3-way valve 27 may be coupled into a hydraulic line of the first fluid chamber 41 and, in the middle position shown in FIG. 4, may provide a passage. The switching position shown in FIG. 4 may correspond to the hydraulic arrangement according to FIG. 3. The second 3-way valve 26 may close the fluid line 20 between the pump 70 and the first fluid chamber 41. The second 3-way valve 26, when in an upper position, may connect the pump 70 and the enclosed, additional fluid chamber 43 using a cross-linked switching.

The third 3-way valve 27 may connect the pump 70 to the upper, second fluid chamber 42. When the third 3-way valve is switched to a predetermined position it may establish a connection to the first fluid chamber 41.

The valve arrangement may allow for diverse damping, storage, and activation. To store energy during a flexion movement, the upper valve 22 may be closed, the middle valve 23 may throttled, and the lower valve 21 may be open. At the same time, the first 3-way valve 25 may be displaced into the right position, i.e., upward. The two other 3-way valves 26, 27 may remain in the particular middle position. As a result, the volume of the third chamber 43 may be reduced, the spring 50 may be loaded, and kinetic energy may be converted into potential energy and stored.

To release energy in the extension direction, the upper valve 22 may be closed, the middle valve 23 may be opened, and the lower valve 21 may be throttled. The first 3-way valves 25 may be moved downward into a left position allowing fluid from the first fluid chamber 41 and, if necessary, from the compensating volume 60 to flow into the enlarging third fluid chamber 43.

To dampen during a flexion movement, the upper valve 22 may be throttled, the middle valve 23 may be closed, and the lower valve 21 may be opened. The 3-way valves 25, 26, 27 may be located in the middle position shown. In this position, the volumetric flow may be directed from the upper, second chamber 42 into the lower, first chamber 41. The fluid flow may be obstructed using the upper throttle valve 22 and the remaining components may not activate causing a pure hydraulic system.

To provide damping in the extension movement, in which the piston rod 35 extends out of the housing 10, the upper valve 22 is opened, the middle valve 23 remains closed, and the lower valve 21 is throttled, and so a reversal to damping in the flexion is effectuated.

To introduce an active force in the flexion direction, i.e., to push the first piston 30 into the housing 10, the upper valve 22 is opened, the middle valve 23 is closed, and the lower valve 21 is throttled. The 3-way valves 25, 26 are in the middle position as shown and the third 3-way valve may be displaced toward the right. This may create a cross-linked coupling of the fluid lines to couple the pump 70 to the lower, first fluid chamber 41, and pressure may be applied to the fluid chamber 41. As a result, a flexion movement may be actively assisted.

Conversely, to achieve an active extension position, the pressure from the pump 70 is directed into the upper chamber 42 which is located on the side of the piston 30 facing away from the piston rod 35. The upper valve 22 is throttled, the middle valve 23 is closed, and the lower valve 21 is open. The third 3-way valve 27 is in the left position which may couple the pump 70 to the upper fluid chamber 42 by the parallel line.

When the middle valve 23 is closed, the volume in the third chamber 43 does not change, and the second piston and the first piston 30 are moved downward. Therefore, an extension movement is actively assisted by means of the pump 70.

When the upper valve 22 is closed, the middle valve 23 is throttled, and the lower valve is opened, an active supply of energy is supplied to the pump 70 in the extension direction, and the energy accumulator 50 releases mechanically stored energy. The first 3-way valve 25 and the third 3-way valve 27 may be in the middle position. The second 3-way valve 26 may be in the right position, and so additional pressure from the pump 70 may be applied onto the middle fluid chamber 43. The spring 50 may expand, which may be amplified by the pump 70. As a result, the first piston 30 may be moved downward and an extension movement is effectuated.

An active influencing during the flexion movement, accompanied by a simultaneous storage of flexion energy, is effectuated when the upper valve 22 is closed, the middle valve 23 is opened, and the lower valve 21 is throttled. The first 3-way valve 25 and the third 3-way valve 27 is in the middle position. The second 3-way valve 26 in the left position. The fluid from the pump 70 may be introduced into the first, lower fluid chamber 41 to assist the flexion. The valve position may also store the flexion energy in the energy accumulator 50.

The upper valve 22 and the middle valve 23 may be opened and the lower valve 21 may be closed for the pump 70 to load the mechanical energy accumulator 50 without a flexion or an extension movement occurring. The first 3-way valve 25 may interrupt the fluid flow in the middle position, the second valve 26 may be in the middle position, and the third 3-way valve 27, in the left position, may couple the pump 70 and the upper chamber 42 and the middle chamber 43. The second 3-way valve 26 may be in the middle position, which may pump fluid into the middle chamber 43. The second piston 32 may move away from the first piston 30, which may increase the volume within the third fluid chamber 43, and tension the spring 50.

Figure 5:
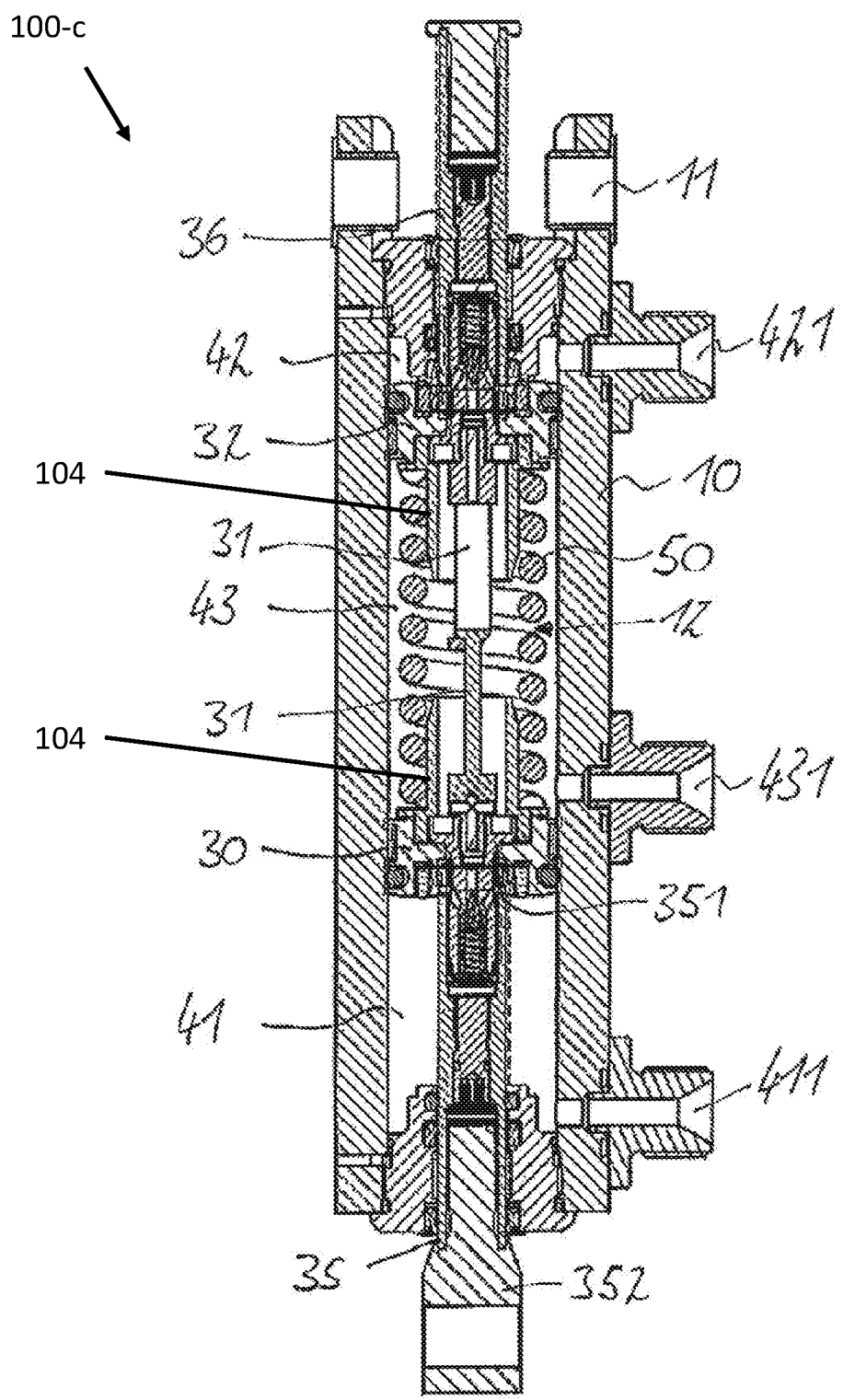
FIG. 5 shows an exemplary sectional representation of an embodiment of the actuator-damper unit.

FIG. 5 shows an additional embodiment of an AD unit 100-c without valves. The housing 10 may be essentially cylindrical and may comprise an internal cylinder 12 in which two pistons 30, 32 are mounted so as to be longitudinally displaceable. The first piston 30 is connected to a first end 351 of a piston rod 35 which extends out of the housing 10 and, at the outer, second end 352 comprises a receptacle for attachment, for example, to a prosthetic knee joint or an orthotic knee joint.

The second piston 32 may connect to an outwardly extending rod 36 and may separate the cylinder volume into two fluid chambers 42, 43. A spring 50, which may act as a mechanical energy accumulator, may be disposed in the middle fluid chamber 43. As shown in FIG. 5, the pistons 30, 32 are disposed in an uppermost position. For example, the first, lower fluid chamber 41 has a maximum volume, and the second, upper fluid chamber 42 has a minimum volume. The volume of the middle fluid chamber 43 between the two movable pistons 30, 32 may be maximized. The mechanical coupling device 31 may engage when the maximum volume of the middle chamber 43 is reached and may limit the maximum volume of fluid chamber 43. As a result, if the accumulator is empty during an extension movement, the upper, second piston 32 is carried along via the coupling device 31 through an extension of the piston rod 35 out of the housing 10. Access openings 411, 421, 431 are disposed at an end regions of the cylinder 12 and close to the maximum position of the first piston 30. The spring 50 is guided centrally over mandrels 104 to avoid tipping or jamming. Alternatively, the energy accumulator 50 may also be a spiral spring, a disk spring, a disk spring stack, any type of mechanical spring, a pneumatic element or an elastomeric component, wherein extension springs as well as compression springs may be utilized.

Figure 6:
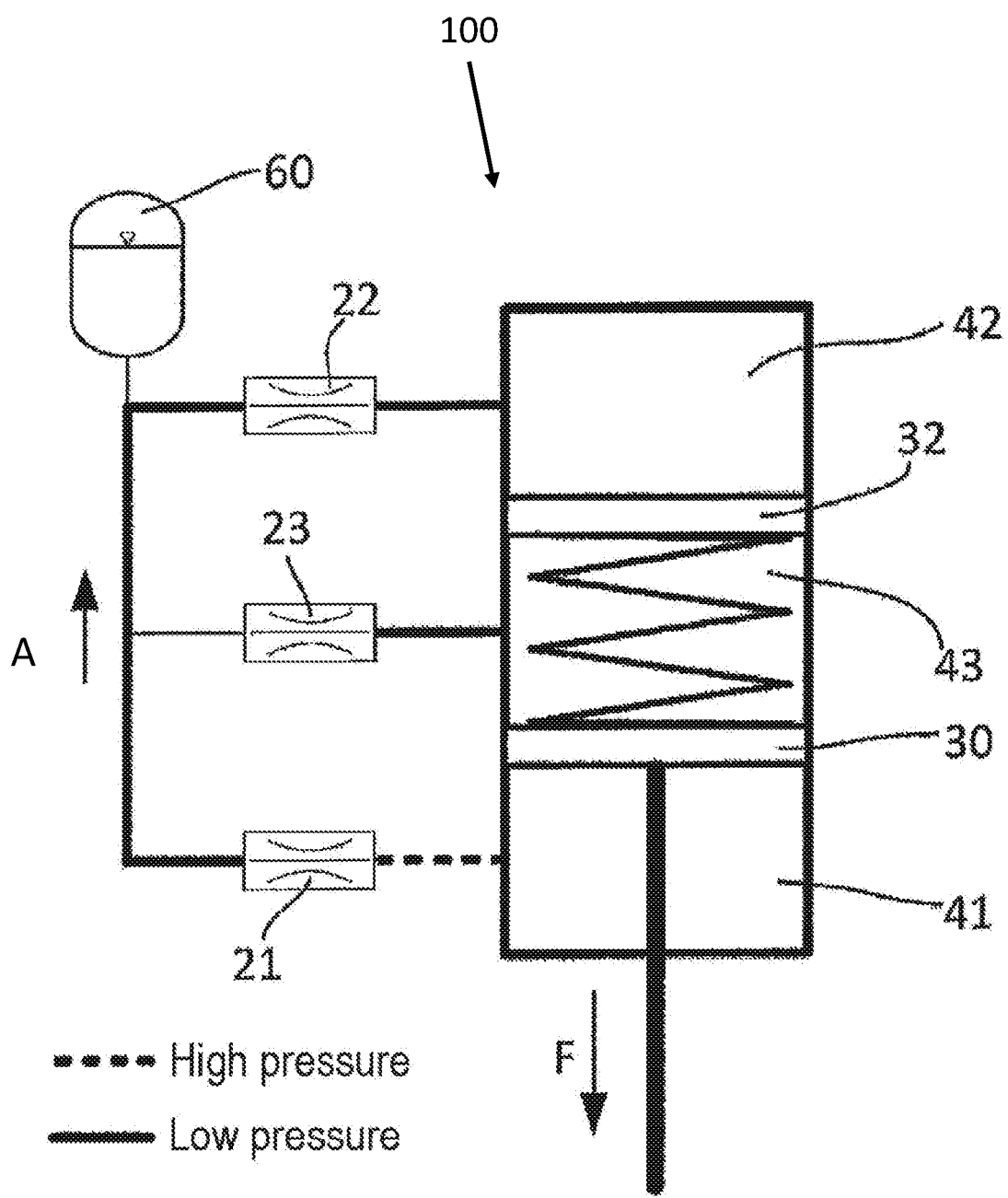
FIGS. 6 to 16 show representations of different load states and valve positions in exemplary embodiments of the actuator-damper unit.

FIG. 6 shows another embodiment of an actuator-damper unit 100 where, for switching position during a damping for the extension, the upper valve 22 is open, the lower valve 21 is throttled, and the middle valve 23 is closed. The fluid may flow to the compensating volume 60, or may flow from the fluid chamber 41 to the fluid chamber 42.

Figure 7:
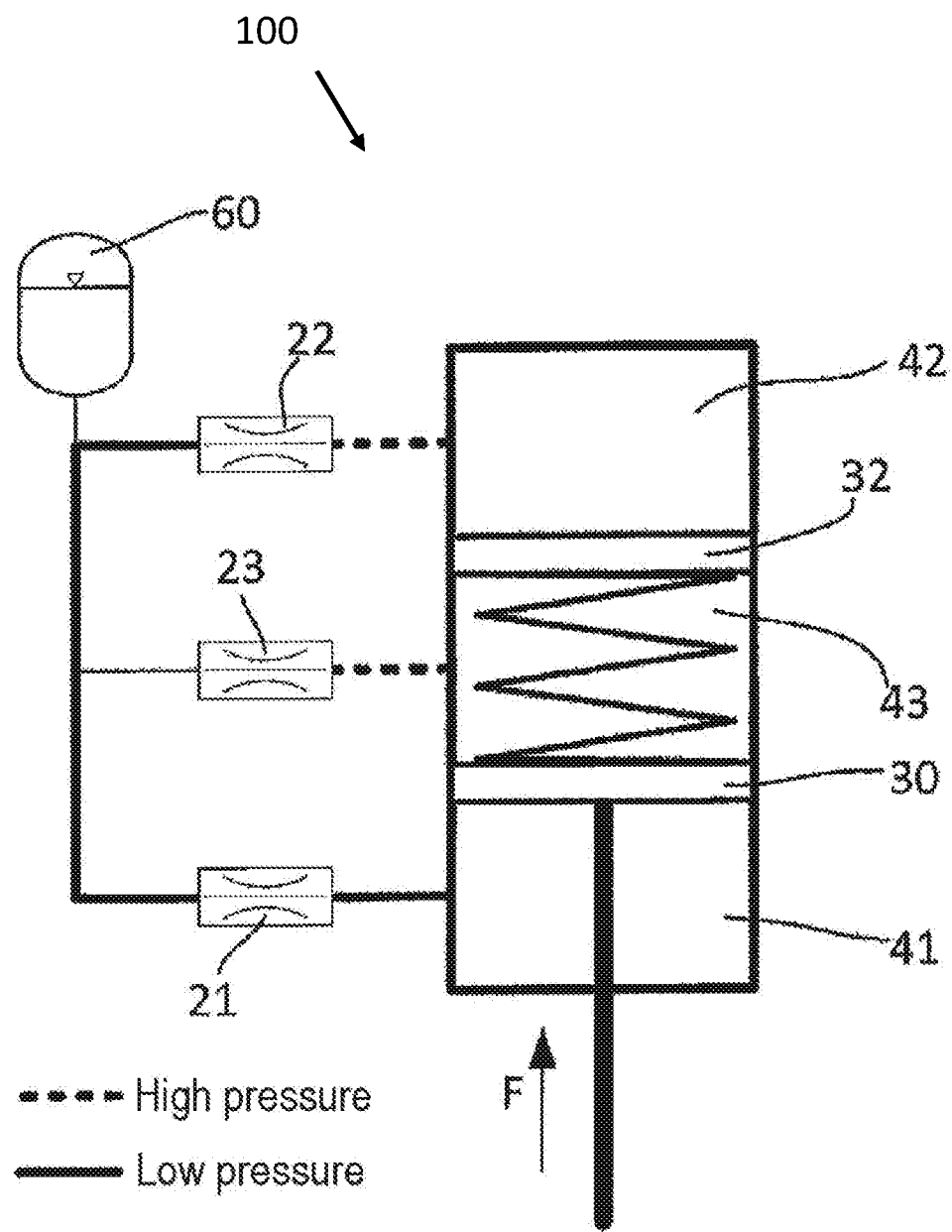

FIG. 7 shows the AD unit during a flexion movement. The upper valve 22 is throttled, the lower valve 21 is opened, and the middle valve 23 is closed. The spring 50 may be ineffective because fluid exchange from the chamber 43 is prevented because the pistons 30 and 32 are connected to form a virtual rigid body. The valve 22 dissipates the effect of the force F in a controlled manner.

Figure 8:
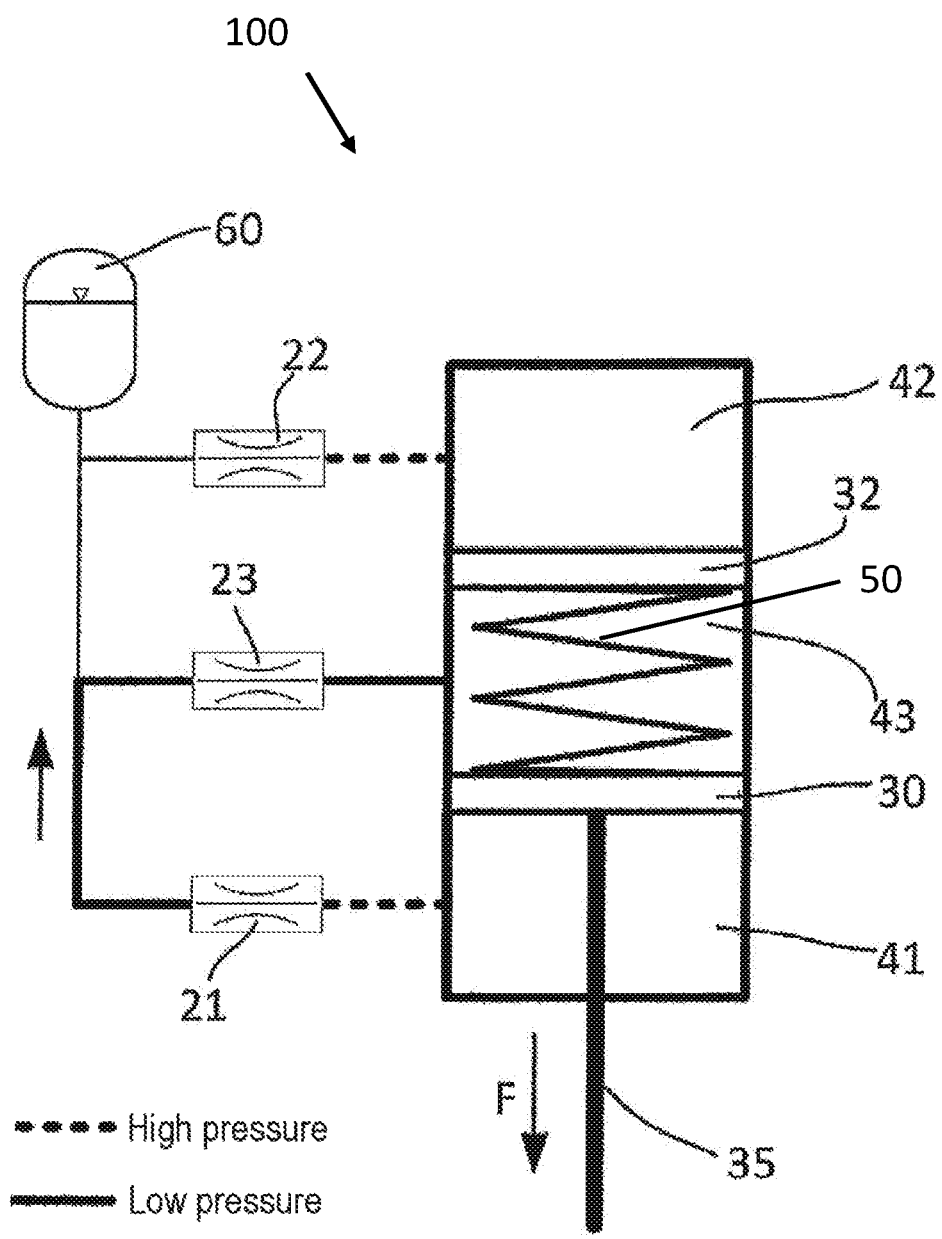

FIG. 8 shows the AD unit 100 a release of energy from the accumulator 50 during extension. For example, during extension, the piston rod 35 may extend, in conjunction with a throttling. The upper valve 22 is closed, the middle valve 23 is opened, and the lower valve 21 is throttled. A high pressure may be present in the upper chamber 42 and the fluid may flow from the lower chamber 41 into the middle chamber 43 in a throttled manner. The compensating volume 60 may supplement the fluid volume that is missing due to the piston rod volume.

Figure 9:
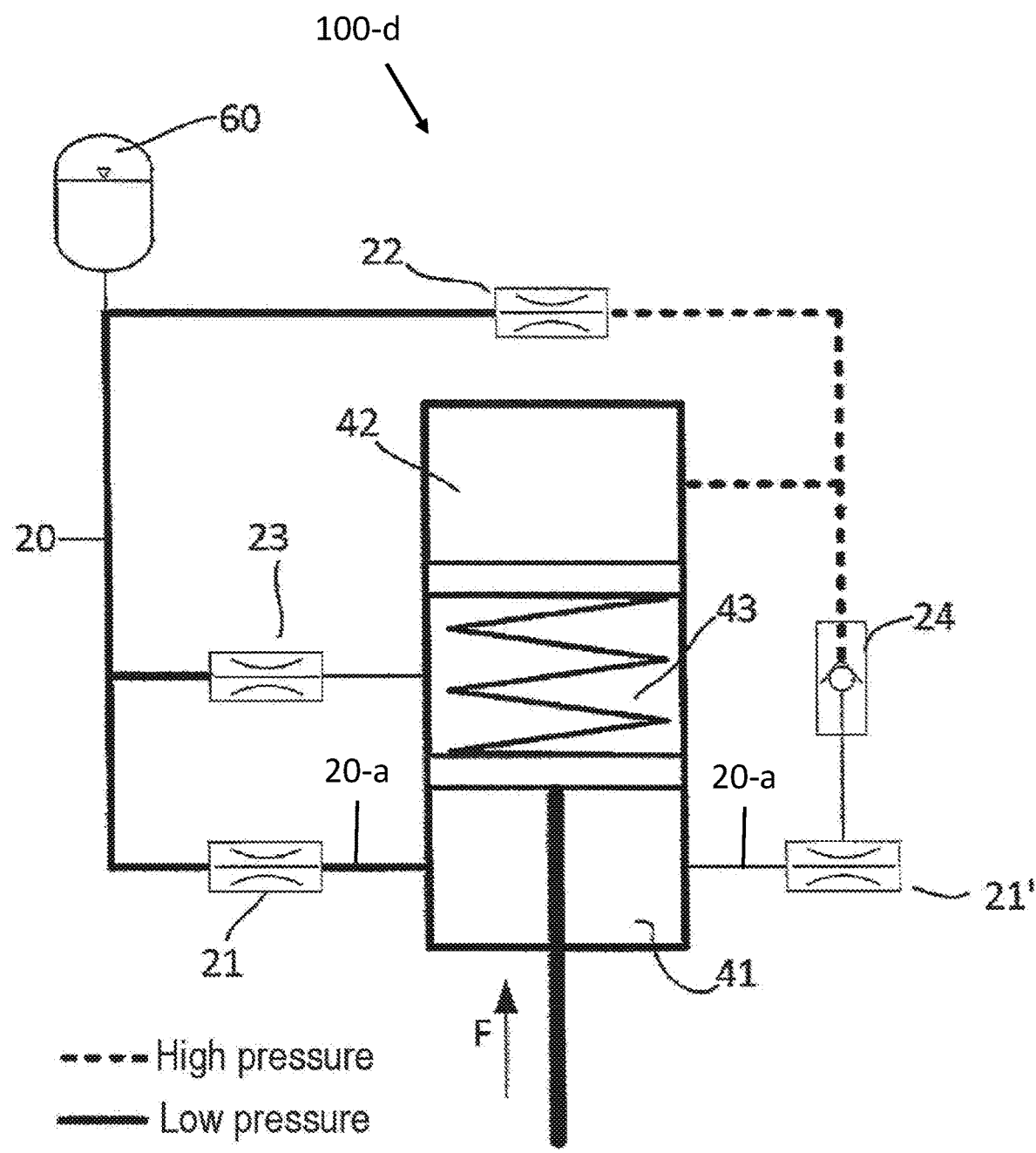

FIG. 9 shows an actuator-damper unit 100-d with an alternative fluid line 20 routing. Two fluid lines 20-a may connect to the corresponding access openings through switching valves or control valves. Alternatively, both fluid lines 20-a may connect to the same opening and may branch off after the connection. The fluid lines 20 branch off from the first fluid chamber 41. To achieve damping in the flexion movement, the upper valve 22 may be throttled and the valve 23 for the middle fluid chamber 43 and an auxiliary valve 21' may be closed. The auxiliary valve 21' may be connected to the first lower fluid chamber and may be upstream from a non-return valve 24. The left control valve 21 of the lower fluid chamber 41 may be open, and so, during a flexion movement, the fluid may flow from the upper fluid chamber 42, through the throttle valve 22, and into the lower fluid chamber 41. The throttle effect may occur at the upper valve 22.

Figure 10:
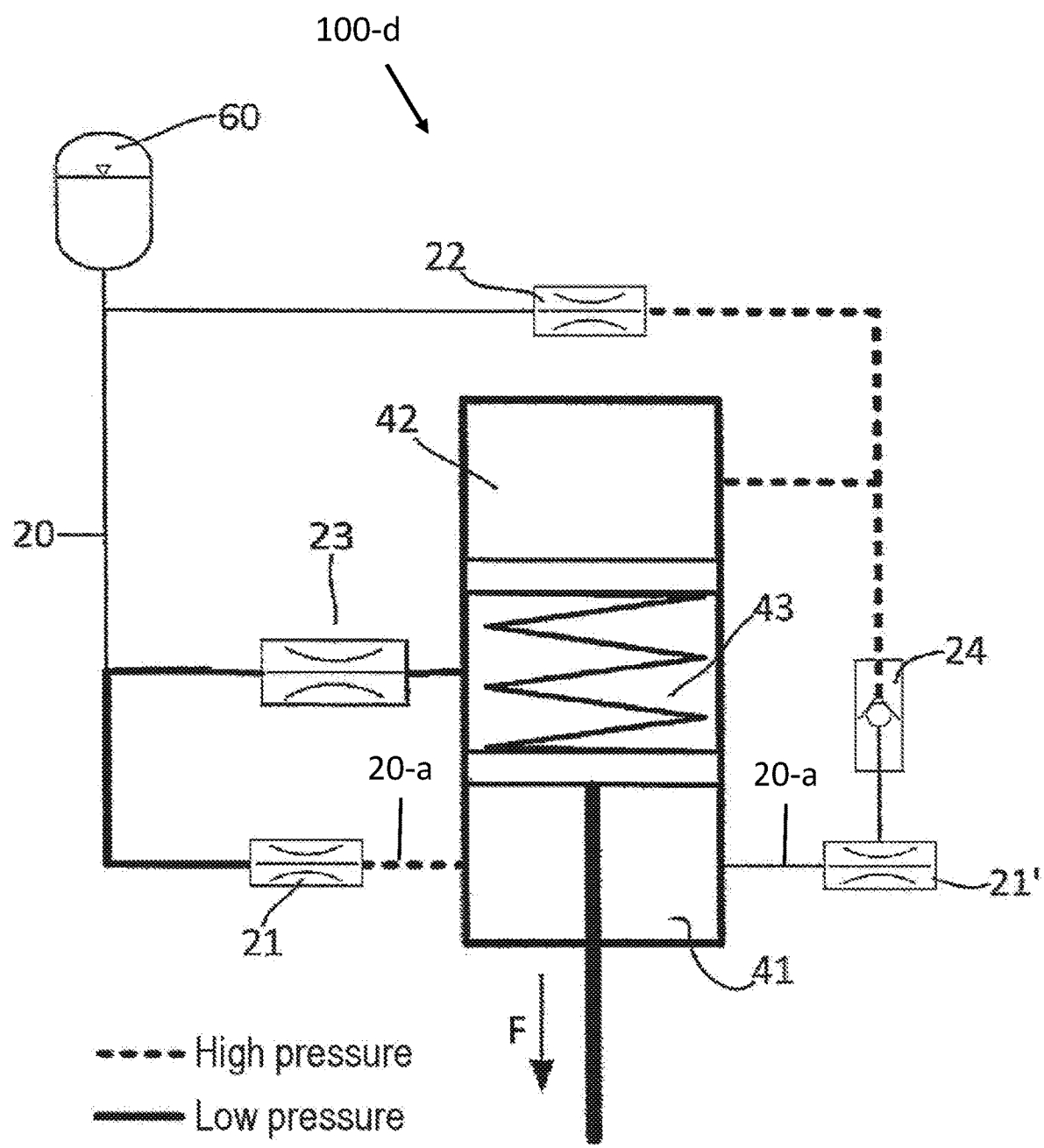

FIG. 10 shows an alternative arrangement of the same mechanical design of the AD unit 100-d shown in FIG. 9. The first valve 21 may be throttled to release energy from the middle fluid chamber 43. In addition, the third valve 23 may be opened toward the middle fluid chamber 43. Fluid may flow from the first fluid chamber 41 into the middle fluid chamber 43. The second control valve 22 toward the upper fluid chamber 42 may be closed.

Figure 11:
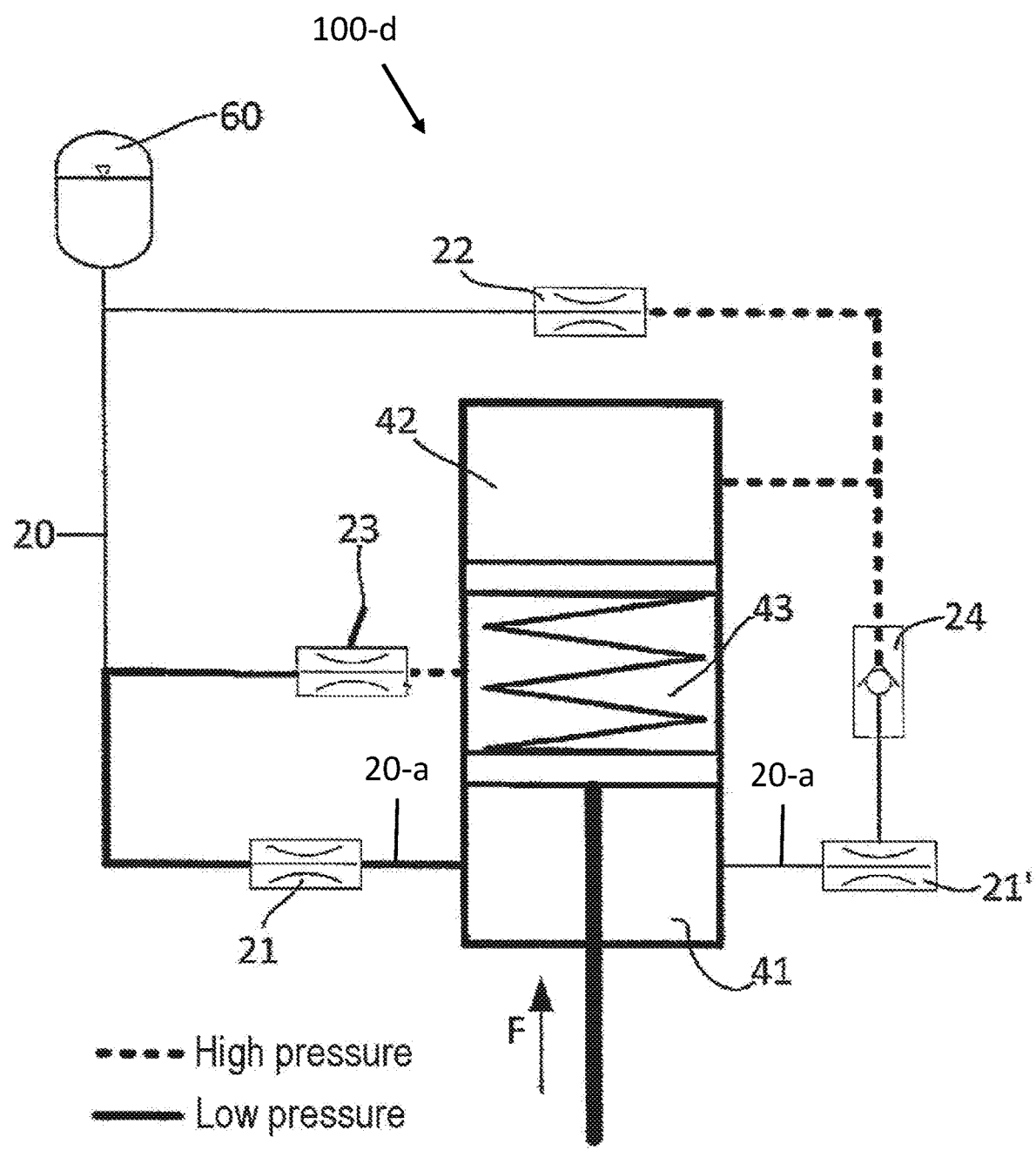

FIG. 11 shows an actuator-damper unit 100-d wherein the valve positions result in stored kinetic energy during a flexion movement. The first auxiliary valve 21' and the second valve 22 closed. The third valve 23 is throttled. The volume of the fluid chamber 43 may be reduced. For example, an additional non-return valve 24 may only permit a reduction in the volume of the third fluid chamber 43. This configuration enables outflow of the fluid chamber 43. In contrast, the embodiment shown in FIG. 10, enables inflow into the third fluid chamber 43 through the upstream non-return valve 24.

Figure 12:
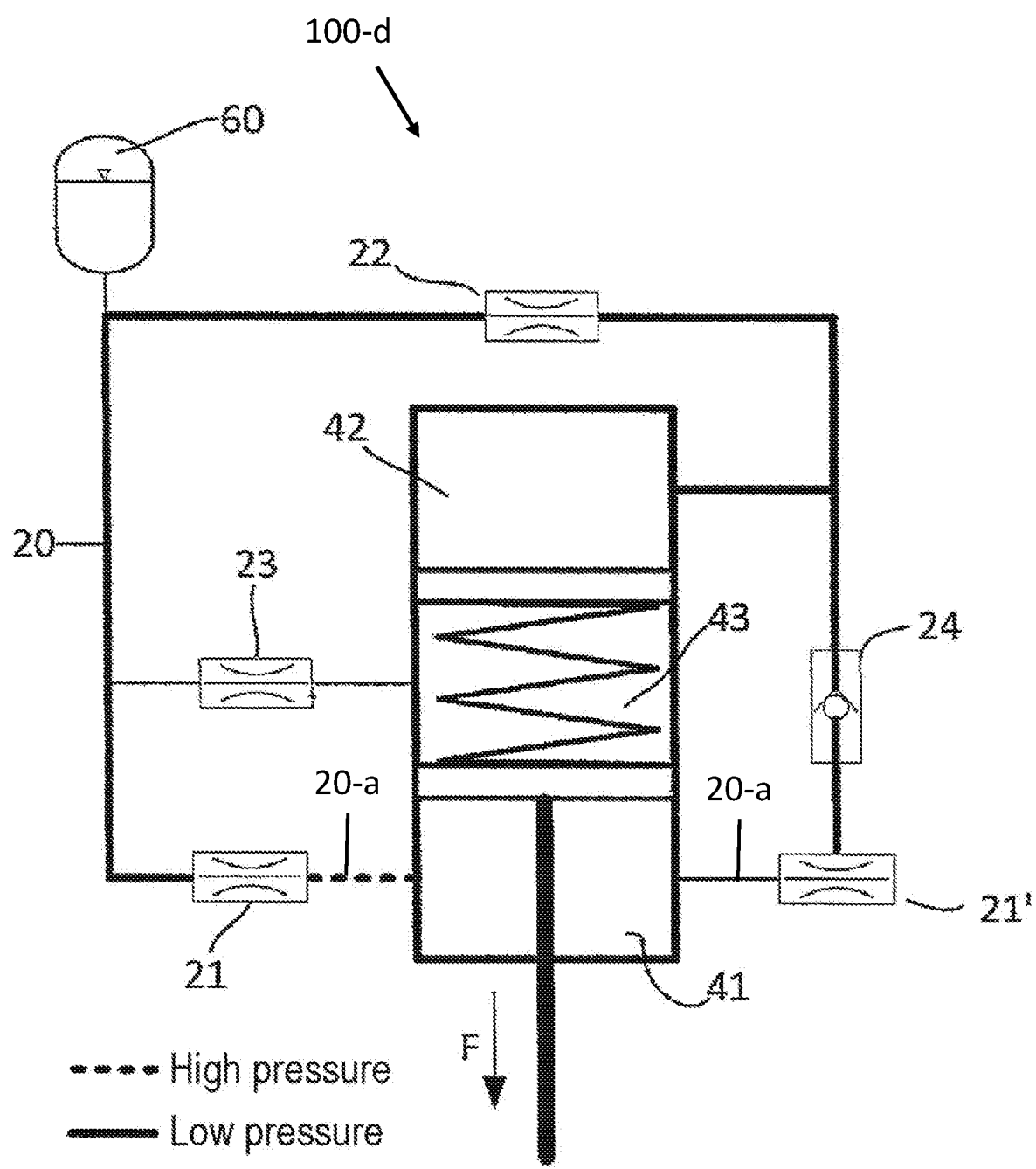

FIG. 12 shows an actuator-damper unit 100-d with a valve configuration to achieve damping in the extension direction. The upper valve 22 is opened, the middle valve 23 is closed, and the first valve 21 is throttled, and the auxiliary valve 21' may additionally be closed.

Figure 13:
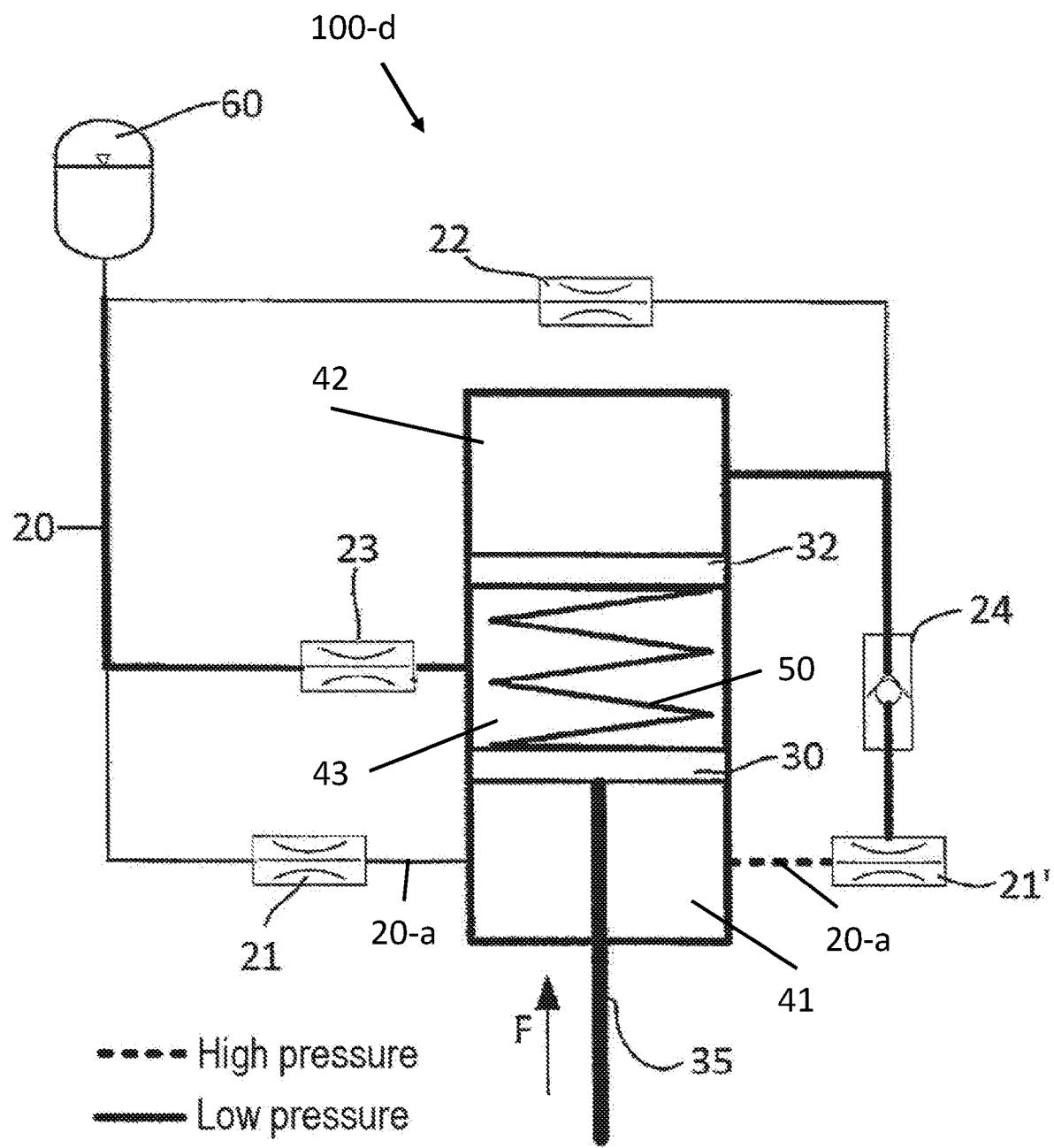

FIG. 13 shows an actuator-damper unit 100-d with a valve configuration for a release of stored energy in a flexion direction. The upper valve 22 is closed and the first auxiliary valve 21' is opened. The first valve 21 is closed and the third valve 23 is opened. This valve configuration can expand the spring 50 and introduce fluid into the first fluid chamber 4l through the piston 32, through the non-return valve 24 and the first auxiliary valve 21'.

Figure 14:
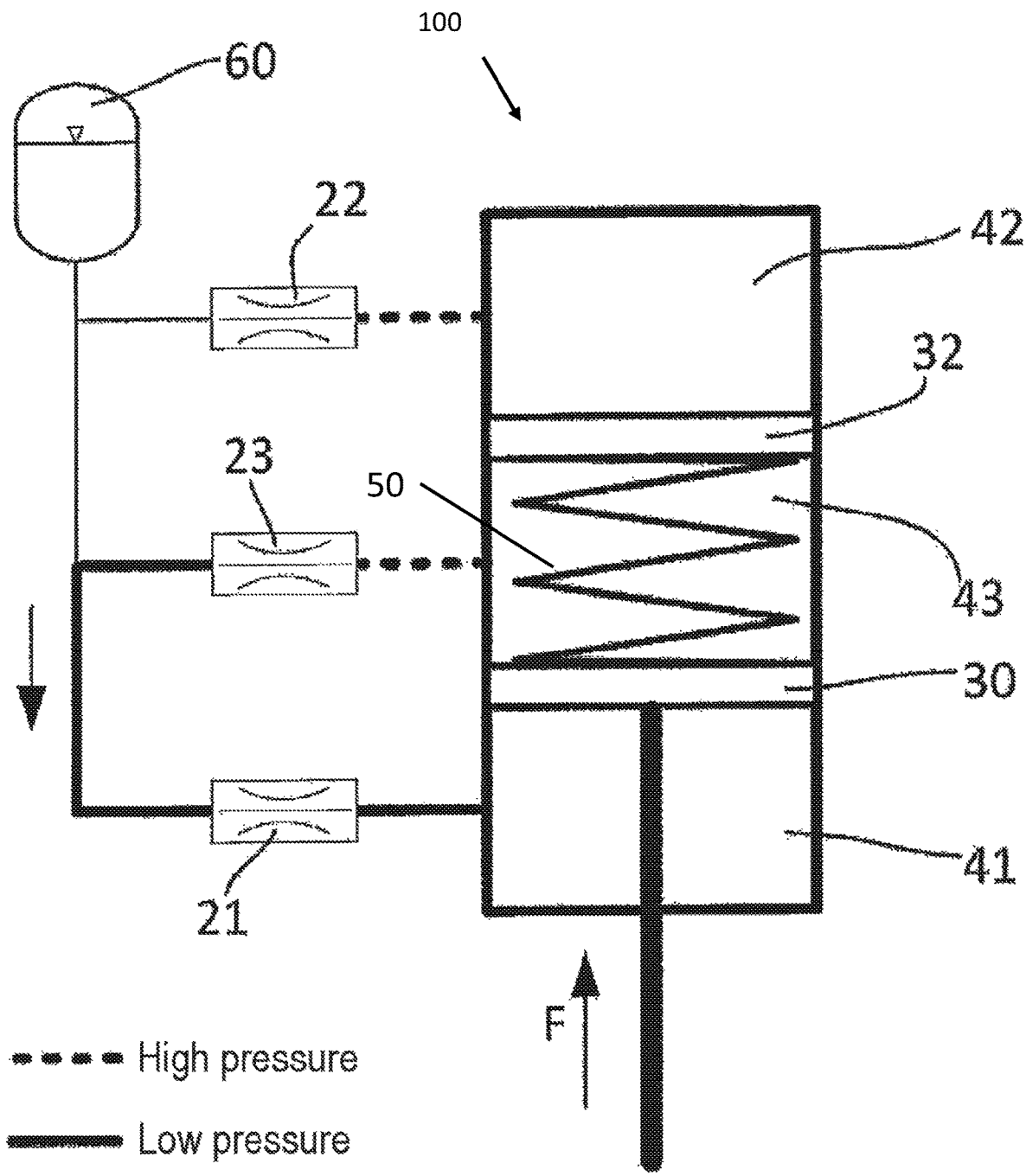

FIG. 14 is a schematic representation of the actuator-damper unit 100 shown in FIG. 1. In order to store energy while simultaneously throttling energy during a flexion movement, the first valve 21 is opened, the third valve 23 toward the middle chamber 43 is throttled, and the upper valve 22 toward the upper fluid chamber 42 is closed. As a result, the spring 50 may be compressed and the throttling in the valve 23 may cause damping during flexion movement.

Figure 15:
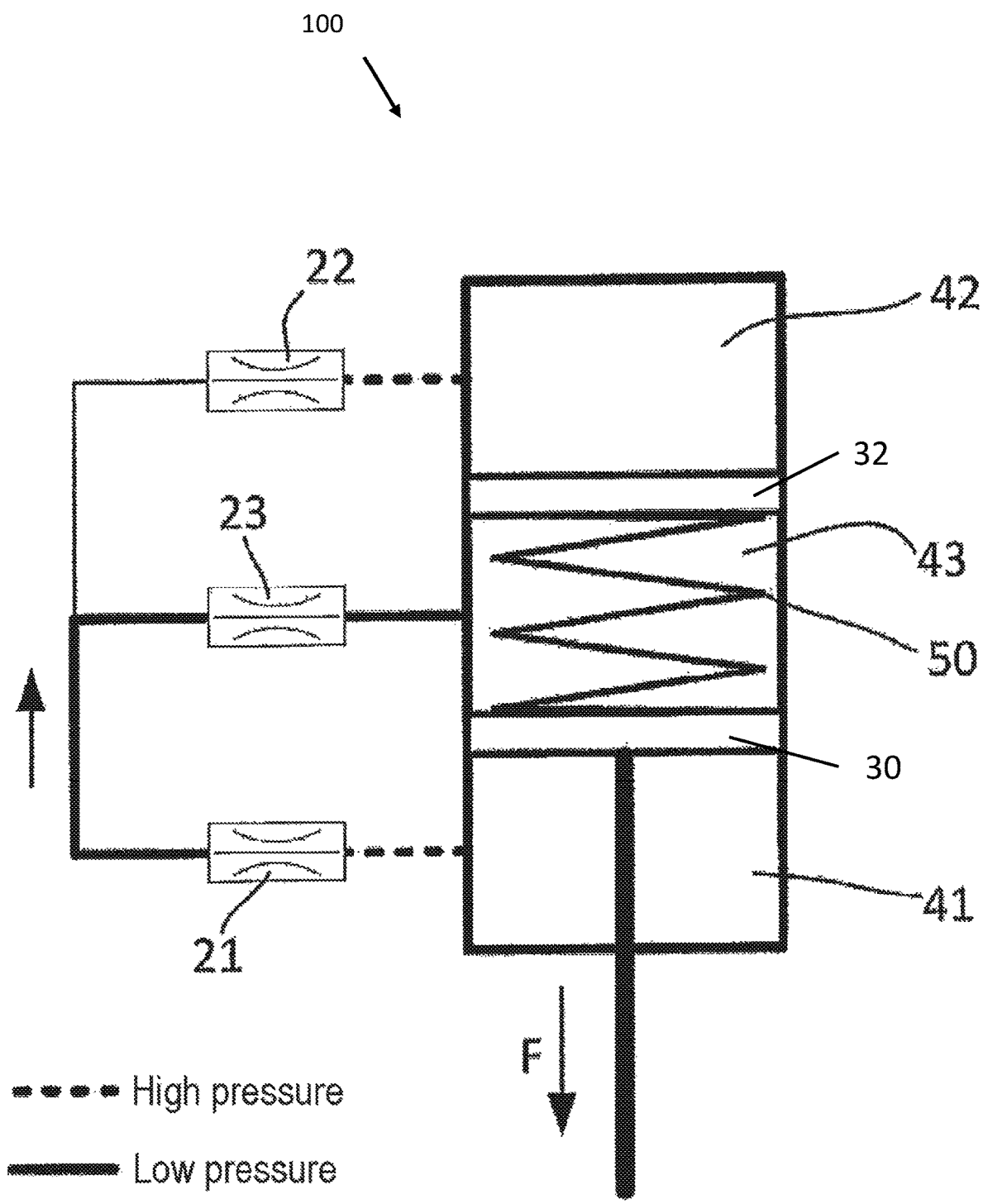

FIG. 15 shows an alternative valve configuration of an actuator-damper unit 100 wherein an extension movement occurs with assistance by the energy accumulator 50 as well as a throttling. The upper valve is closed, the middle valve 23 is open, and the throttling may take place via the partially open or throttled valve 21. The spring 50 may expand and the decreasing volume of the first chamber 41 flows through the throttled valve 21 into the middle fluid chamber 43, and so a throttled extension movement is achieved.

Figure 16:
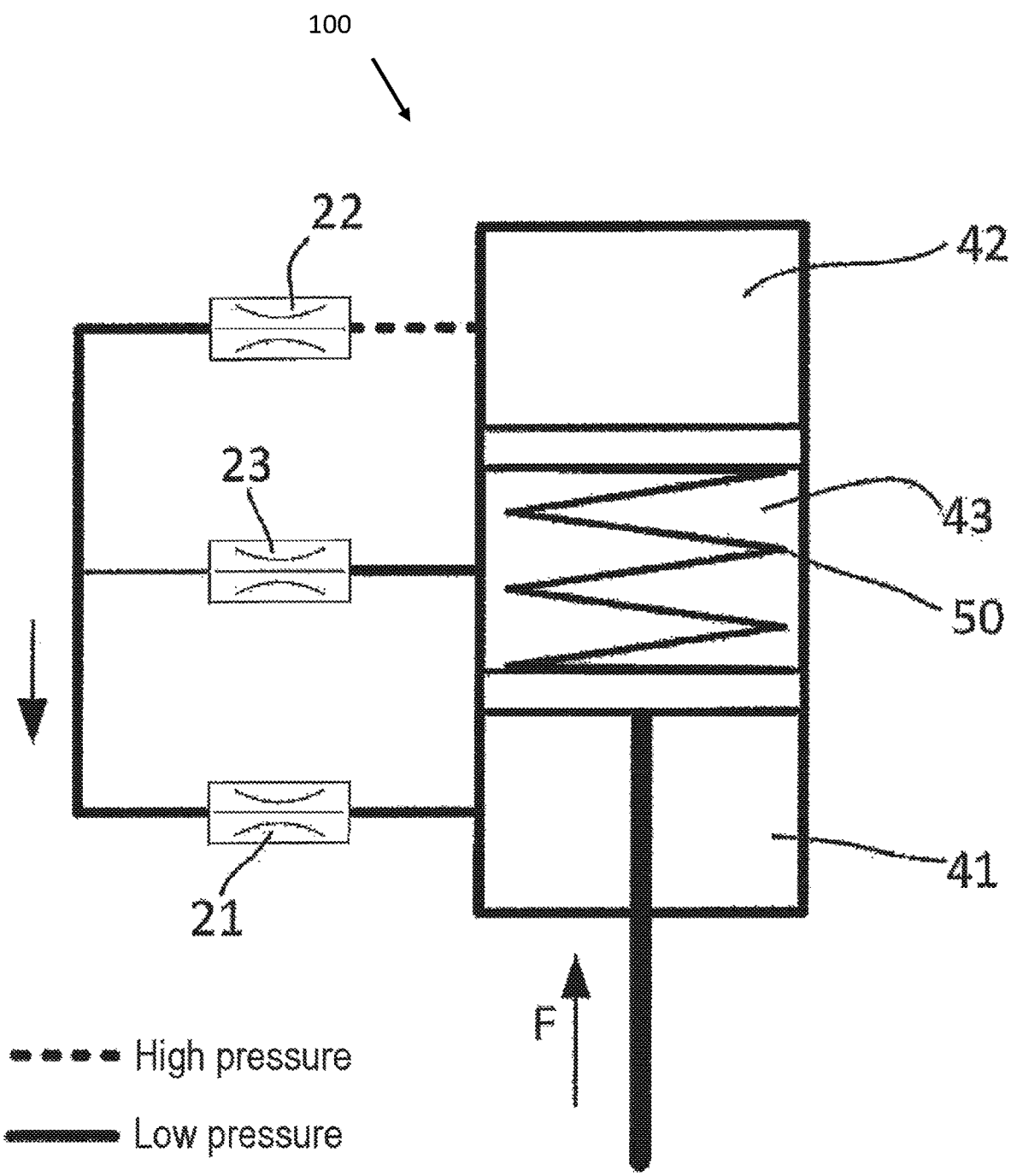

FIG. 16 shows a valve configuration of an actuator-damper unit 100 for pure damping during a flexion movement. The first valve 21, the third valve 23 is closed, and a second valve 22 is throttled. During flexion, the hydraulic fluid may flow out of the upper chamber 42 into the lower chamber 41. The volume of the third fluid chamber 43 may not change since the middle valve 23 remains closed or the volume may change only due to the volume differences effectuated by the piston rod.

Figure 17:
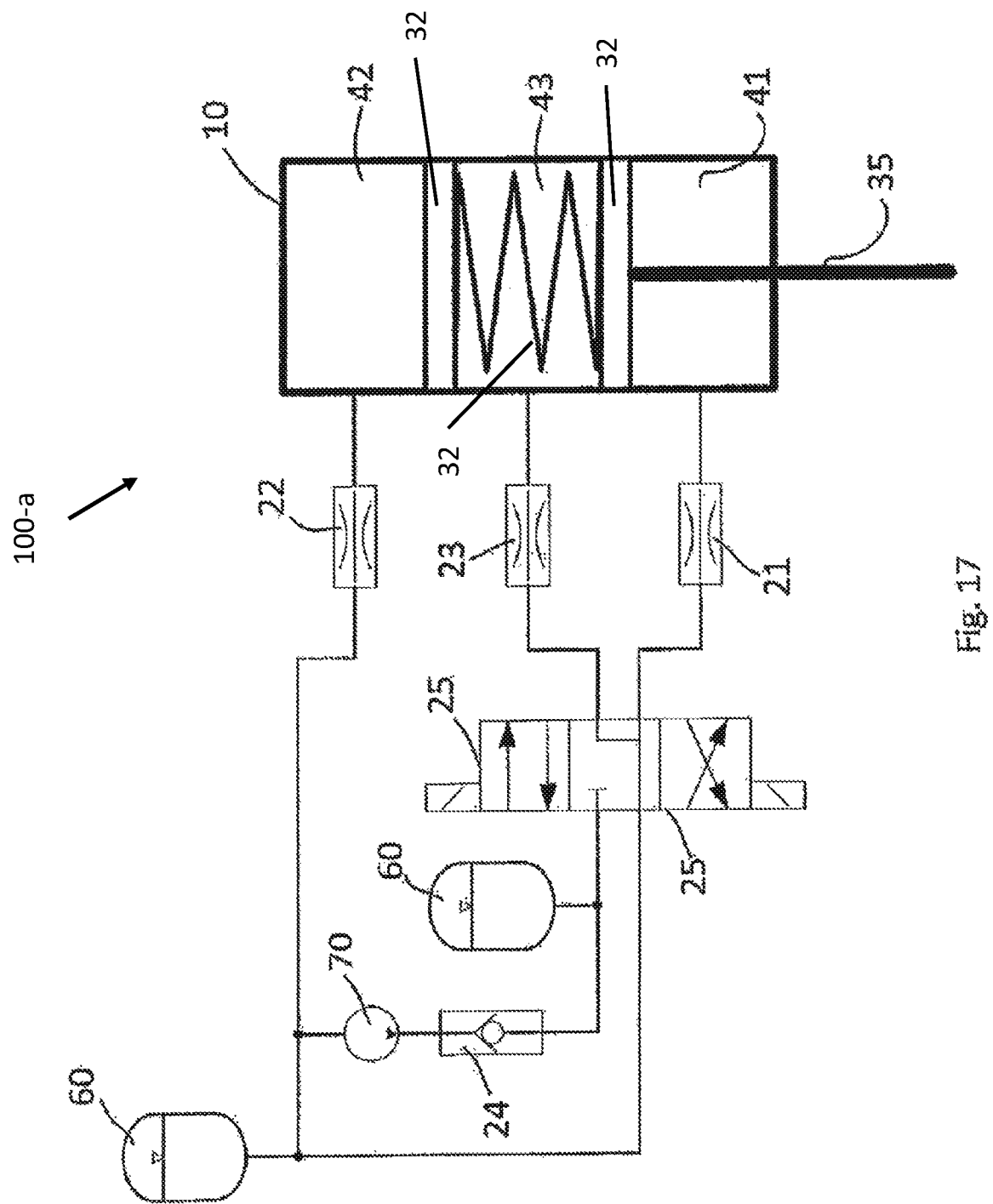
FIG. 17 shows a further embodiment of the present disclosure.

FIG. 17 shows a switching arrangement according to the actuator-damper unit 100-a in FIG. 2. By way of the 3-way valve 25, the pump 70 may amplify a force of the extension movement. The force transmitted by the piston rod 35 is a superimposition of the spring force and the force generated by the pump pressure. In this case, the upper valve 22 is closed, the two other valves 21, 23 are open, and the 3-way valve 25 is in the upper position which is not crossed out. In the flexion direction, the two connected pistons 30, 32 and the piston rod 35 may be displaced with the aid of the pump 70. For example, the valve 23 is closed, the upper valve 22 and the lower valve 21 are open, and the 3-way valve 25 is in the lower position which is crossed out. To displace only the lower piston 30 while simultaneously storing energy in the elastic element 50, the middle valve 23 and the lower valve 21 are open and the upper valve 22 is blocked, and the 3-way valve 25 is in the lower position which is crossed out.

Figure 18:
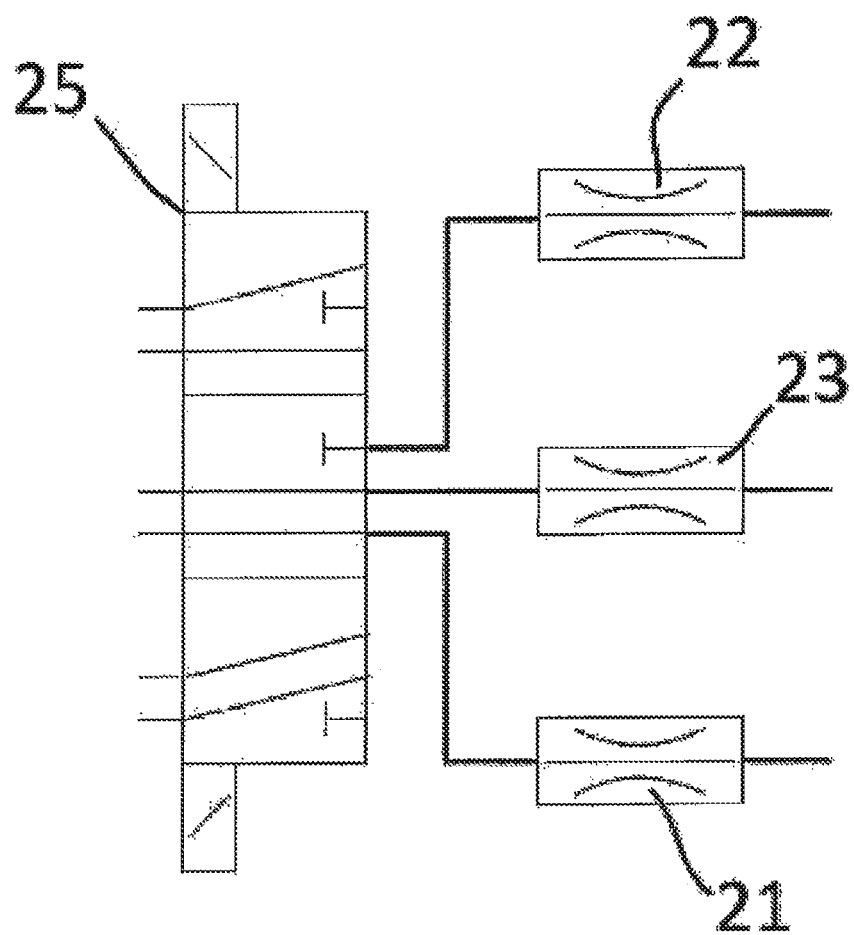
FIG. 18 shows an alternative embodiment of an exemplary 3-way valve.

FIG. 18 shows an alternative three-way valve 25 embodiment for the storing and releasing energy during flexion and extension movements, and also provides damping in the flexion and extension directions. The three valves 21, 22, 23 may be switched in each switching position of the three-way valve 25. In the shown middle position, the fluid coming from the pump 70 is fed to the third, middle fluid chamber 43. A line to the first, lower valve 21 is established, and a coupling to the upper valve 22 is prevented. In the upper position, when the lower switching block is coupled to the pump 70, pressure fluid is applied to the upper valve 23 and the lower fluid chamber 41 is blocked. In the lower position, in which the upper switching block is coupled to the pump 70, access to the middle, enclosed fluid chamber 43 is blocked and the two outer chambers 41, 42 are coupled to each other and may be provided with pressure fluid from the pump 70. Pressure must be present in both outer chambers 41, 42 in order to provide an active force in both directions without creating a change within the energy accumulator 50.

Figure 19:
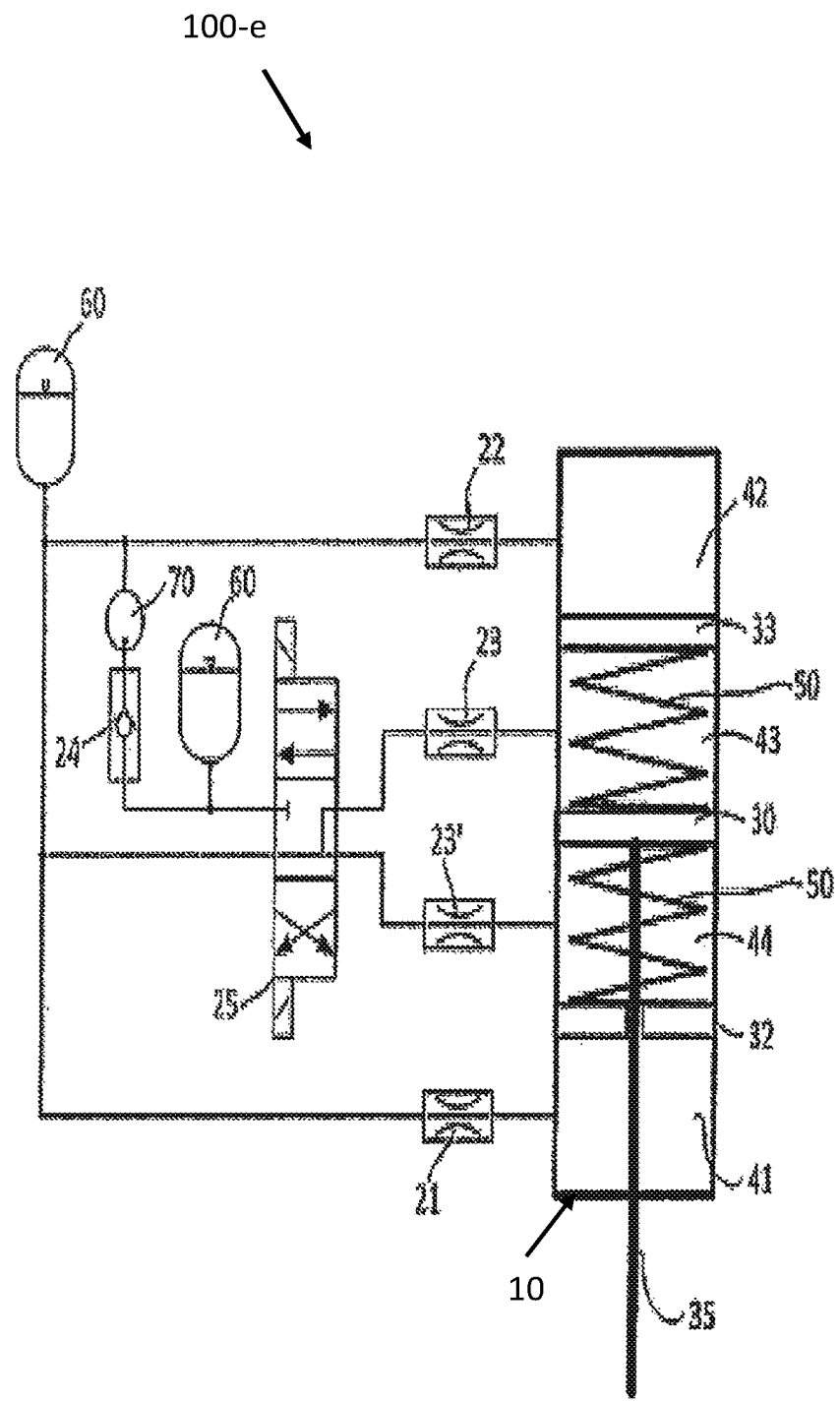
FIG. 19 shows a schematic representation of a further embodiment of an actuator-damper unit comprising two additional pistons.

FIG. 19 shows another embodiment of the AD unit 100-e. Three pistons 30, 32, 33 are disposed in the housing 10, forming a total of four fluid chambers 41, 42, 43, 44. In the embodiment shown, the piston 30 is fixedly connected to the piston rod 35 and is disposed between the two further pistons 32, 33. At least one energy accumulator 50, in the form of springs, pneumatic cushions, or elastomeric elements, may be disposed in each of the fluid chambers 43, 44 enclosed between the pistons 30, 32; 30, 33. The two variable-volume chambers 43, 44 formed between the two pistons 32, 33 may be selectively filled with the pressure fluid by the pump 70 with the aid of the three-way valve 25. For this purpose, the three-way valve 25 is moved either into the upper position or into the lower position. In addition, pressure can build up in the two outer chambers 41, 42 relatively easily to apply an active force in the flexion direction and in the extension direction. In this embodiment, energy is stored and released, as necessary, both in the flexion movement and in the extension movement. By connecting the pump 70, a force amplification is provided during the release of energy in the flexion direction and in the extension direction. Finally, an elastic oscillation of the middle piston 30 about the equilibrium position of the springs 50 within chambers 43 and 44 can take place, for example, so-called "bouncing".

Figure 20:
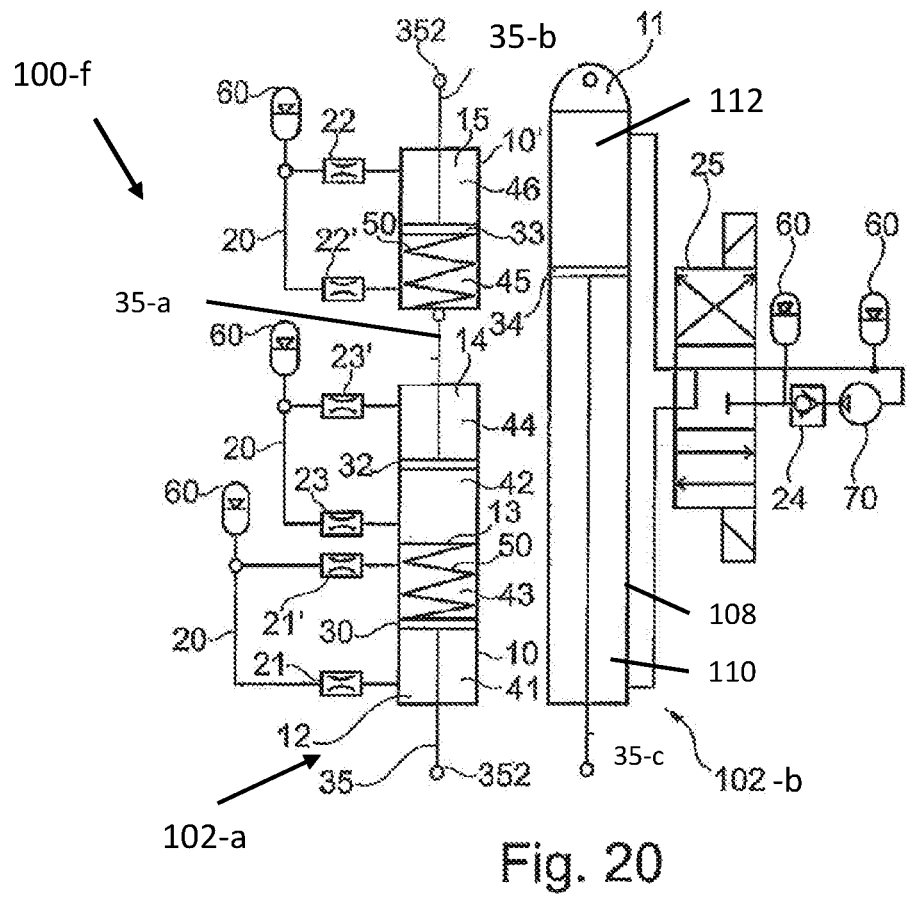
FIG. 20 shows a schematic representation of a further embodiment of an actuator-damper unit comprising a second piston-cylinder unit and two cylinder housings.

FIG. 20 shows another embodiment of an actuator-damper unit 100-f. The piston-cylinder unit may be subdivided into three separate cylinder areas, two of which are disposed in a housing 10. The lower piston rod 35 is connected to the first piston 30. The first fluid chamber 41 is located between the lower cylinder wall and the piston 30. An energy accumulator 50 is disposed in a second fluid chamber 43 on the opposite side of the piston 30. The energy accumulator 50 may comprise a spring and may be supported against the piston 30 on one side and, on a second side may be supported against a separation wall 13. A second, longitudinally displaceable piston 32 is located on the other side of the separation wall 13. The second piston 32 may be disposed in a second cylinder 14 which is fluidically decoupled from the first cylinder 12, and subdivides the cylinder volume into two fluid chambers 42, 44. Typically, no energy accumulator 50 is disposed within the two fluid chambers 42, 44. A piston rod 35-a may couple the second piston 32 to a separate cylinder housing 10' which is displaceably mounted relative to the first housing 10 by the piston rod 35 of the second piston 32. A third piston 33 may be displaceably mounted in a third cylinder 15 within the second housing 10'. The third cylinder 15 may be fluidically decoupled from the other cylinders 12, 14. A third piston rod 35-b may attach to the third piston 33. The third piston rod 35-b may extend out of the second housing 10' and can attach to a component of the orthotic or prosthetic device. The piston 33 may subdivide the third cylinder 15 into two fluid chambers 45, 46.

A second energy accumulator 50-a may be disposed in the fluid chamber 45 which faces the first housing 10 and faces away from the third piston rod 35. The three pistons 30, 32, 33 are therefore connected in series, namely two in one shared housing 10 comprising a separation wall 13 and the third in a second housing 10' which is movable relative to the first housing 10. The two housings 10, 10' may be combined to form one assembly. The fastening elements 352 may fasten the ends of two piston rods 35 which extend out of the housings 10, 10'.

Each fluid chamber 41, 42, 43, 44, 45, 46 may have an access opening provided with a valve 21, 21', 22, 22', 23, 23'. The fluid chambers 41, 43; 42, 44; 45, 46 which are separated, in each case, by the movable piston 30, 32, 33, respectively, are connected by a fluid line 20 and an assigned compensating volume 60, to which pressure may be applied. The valves 21, 21', 22, 22', 23, 23' can influence the damping behavior and the storage behavior of the energy accumulator 50.

A second piston-cylinder unit 102-b, which may comprise a pure actuator, may be disposed in parallel to the first piston-cylinder unit 102-a. The forces of the two piston-cylinder units 102-a, 102-b may be superimposed. One piston 34 may be displaceably mounted in a housing 108 and may separate the two fluid chambers 110, 112 from each other. A non-return valve 24 and two compensating volumes 60 may couple a pump 70 to the second piston-cylinder unit 102-b. A three-way valve 25 may be disposed between the pump 70 and the fluid chambers 110, 112 in the second piston-cylinder unit 102-b. The three-way valve 25 may allow pressure to be applied either to an extension chamber or a flexion chamber, and so an active introduction of force takes place depending on the position of the three-way valve 25. Driving does not take place in the middle position shown. If the three-way valve 25 is displaced downward, extension takes place. If the three-way valve 25 is displaced upward, flexion takes place, in which the piston rod 35-c is retracted into the housing of the second piston-cylinder unit 102. A connection 11 may fasten to a prosthetic or orthotic device.

Figure 21:
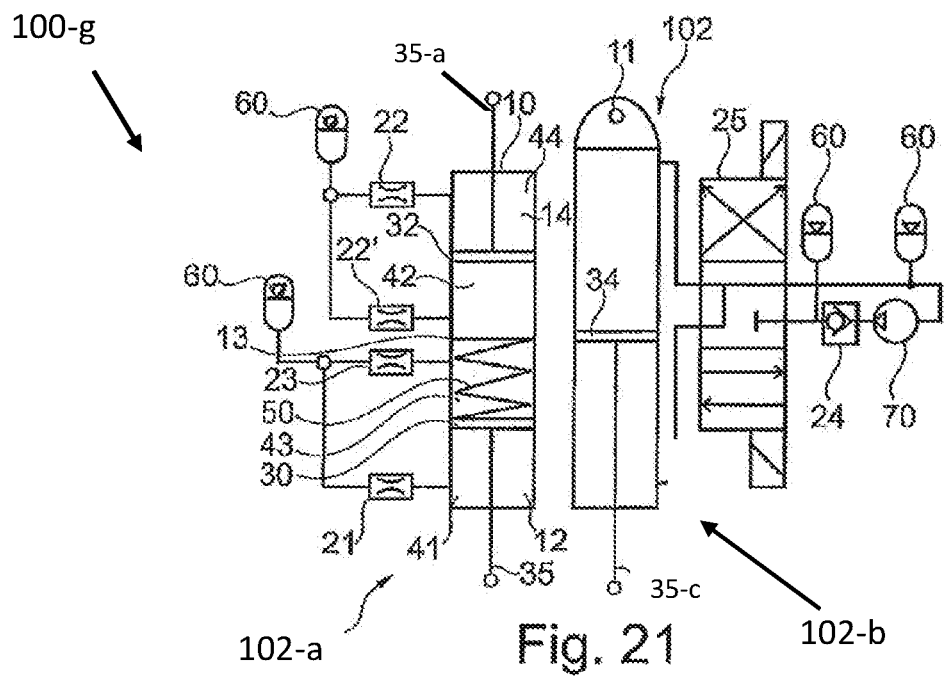
FIG. 21 shows a further embodiment of the actuator-damper unit in FIG. 20 comprising four fluid chambers and one additional piston-cylinder unit.

FIG. 21 is a further embodiment of the AD unit 100-g shown in FIG. 20. The second piston-cylinder unit 102-b and a first piston-cylinder unit 102-a enable a separate active actuator. In contrast to the embodiment according to FIG. 20, FIG. 21 provides energy accumulation only in the flexion direction. Energy release from the accumulator 50 is provided only in the extension direction. The housing 10 of the first piston-cylinder unit 102-a is subdivided by a separation wall 13, and two fluidically separated cylinders 12, 14 are formed. Piston rods 35, 35-a extend out of the housing 10 at both ends of the housing 10. The piston rod 35 is connected to a first piston 30 which separates a first fluid chamber 41 and a second fluid chamber 43 from each other. A mechanical energy accumulator 50 in the form of a spring is disposed in the second fluid chamber 43. The second piston 32, which also separates two fluid chambers 42, from each other, is longitudinally displaceably disposed on the other side of the separation wall 13. The fluid flow between the fluid chambers 41, 43; 42, separated by the pistons 30, 32 may be controlled via the valves 21, 23, 22', 22. A compensating volume 60 is assigned to each pair of fluid chambers 41, 43; 42, 44. In the embodiment represented, storage of mechanical energy and damping are separated, and there is a separate actuation via a pump 70. A connection 11 may fasten to a prosthetic or orthotic device.

Figure 22:
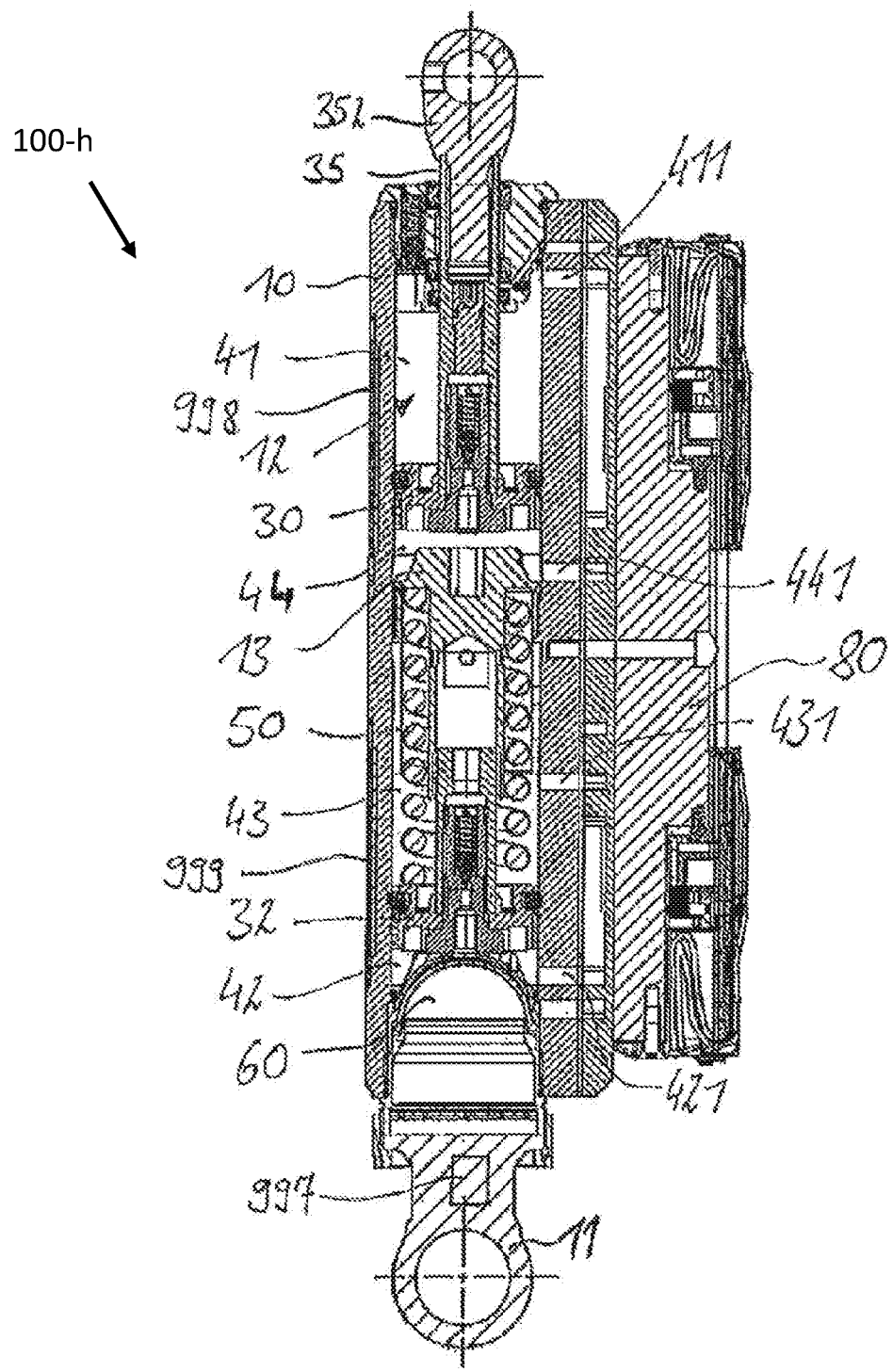
FIG. 22 shows a sectional representation of an exemplary actuator-damper unit comprising four fluid chambers.

FIG. 22 shows a sectional representation of an AD unit 100-h comprising four fluid chambers 41, 42, 43, 44. A piston rod 35 guides a first piston 30 in a cylinder 12 which is formed by the housing 10. An end or fastening element 352 of the piston rod 35 opposite the first piston 30 extends out of the housing 10 and fastens to an orthotic or prosthetic device. The first piston 30 separates two fluid chambers 41, 44 from each other. Fluid chamber 44 is at least partially formed by a fixed separation wall 13 within the cylinder 12. A further cylinder section, in which a second piston 32 is displaceably mounted, is formed on a side of the separation wall 13 facing away from the piston 30. The second piston 32 may form two fluid chambers 42, 43. The fluid chamber 43 may be located between the separation wall 13 and the second piston 32 is provided with an energy accumulator 50 which may comprise, for example, a spiral spring, coiled spring, elastomer material, or other device. All fluid chambers 41, 42, 43, 44 may have an outlet openings 411, 421, 431, 441.

A control device 80 may alter the outlet openings 411, 421, 431, 441, through various inclusive valves (not shown) to form different hydraulic interconnections and alter the damping behavior, storage behavior, and/or actuation behavior. A compensating volume 60 may be integrated into the AD unit 100-h. A connection 11 may fasten to a prosthetic or orthotic device. A force sensor 997, which may deliver signals for the control device 80, may be integrated into the connection 11. In addition, the AD unit 100-h may comprise integrated sensors 998, 999 which may measure piston positions. The sensor 998 may measure a position of the working piston which may provide information regarding a joint angle. The sensor 999 may measure a position of the piston 32, which may also be referred to as an accumulator piston, and may provide information regarding the stored energy.

The AD unit 100-h may provide a pure damper, a pure actuator, and/or a combination of a damper comprising an actuator. In an embodiment acting as a pure actuator, damping does not have to occur. In an embodiment acting as a pure damper, actuation or energy storage does not have to occur. The AD unit 100-h may be configured in such a way that at least one of the three options for use is implemented.

Figure 23:
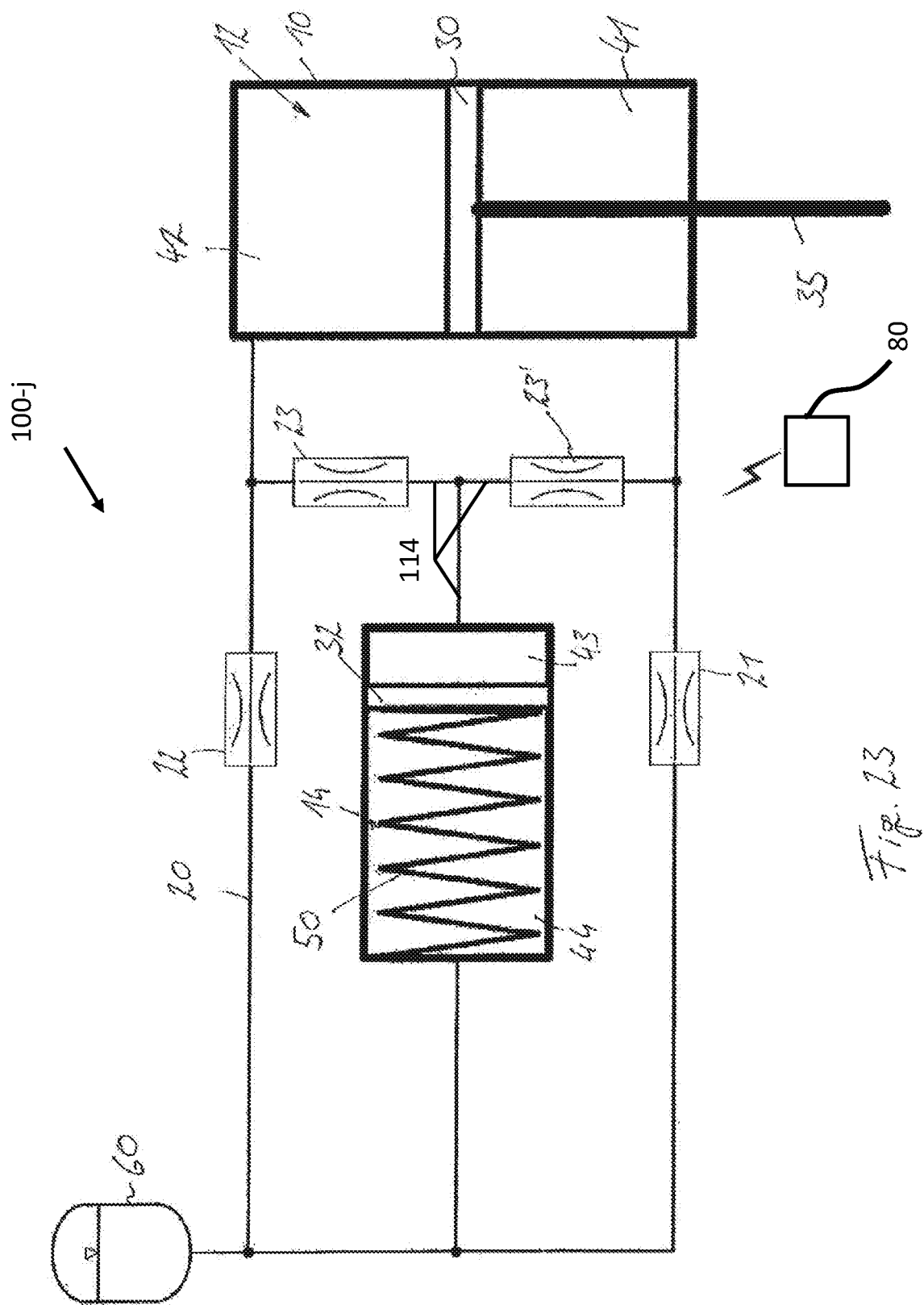
FIG. 23 shows a further embodiment of an actuator-damper unit comprising a separate, movable piston.

FIG. 23 shows a schematic representation of an AD unit 100-j comprising a longitudinally displaceable piston 30 in a cylinder 12 formed in the housing 10. The AD unit 100-j may store and arbitrarily release energy in both directions of piston 30 travel. The piston 30 may be mechanically coupled to an orthopedic or orthotic device (not shown) via a piston rod 35. The piston 30 separates two fluid chambers 41, 42. Fluid lines 20 connect the two fluid chambers 41, 42. Switching or control valves 21, 22 or check valves may be disposed in the fluid lines 20. A compensating volume 60 may connect to the fluid line 20 to allow for volume fluctuations, for example, volume fluctuations resulting from a retraction and extension of the piston rod 35 and, in some embodiments, temperature fluctuations or volume leakages. The volumetric flow between the fluid chambers 41, 42 may be controlled by control valves 21, 22. A control device 80 may adjust the control valves 21, 22. The control device 80 may be computer-controlled, in some embodiments it may be automated and comprise a processor, in further embodiments, the control device 80 may be mechanical and manually operated.

A second cylinder 14 may be fluidically coupled to the fluid chambers 41, 42. A further piston 32 may be displaceably mounted in the second cylinder 14. An energy accumulator 50 may preload the piston 32 against a fluid pressure. The energy accumulator 50 may comprise a spring element or elastomeric element. For example, in some embodiments, the energy accumulator 50 may comprise a coiled spring, a compression spring, a constant spring, a helical spring, or the like. The second piston 32 may subdivide the second cylinder 14 into two further fluid chambers 43, 44 each of which is connected to a fluid line 114. Control valves 23, 23' may be disposed in a connection line 114 between the fluid lines 20 from the first fluid chambers 41, 42 and control the inflow and the outflow of the fluid, in particular the hydraulic fluid, into and out of the fluid chamber 43 to which pressure is applied. If the energy accumulator 50 is to be loaded, a predetermined valve position directs fluid into the variable-volume fluid chamber 43 as a result of a movement of the first piston 30. If the piston rod 35 is retracted, for example, the piston 30 moves downward. The lower first control valve 21 is open to allow fluid flow out of the chamber 44 and into the lower fluid chamber 41 to move the piston rod 35 out. The lower control valve 23' in the connection line 114 is closed, the upper control valve 23 in the connection line 114 is open, and the control valve 22 in the fluid line 20 is closed.

This valve configuration causes the fluid to exit the upper fluid chamber 42 through the upper control valve 23 into fluid line 20 and into the variable-volume fluid chamber 43. As fluid chamber 43 fills with fluid, the spring 50 is compressed and energy is stored. To maintain the stored energy level, the control valves 23, 23' in the connection line 114 are closed. To release the stored energy in the energy accumulator 50, the corresponding control valve 23, 23' is opened to create the desired actuation of the first piston 30 and piston rod 35.

Figure 24:
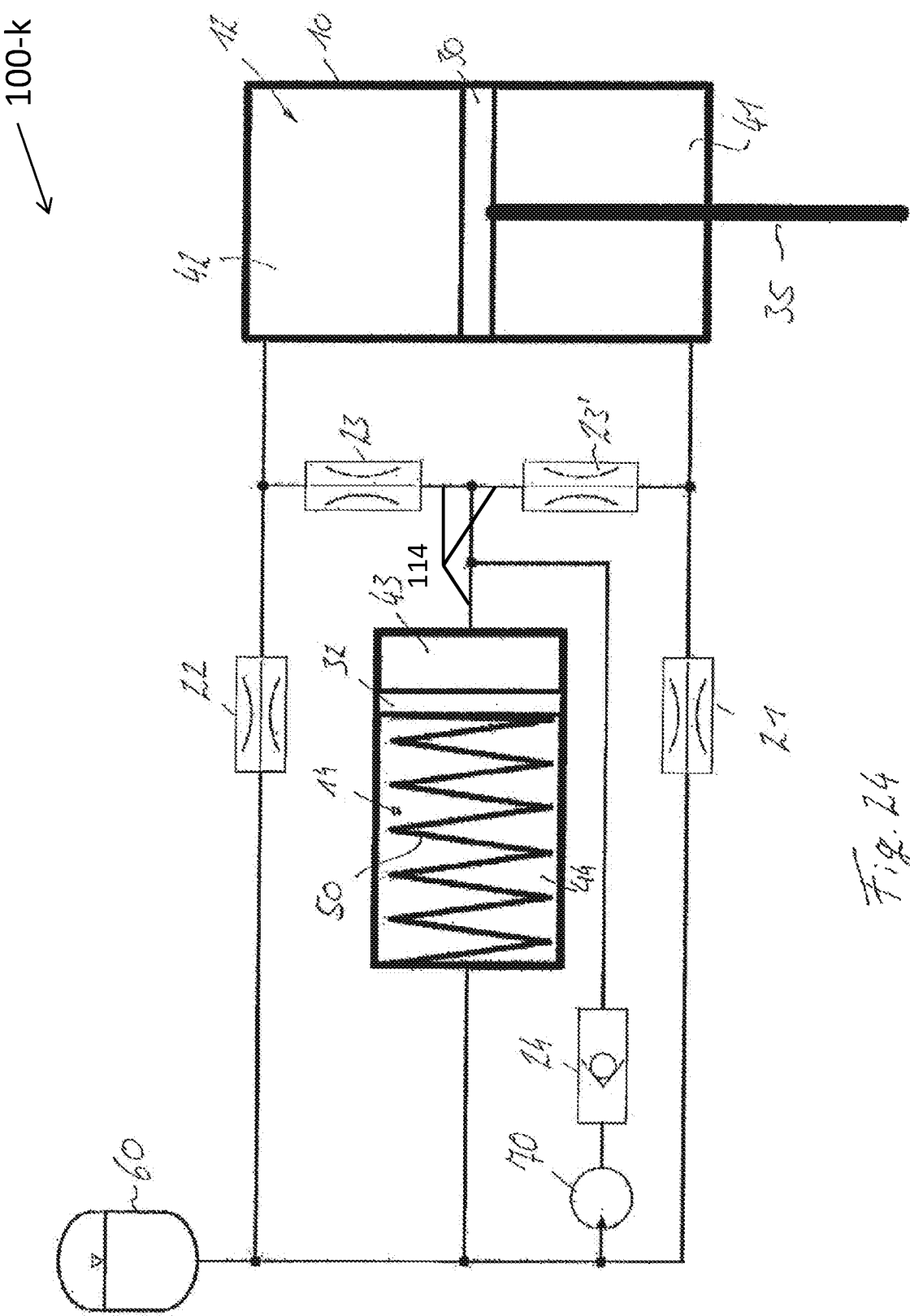
FIG. 24 shows a further embodiment of the actuator-damper unit shown in FIG. 23 with a pump.

FIG. 24 shows an alternative embodiment of FIG. 23, wherein the AD unit 100-k includes a pump 70 comprising a non-return valve 24 that is fluidically coupled to the second cylinder 14. The pump 70 may load the energy accumulator 50 independently of the first piston 30 and a movement of the piston 30 or may generate a movement of the piston 30 alone. For example, the pump 70 may provide a large quantity of energy. The pump 70 may be electric, may be driven by an electric motor, and may be coupled to a computer or an electronic control device (e.g., control device 80 shown in FIG. 2) to control the timing and quantity of energy to store or release. In addition, the actuator 50 may be actively moved to cause either a flexion or an extension, wherein the energy accumulator 50 acts as a serially elastic element.

Figure 25:
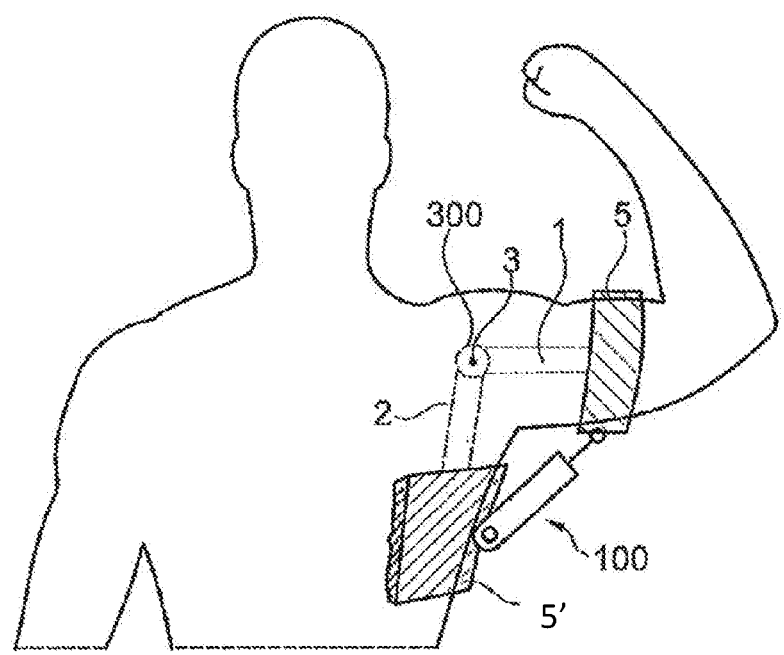
FIGS. 25 to 29b show exemplary embodiments of the actuator-damper unit according to the present disclosure.

FIG. 25 shows an embodiment of an actuator-damper unit 100 for a shoulder joint. The actuator-damper unit 100 may connect a first fastening device 5 to a second fasting device 5'. In some embodiments, the first fastening device 5 may connect to an upper part 1. The upper part 1 may connect to a lower part 2 which may connect to the second fastening device 5'. The first fastening device 5 may comprise an upper arm cuff and the second fastening device 5' may comprise a thorax support 5. The lower part 2 may pivotally couple to the upper part 1 through a joint device 300 about pivot axis 3 or multiple pivot axes, if the joint device 300 allows more than one degree of freedom or is a polycentric joint. Alternatively, more than one joint device 300 is provided to couple the upper part 1 with the lower part 2 pivotally. The upper part 1 and the lower part 2 may comprise bars of an orthosis. The two fastening devices 5, 5' may include accommodating devices for the piston rod 35 and the housing 10 such that when a user's arm moves away or toward the user's thorax by the piston rod 35 either retracting into or extending out of a housing 10. Alternatively to a coupling of the fastening devices 5 via a joint device 300 to the pivot axis 3 and the upper part 1 and the lower part 2, it is possible in some embodiments for the force retention to take place directly via the body of the patient, i.e., via the skeletal structure, and so the upper part 1 and the lower part 2 are implemented using the fastening devices 5, 5'. The force transmission from the thorax support 5' to the ground takes place either via the body of the user or via an orthosis structure, similar to that of an exoskeleton, comprising the upper body and the lower extremity.

Figure 26:
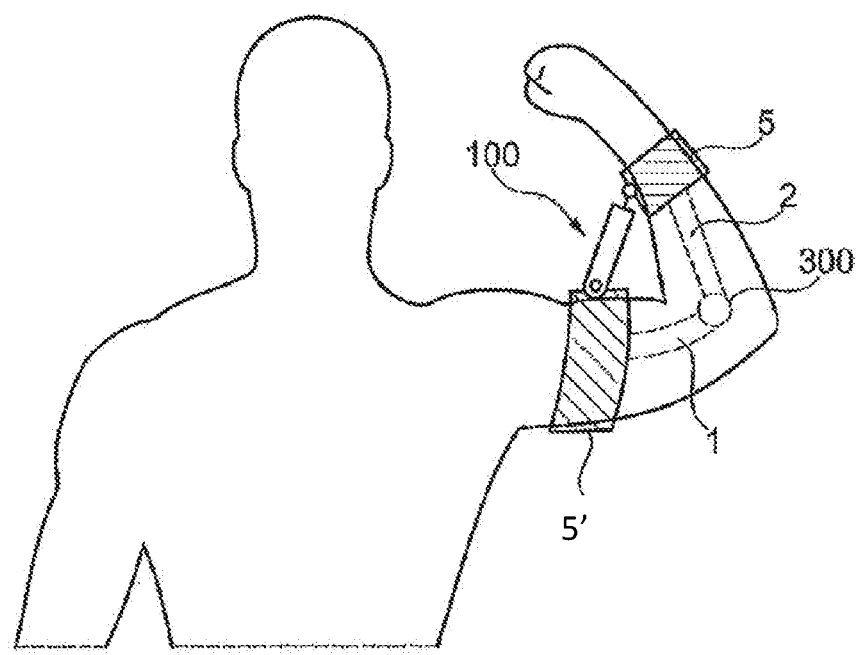

FIG. 26 shows an alternative embodiment of an actuator-damper unit 100 for an elbow joint. The actuator-damper unit 100 utilizes a first fastening device 5 and a second fastening device 5'. The first fastening device 5 may comprise a forearm support and the second fastening device 5' may comprise an upper arm support or an upper arm cuff. In one embodiment, the orthotic or prosthetic device may include only the actuator-damper unit 100 and the two fastening devices 5, 5'. In another embodiment, an upper part 1 may connect to the first fastening device 5 and a lower part 2 may connect to the second fastening device 5'.

The upper part 1 and lower part 2 may connect through a joint device 300. This may enable force retention. In some embodiments, the upper part 1 and the lower part 2 may comprise bars. The elbow device may work independently or in conjunction with a shoulder device. It is also possible to combine the embodiment according to FIG. 26 with the embodiment according to FIG. 25, and so, in addition to an assisted shoulder joint according to FIG. 25, it is also possible to obtain an assisted elbow joint. The further force introduction into the ground advantageously takes place via a further orthosis structure (not shown) or an exoskeleton.

Figure 27:
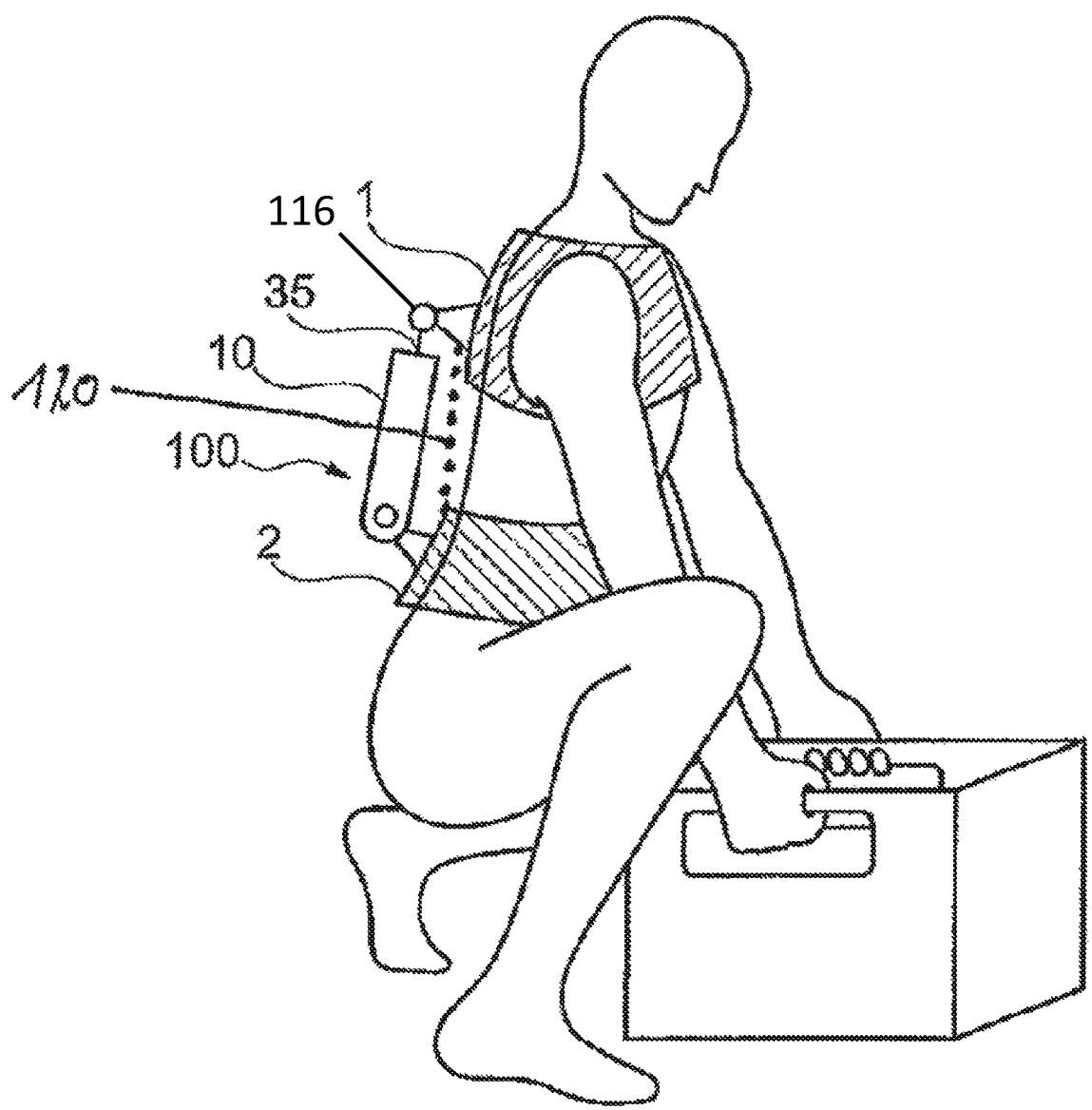

FIG. 27 shows another embodiment where the actuator-damper unit 100 assists trunk movements. The actuator-damper unit 100, more precisely the piston rod 35, is connected via a first bearing point 116 to an upper part 1 in the form of a proximal body support and via a second bearing point with the housing 10 to a lower part 2 in the form of a distal body support in the region of the lumbar spine. The piston rod 35 is connected to the upper part 1. In some embodiments, a reversed assignment is also provided and possible, and so the piston rod 35 may also be disposed on the lower part 2. In a further embodiment, a cascading of multiple actuator-damping units 100 over multiple segments along the back or the vertebral column is provided. In some embodiments, the actuator-damper unit 100 may function across multiple joints by means of two or more piston rods. A mechanical coupling 120 between the upper part 1 and the lower part 2 may provide a brace for the actuator force (e.g., represented in the figure by means of a dotted line).

Figure 28:
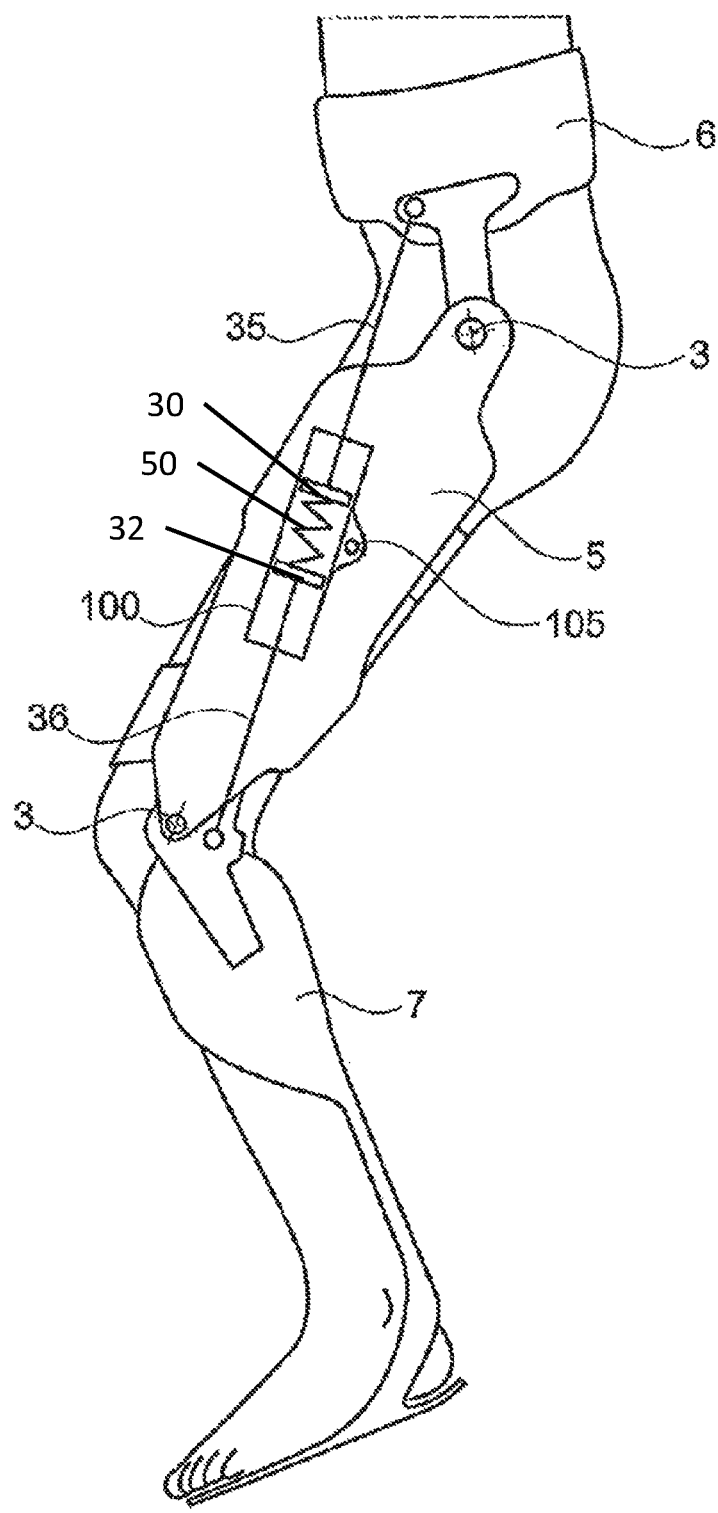

FIG. 28 shows an orthotic device in the form of an HKAFO (hip-knee-ankle-foot-orthosis). In this embodiment, an actuator-damper unit 100 may be attached to a fastening device 5 in the form of a thigh support 5. The actuator-damper unit 100 may comprise two separate pistons 30, 32 are coupled together by a spring 50 or an elastomeric element. Each piston 30, 32 may be connected to a piston rod 35, 36. The piston rod 35 may couple to a hip support 6 and the piston rod 36 may couple to a lower leg support 7. The hip support 6 may be pivotably mounted on the thigh support 5 about a joint axis 3. The rotational axis 3 may be located adjacent to or in alignment with the level of the natural hip joint axis. A pivot motion may occur when the first piston rod 35 retracts into or extends out of the housing 10. The second piston rod 36 may be mounted on the lower leg bar 7. In some embodiments, the lower leg bar 7 may include a formed foot part, the formed foot part may comprise an integrally formed elastic element which may act as a spring around the ankle joint. The lower leg bar 7 may be pivotably mounted to the thigh support 5 about a pivot axis 3 or multiple pivot axes, if the joint allows more than one degree of freedom or is a polycentric joint. This pivot axis 3 or multiple pivot axes, if the joint allows more than one degree of freedom or is a polycentric joint, may be located at a level of the natural joint axis. The orthotic device may engage across multiple joints, primarily the knee joint and the hip joint. The actuator-damper unit 100 may be rotatably mounted via a connection point 105 on the thigh support 5. The different retraction and extension movements of the piston rods 35, 36 may be effectuated by the actuation of the actuator, which may result in a pivoting of the particular components 5, 6, 7 with respect to each other. In addition, various valve switching or, in some embodiments, activating magnetic fields for magnetorheological fluids, may result in movement damping. The principle of an orthosis or prosthesis comprising an actuator which engages across multiple joints can also be applied for other body segments, in particular for the knee and ankle joints, for back segments, and for orthotic or prosthetic devices on the upper extremity.

Figure 29A:
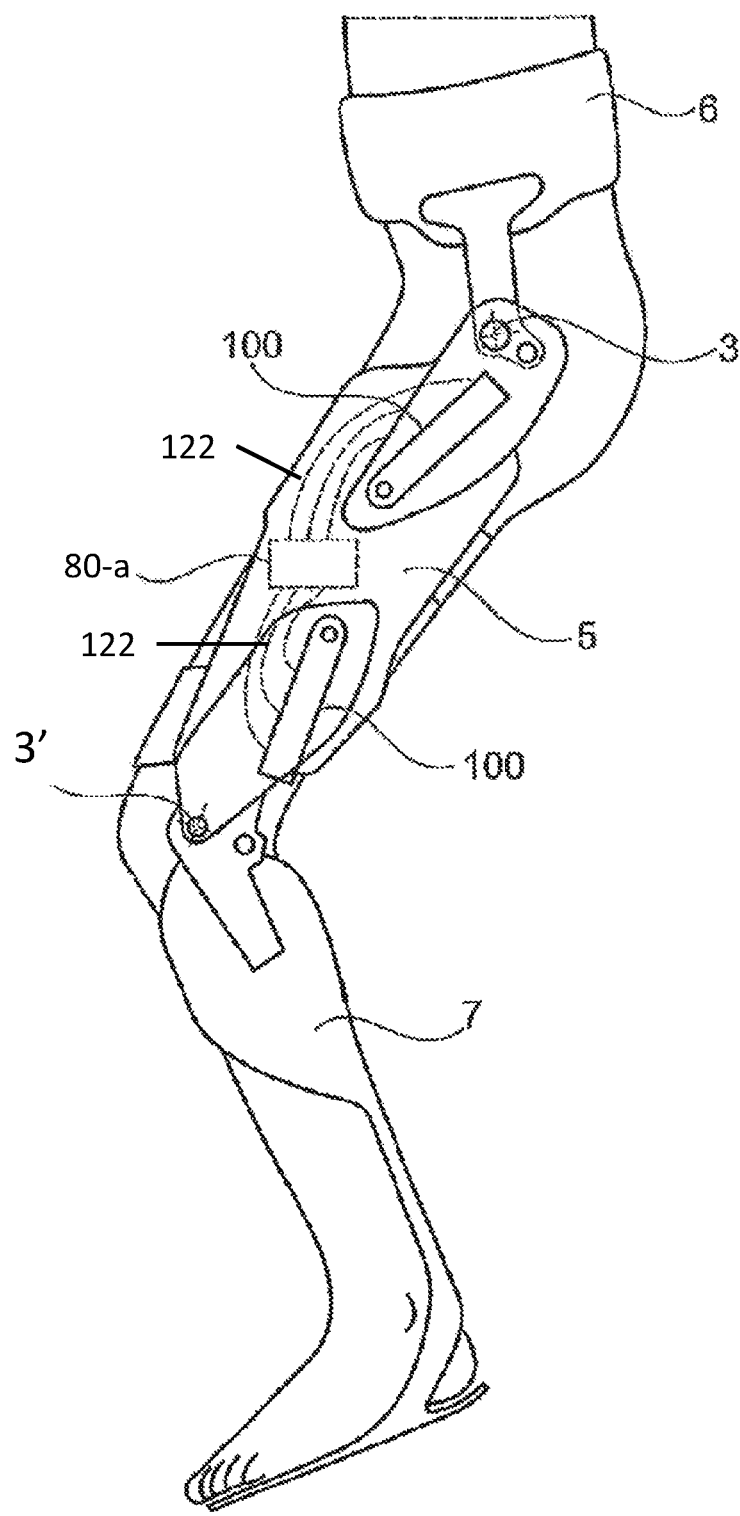

One variant of the embodiment of an orthotic device which engages across joints is represented in FIG. 29A which shows an embodiment comprising two actuator-damper units 100 attached to one thigh support 5. In some embodiments, the individual actuator-damper units 100 are hydraulically coupled. For example, in the HKAFO leg orthosis represented shown in FIG. 29A, a first actuator 100 assists movement of the thigh support 5 relative to the hip support 6 or cuff in the region of the natural hip joint, while the second actuator 100 assists the knee movement by a displacement of the lower leg bar 7 relative to the thigh support 5 about the rotational joint 3'. The two actuators 100 may be hydraulically interconnected via optional hydraulic lines 122, which are represented using dashed lines. In some embodiments, a control device 80-*a* or a valve control block may be present in the lines, wherein different interconnection variants implemented via the valve control device 80-*a* enable energy to be transferred between the particular actuators 100. Such a coupling is also possible between further actuators at other points, or at the knee or the foot or between the both legs. The control device 80-*a* can function in a computer-assisted manner, a manual manner, or a hybrid computer/manual manner, and, in some embodiments, can process sensor signals.

Figure 29B:
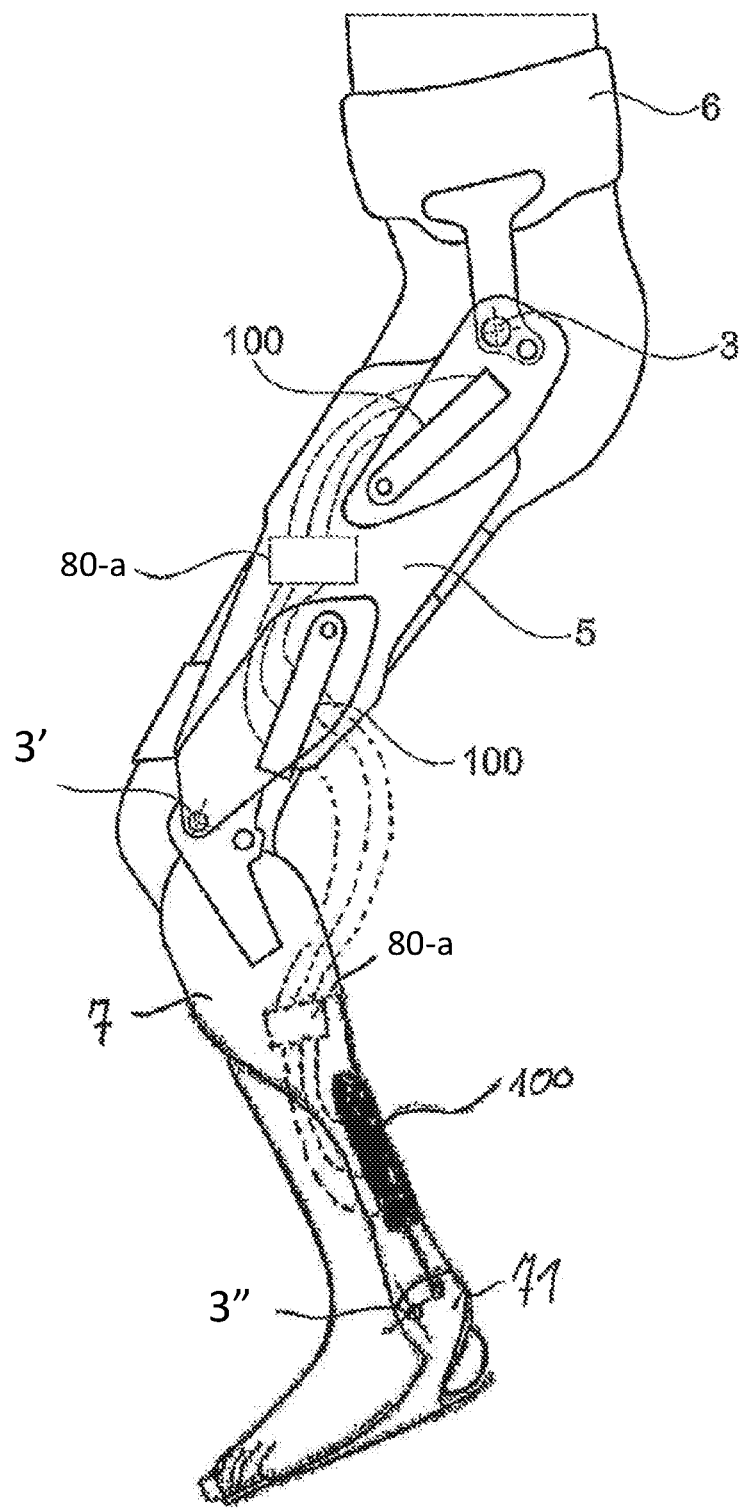

FIG. 29B is an alternative embodiment of FIG. 29 comprising a foot part 71 mounted on the lower leg bar 7. The foot part 71 may be pivotably movable about a pivot axis 3" via a lower AD unit 100, in the direction of a plantar flexion and a dorsiflexion. The lower AD unit 100 may be mounted on the lower leg support 7 which may be controlled by a separate, lower control device 80-*a*. In some embodiments, the control device 80-*a* may be mounted on the thigh support 5. The AD units 100 may be hydraulically coupled to transmit force beyond the individual AD unit 100. The hydraulic coupling may reduce the number of pumps utilized. As shown in FIG. 29b, the foot part is actuated or the pivoting thereof relative to the lower leg support 7 is damped or blocked.

Figure 30A:
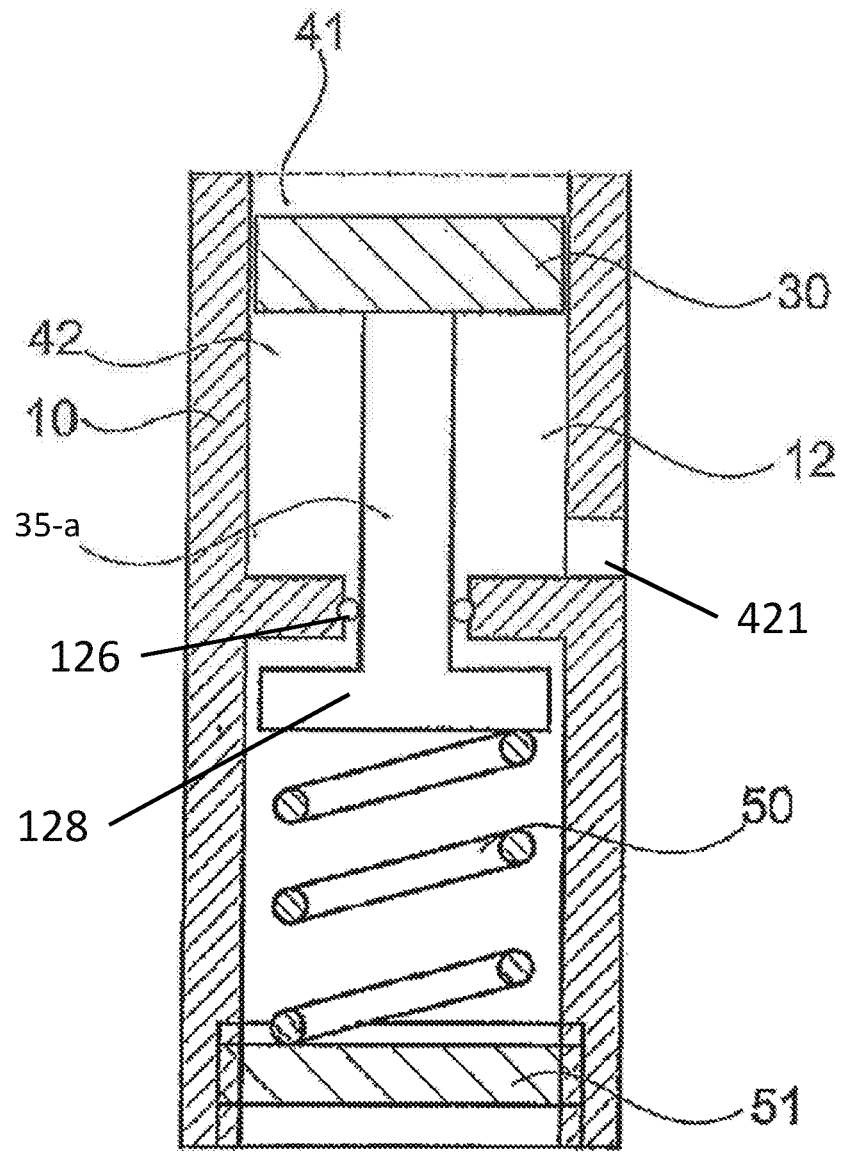
FIG. 30A shows a schematic representation of a piston comprising an adjustable energy accumulator.

FIG. 30A shows an alternative embodiment for an energy accumulator 50. In this embodiment, the spring of the energy accumulator 50 may be located external to the fluid flow and, in particular, outside a hydraulic fluid flow. For example, the piston rod 35 may be sealed with respect to the energy accumulator 50 in the form of the spring by means of a sealing ring 126, and so the spring 50 does not come into contact with the hydraulic fluid, in particular hydraulic oil. In such an embodiment, the energy accumulator 50 may comprise a material incompatible with a hydraulic fluid. In addition, the energy accumulator 50 may be easily replaced, without the need to open a fluid chamber 42 (e.g., an oil circuit). Instead, to replace the energy accumulator 50, a retaining disk 51 may be removed from the housing 10, and allow the spring or the energy accumulator 50 to be easily removed. The disk 51 also enables a preload of the energy accumulator 50 to be altered or changed. For example, as the disk 51 is screwed into the housing 10, the final position of the disk 51 may determine a preload on the energy accumulator 50. A corresponding thread may be included in the embodiment of FIG. 30A.

The oil pressure of the fluid chambers 42, 41 act on the piston 30 which in turn compresses the energy accumulator 50 through a plunger 128 on an end of the piston rod 35-*a*. The oil from the second fluid chamber 42 emerges from the low pressure chamber via an opening 421 and enters the low pressure circuit where a compensating volume is located. A compensating volume may absorb the quantity of oil displaced due to the volume differences of chambers 41 and 42 caused by the piston rod 35-*a*. A stiffness of the energy accumulator 50 or springs used in combination with or in place of the energy accumulator 50 can adjust to different patient needs. In a further embodiment, the adjusting screw or adjusting disk 51 may be altered to adapt to patient needs.

Figure 30B:
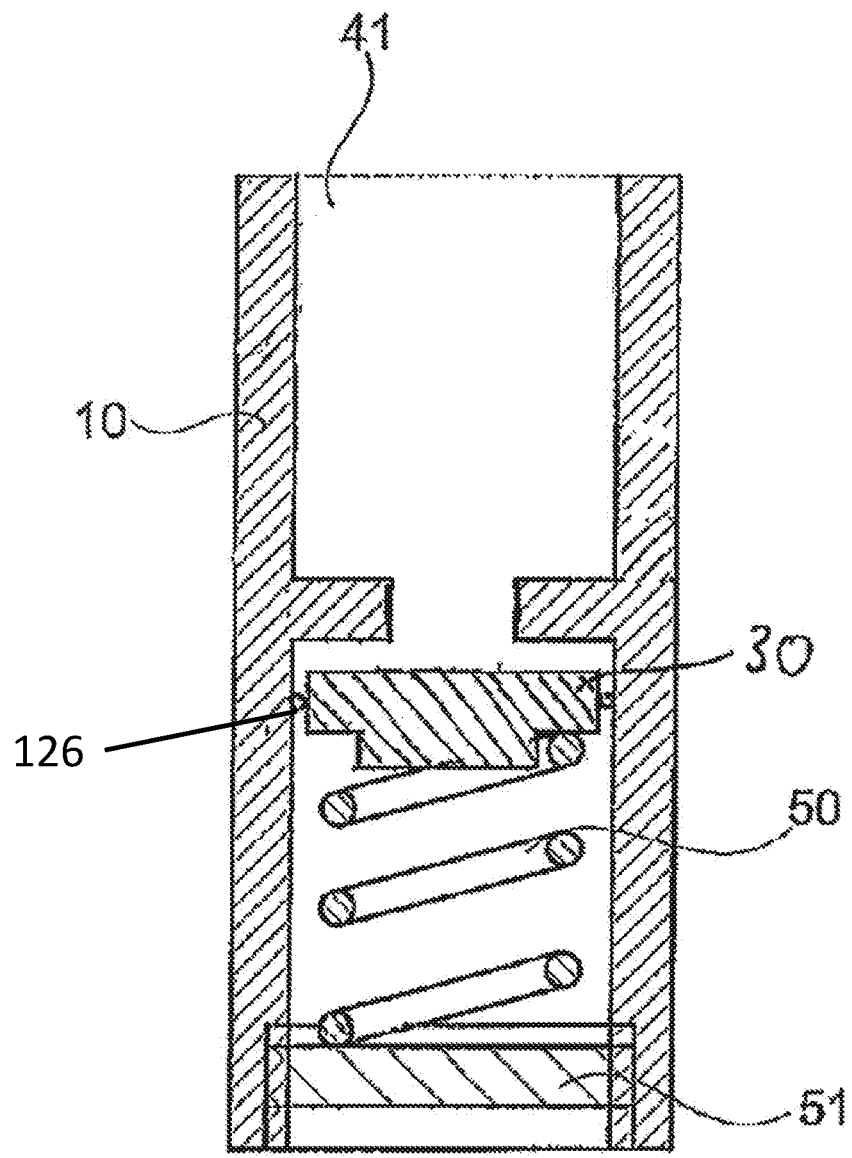
FIG. 30B shows a further embodiment of the piston comprising an adjustable energy accumulator of FIG. 30A.

FIG. 30B shows an embodiment with the piston 30 mounted in the housing 10 to counter a spring force applied by the energy accumulator 50. The piston 30 is sealed with respect to the housing inner wall, for example with a sealing ring 126. For example, the fluid from the chamber 41 may directly compress the spring 50 pressing on the piston. This may eliminate the piston rod 35, plunger, and/or an outlet channel for fluid displaced from the lower chamber 42.

Figure 31:
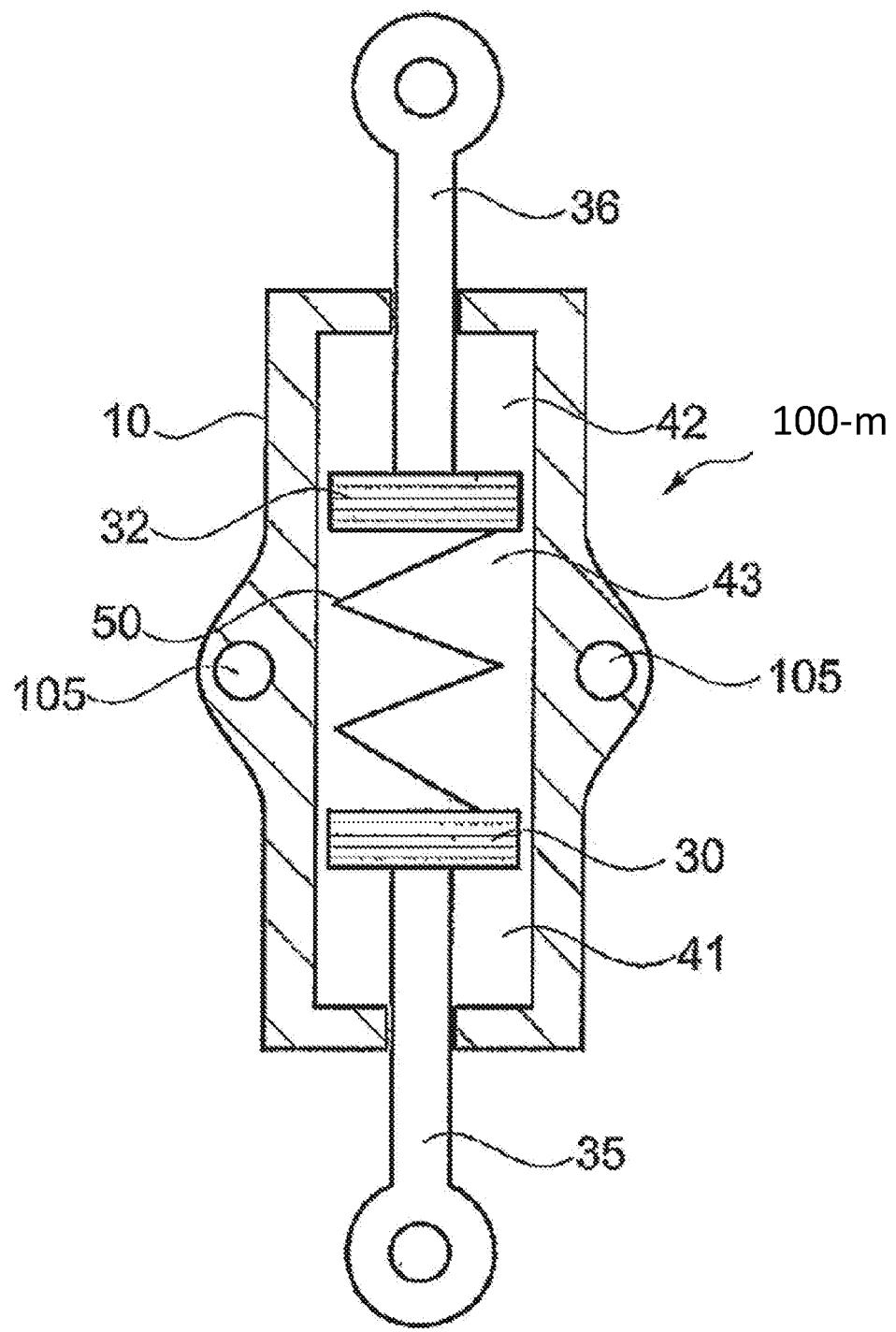
FIG. 31 shows a sectional representation of an exemplary actuator-damper unit comprising two piston rods.

FIG. 31 is another embodiment of an actuator-damper unit 100-*m* comprising two pistons 30, 32 forming three fluid chambers 41, 42, 43. A spring, as the energy accumulator 50, is disposed between the two pistons 30, 32. A hydraulic interconnection is not shown, but may be present in this embodiment. Two piston rods 35, 36 may attach to prosthesis or orthosis structural parts through connection points on their outer ends. The housing 10 may be fastened to an orthosis structure or prosthesis structure through connection points 105. In this embodiment, the actuator 50 may engage across multiple joints as described with reference to FIG. 28. In another embodiment, if only the housing 10 and one of the piston rods 35, 36 are coupled to the orthosis structural parts or prosthesis structural parts, the actuator-damper unit 100-*m* may only act on this connection between the two structural parts. The second piston rod 36 may not connect to a structural component and is used only for volume compensation.

Figure 32:
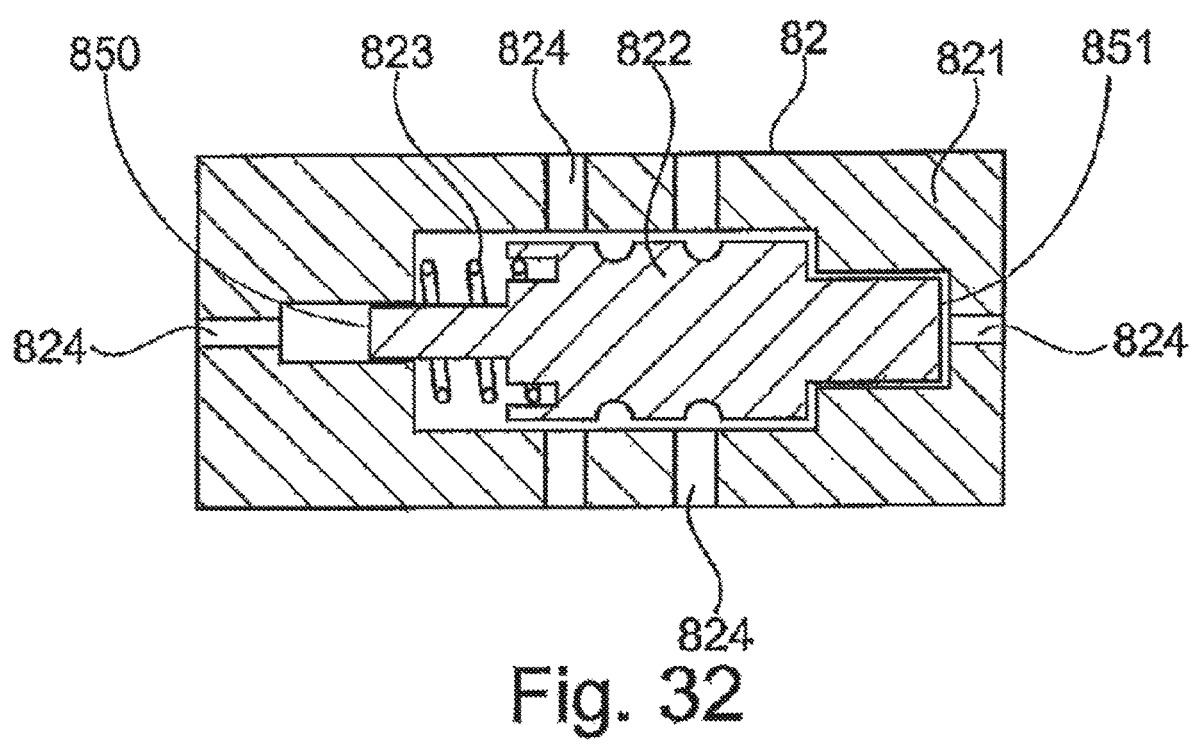
FIG. 32 shows a sectional representation of an exemplary mechanical pressure control valve.

FIG. 32 shows a schematic sectional illustration of a mechanical pressure control valve 82 for a pressure accumulator comprising a valve body 821 and a switching element 822. The switching element 822 may be movably mounted in the valve body 821 and may be initially positioned by a spring 823. Multiple connection bores 824 for a pressure fluid, in particular a hydraulic fluid, are disposed in the valve body 821 and are connected to fluid lines. A sizing of cross-sections 850, 851 may implement a hysteresis in the switching function or, in some embodiments, the effect of the force of the return spring may be partially compensated for.

Figure 33:
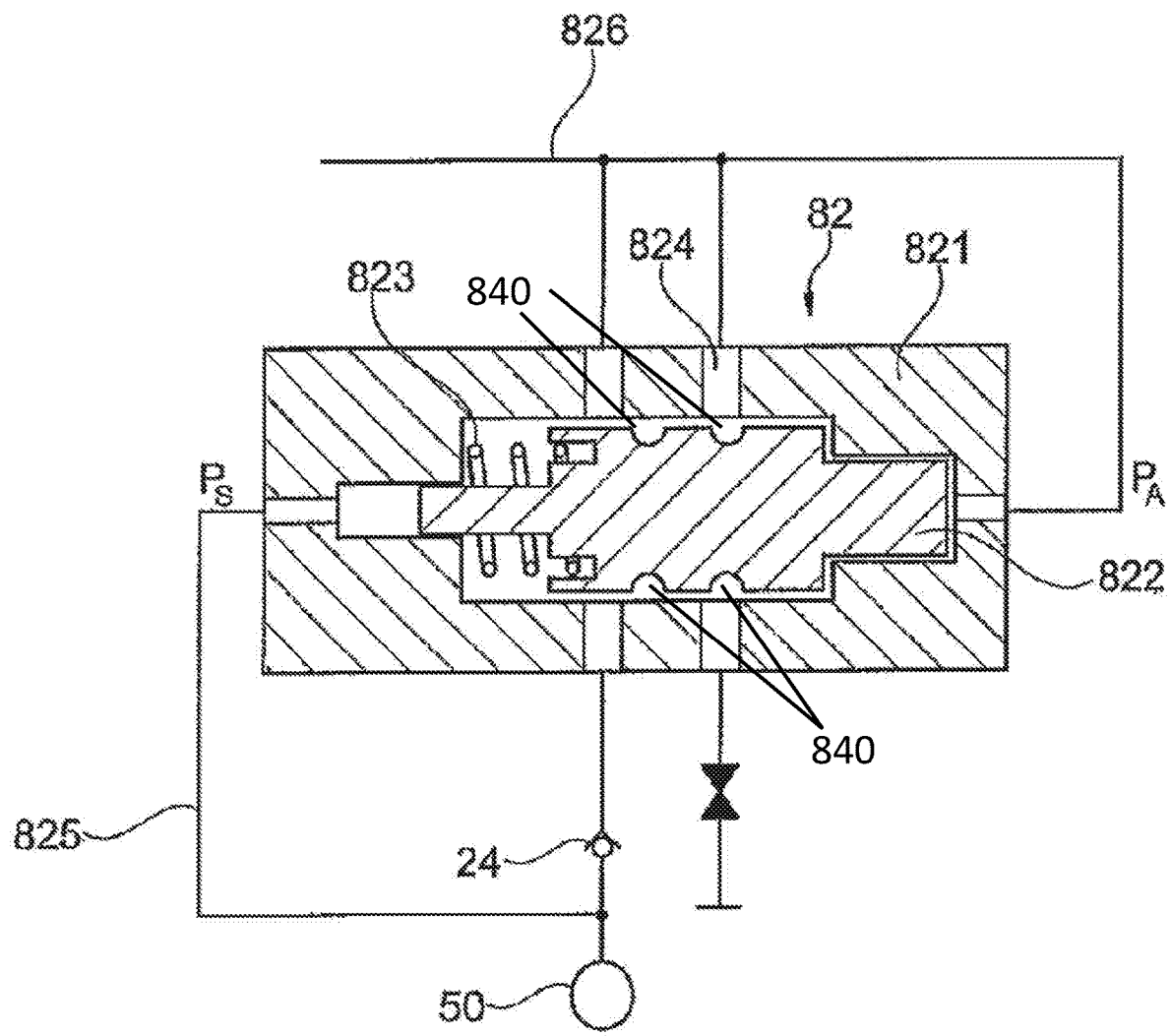
FIG. 33 shows a schematic representation of an installation situation of the exemplary pressure control valve.

FIG. 33 is a schematic of the hydraulic interconnection of the pressure control valve 82. The pressure control valve may store energy and or pressure. The movable switching element 822 is acted upon by a fluid pressure $p_S$ from the pressure accumulator 50 via a pressure line 825. The fluid pressure $p_S$ supports the pressure spring 823 and presses the switching element 822 into an initial position shown. If hydraulic fluid from the actuator-damper unit (not shown) is fed to the pressure control valve 82 via a working pressure line 826, a working pressure $p_A$ is present at the switching element 822. The working pressure $p_A$ acts against the accumulator pressure $p_S$ and against the spring force of the spring 823. Peripheral grooves 840 are disposed within the movable switching element 822, which, in the starting position, allow a passage from the working pressure side to a low pressure side. If the working pressure $p_A$ is greater than the accumulator pressure $p_S$, the switching element 822 is displaced toward the left. In this configuration, the left groove 840 within the switching element 822 is oriented toward the left bores within the valve body 821. A flow connection therefore results from the working pressure side to the pressure accumulator 50, and so the working fluid does not reach the low pressure side $p_L$, but rather loads the pressure accumulator 50. The non-return valve 24 prevents a backflow directly through the fluidic connection. If the accumulator pressure $p_S$ becomes too great, the switching element 822 is displaced to the right again, and so the fluid can flow through the pressure control valve 82 without a branching off of a pressure for the pressure accumulator 50. In this embodiment, the pressure control valve 82 does not require electronic control and may be operated without an external energy supply.

FIGS. 34 to 39 represent another embodiment of an actuator-damper unit 100-*n*. In this embodiment, the actuator-damper unit 100-*n* comprises a housing 10 forming a cylinder 12. A first, working, piston 30 is displaceably mounted in the cylinder 12. The piston 30 is coupled or at least may be coupled to a prosthetic or orthotic device (not shown) via a piston rod 35 which extends out of the housing 10; the housing 10 may also be attached to another part of the orthotic or prosthetic device. Two blocking walls 90 are disposed within the cylinder 12 and subdivide the cylinder 12 into a total of three chambers, namely into a middle main chamber and two outer secondary chambers; a piston 30, 32 and coupling device 31 are movably mounted in each of these chambers. The piston 30 connected to the piston rod 35 is disposed in the middle chamber and subdivides this main chamber into two fluid chambers 41, 42. Spring-loaded pistons 31, 32, which, in the exemplary embodiment represented, are disposed on the side of the particular blocking wall 90 facing the main chamber, are disposed in the secondary chambers, which are separated by the blocking walls 90. The springs 50, which are supported against the particular piston 31, 32 and against the outer cylinder wall, are disposed on the side facing away from the middle working piston 30 which is connected to the piston rod 35.

A control valve 21, 22 and a non-return valve 24 are disposed within each of the blocking walls 90.

The spring pistons 31, 32 subdivide the particular secondary chamber into a fluid-filled chamber 43, 44, which may be filled with the hydraulic fluid, and a fluid-free chamber 43', 44'. The energy accumulator 50, which is in the form of a spring or an elastomeric element in the exemplary embodiment shown, is disposed within the fluid-free chambers 43', 44'. The piston rod 35 extends through the piston 31 and extends outside of the housing 10.

The fluid chambers 41, 42, separated by the working piston 30, are hydraulically coupled to each other via fluid lines 20. Two control valves 23, 23' and contradirectionally oriented non-return valves 24 are disposed in the fluid lines 20. The fluid-filled secondary chambers 43, 44 are also connected to each other via a hydraulic line comprising contradirectionally oriented non-return valves 24. The connection line of the secondary chambers 43, 44 is also coupled to the connection lines between the first fluid chambers 41, 42 via a connection line between the two non-return valves 24.

The AD unit 100-*n* is therefore a combination of three movable pistons 30, 31, 32 in three chambers and two energy accumulators 50. The energy accumulators 50 are located on the outer sides of the spring pistons 31, 32 and do not contact any fluid. A passive displacement of the working piston 30 due to the change in the movement resistances or drives takes place internally. In some embodiments, the passages through the blocking walls 90 using the control valves 21, 22 or the non-return valves 24 may be disposed in the blocking walls 90. In other embodiments, the passages may be ducts which have appropriate valves and are routed along the housing 10 on the outside of the cylinder 12. The spring pistons 31, 32 are removed from the circuit as a damping effect is achieved through operation of the control valves 21, and the non-return valves 24. The passive displacement of the working piston 30 may also be blocked by way of the two-way interconnection of the hydraulic line which is disposed outside the housing 10 and extends in parallel to the working piston 30.

A volumetric compensation of the hydraulic fluid takes place via the springs when a hydraulic compensation blocked. Hydraulic compensation may be blocked when the external control valves 23, 23' and only the passages to the spring pistons 50 via the valves 21, 22 are open. The volume of the fluid-filled secondary chambers 43, 44 may change depending on the position of the working piston 30. When an active displacement is blocked and only a passive displacement occurs via the external valves 23, 23', 24, a volumetric compensation should be present. In this example, the appropriate control valve 23, 23' would need to be opened.

Figure 34:
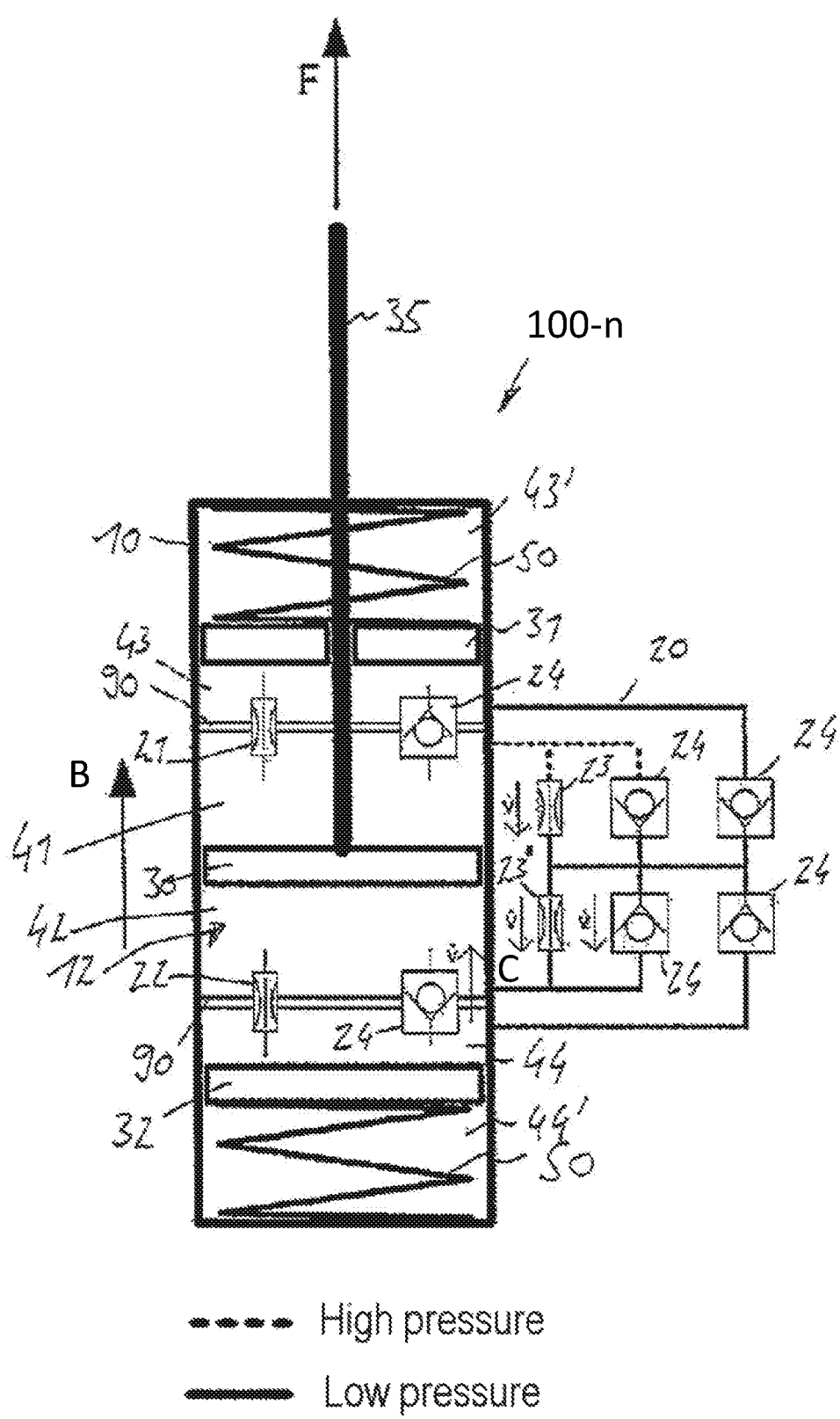
FIGS. 34 to 39 show schematic sectional representations of an embodiment of an actuator-damper unit comprising three pistons in a cylinder which is subdivided by two blocking walls into three hydraulically interconnected chambers.

In FIG. 34, the working piston 30 is moved in the direction B during an extension movement of the piston rod 35. As a result, the pressure in the upper fluid chamber 41 is increased and high pressure fluid flows against the first non-return valve 24 and through the first control valve 23, as indicated by the arrow C, through the second control valve 23' and into the lower fluid chamber 42. Additionally, the lower energy accumulator 50 may release energy as it expands, thereby forcing hydraulic fluid through the lower non-return valve 24 into the lower fluid chamber 42. The control valves 21, 22 are closed, thereby resulting in an extension movement, which has been damped by the valves 23, 23'.

Figure 35:
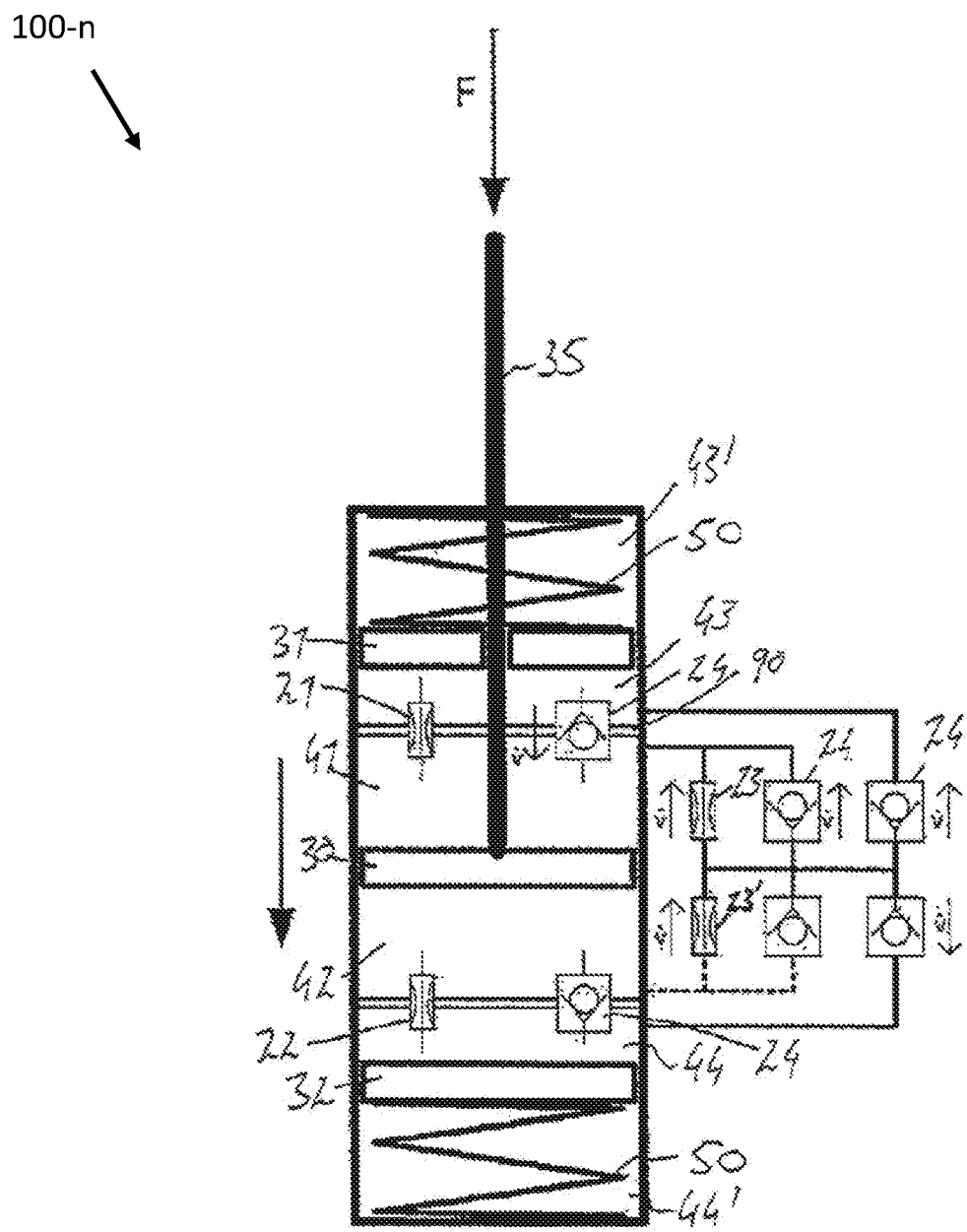

During an opposite, retraction movement, as shown in FIG. 35, the control valves 21, 22 in the blocking walls 90 are still closed, while the control valves 23, 23' in the external hydraulic circuit are open. When the piston rod 35 retracts, for example during a flexion, hydraulic fluid flows from the lower fluid chamber 42 into the upper fluid chambers 41, 43. For example, fluid flows through the high pressure line and the lower control valve 23', the upper control valve 23, and the two non-return valves 24, into the upper fluid chamber 41 of the working piston 30 and into the upper fluid chamber 43 of the spring piston 31. Pressure within the connection line between the non-return valves 24, which may connect the fluid chambers 43, 44 of the spring pistons 31, 32 to each other, causes simultaneous fluid flow into the fluid chamber of the lower spring piston 32. The upper energy accumulator 50 may expand as it is disposed on the low pressure side. Accordingly, hydraulic fluid can flow out of the upper fluid chamber 43, through the non-return valve 24, and into the upper fluid chamber 41 of the working piston 30.

Figure 36:
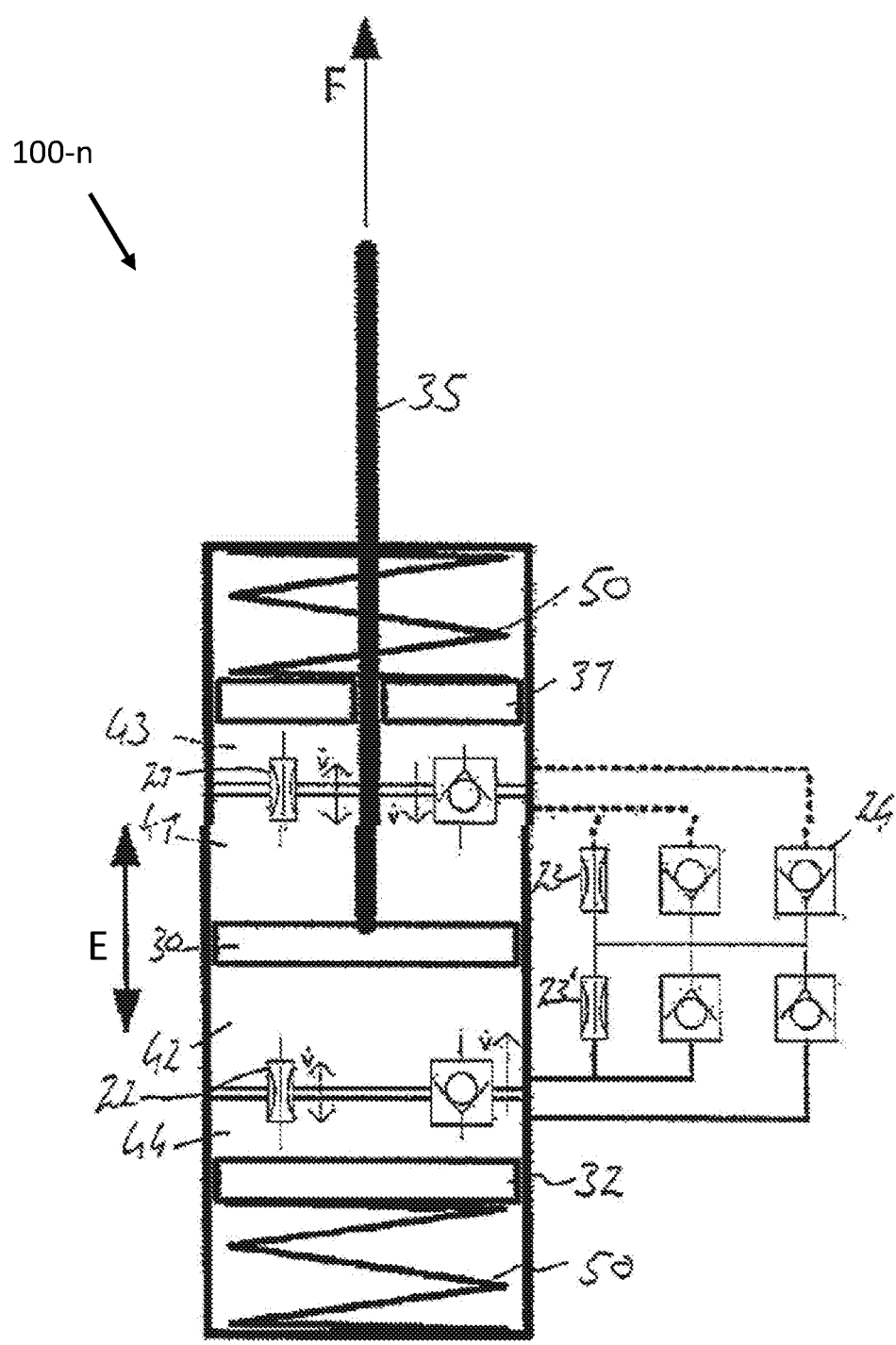

In FIG. 36, the spring valves 21, 22 are open, while the external control valves 23, 23' are closed. The opened spring valves 21, 22 allow a back and forth movement of the piston 30 in the direction of arrow E, since the springs 50 in the secondary chambers expand and/or compress. The outer flow path is blocked creating a possible volume exchange between only the particular adjacent fluid chambers 41, 43 and 42, 44 through the spring valves 21, 22 and the non-return valves 24.

Figure 37:
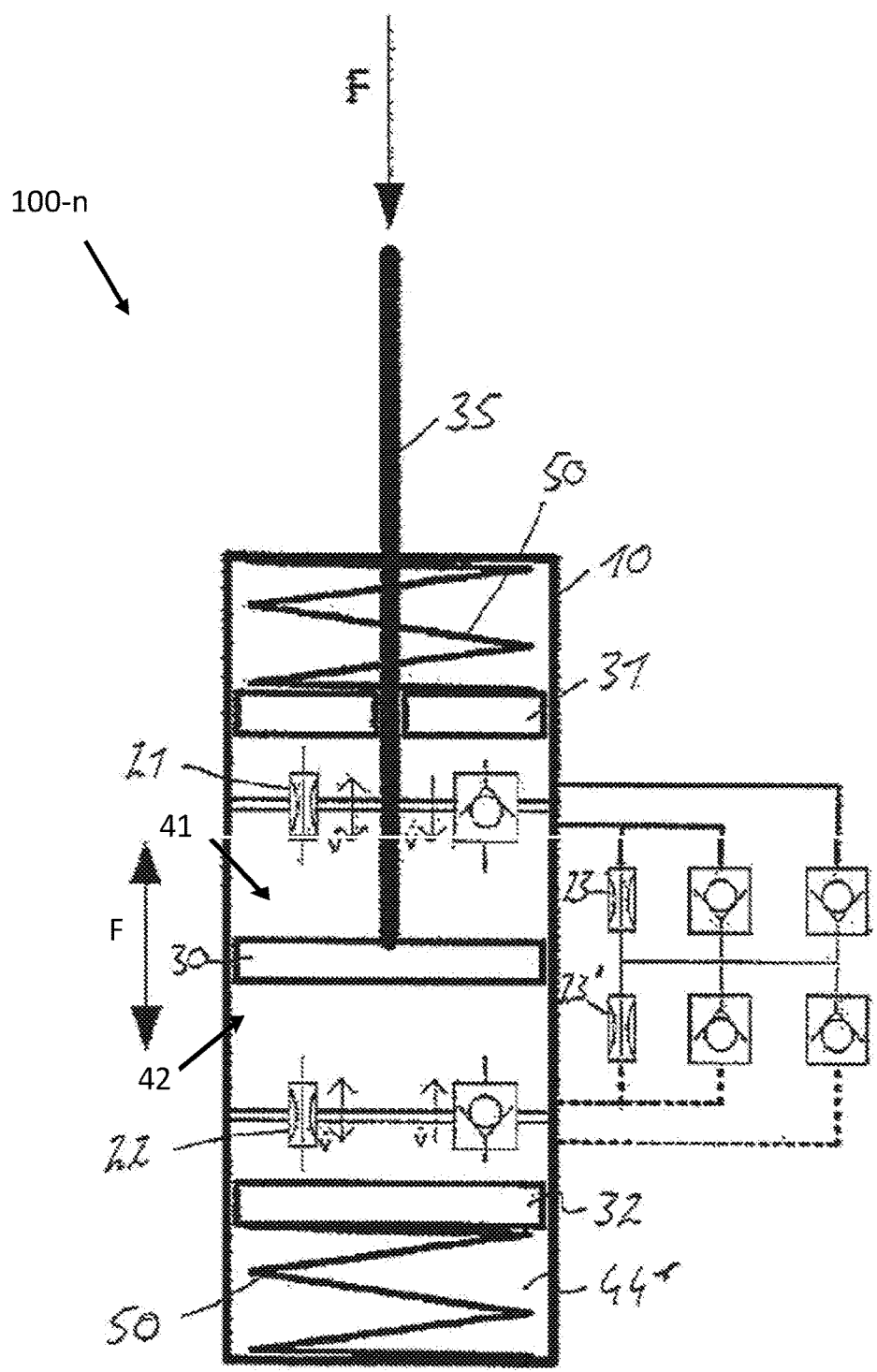

FIG. 37 shows a configuration wherein the valves are switched in a manner analogous to that from FIG. 36 and a pressure force is applied onto the piston rod 35 and the working piston 30 is pressed downward. The high pressure side is therefore under the working piston 30 in fluid chamber 42. When force is applied in the direction of arrow F on the piston rod 35, a deflection of the lower spring 50 occurs during a retraction of the piston rod 35, for example during a flexion. This may result in a release of energy from the upper energy accumulator 50. The energy accumulators 50 therefore behave in the reversed manner during a reversed movement, i.e., during an extension of the piston rod or during an extension movement, as shown in FIG. 36.

Figure 38:
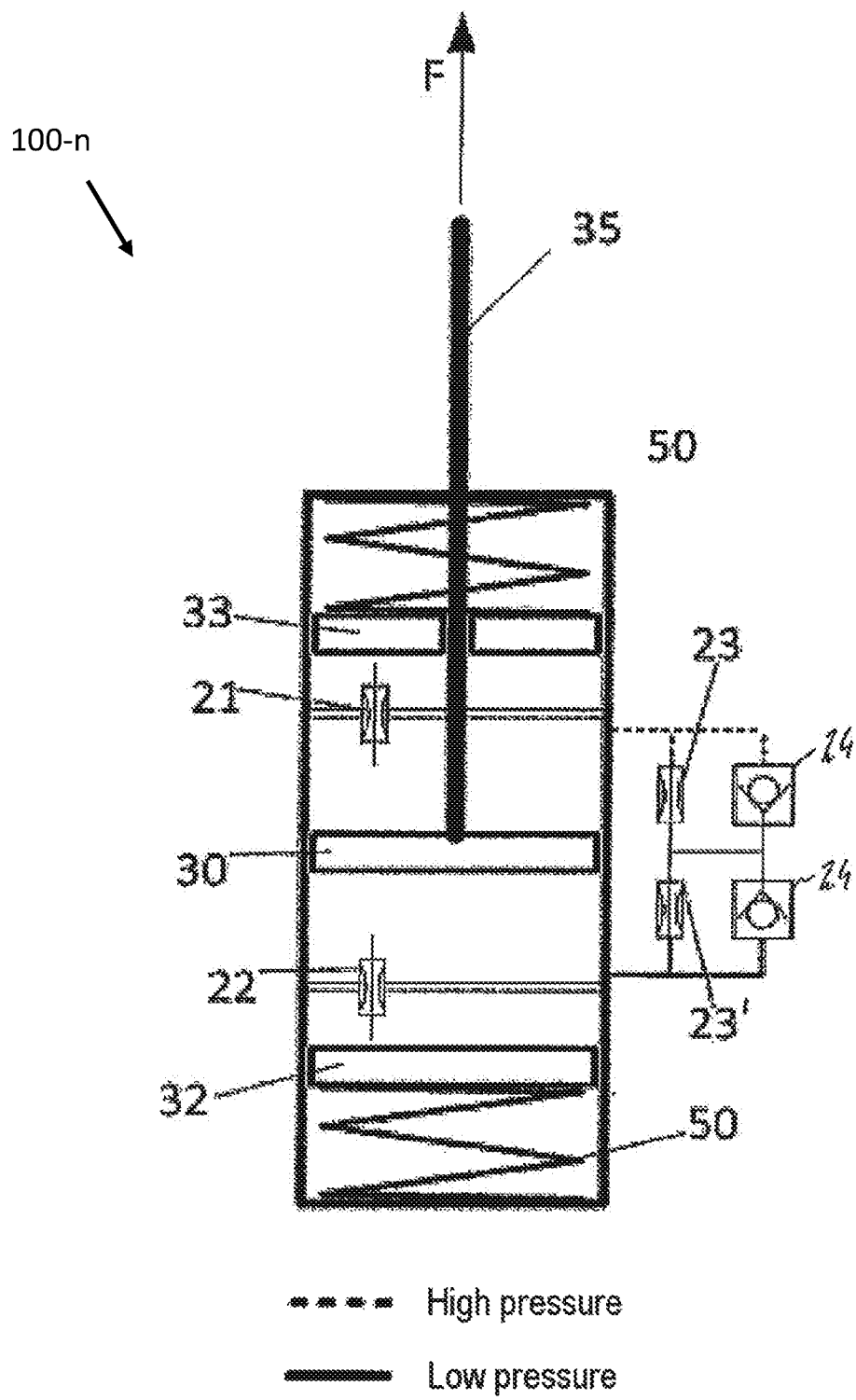
Figure 39:
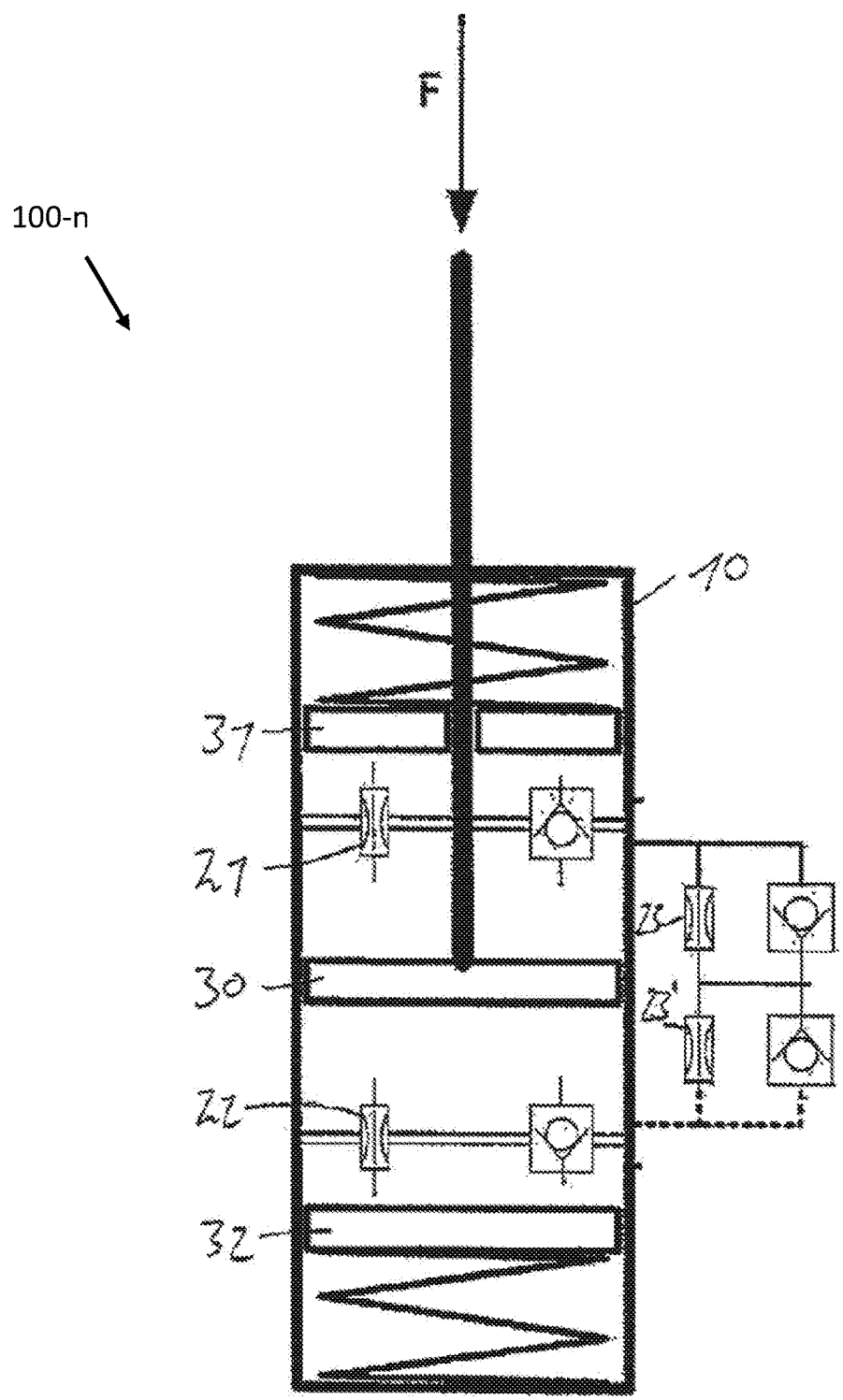

FIG. 38 shows the situation in which all valves 21, 22, 23, 23' are closed. A movement of the working piston 30 is also blocked upon application of a pulling force onto the piston rod 35; the same applies for the reversed force application, as shown in FIG. 39.

Figure 40:
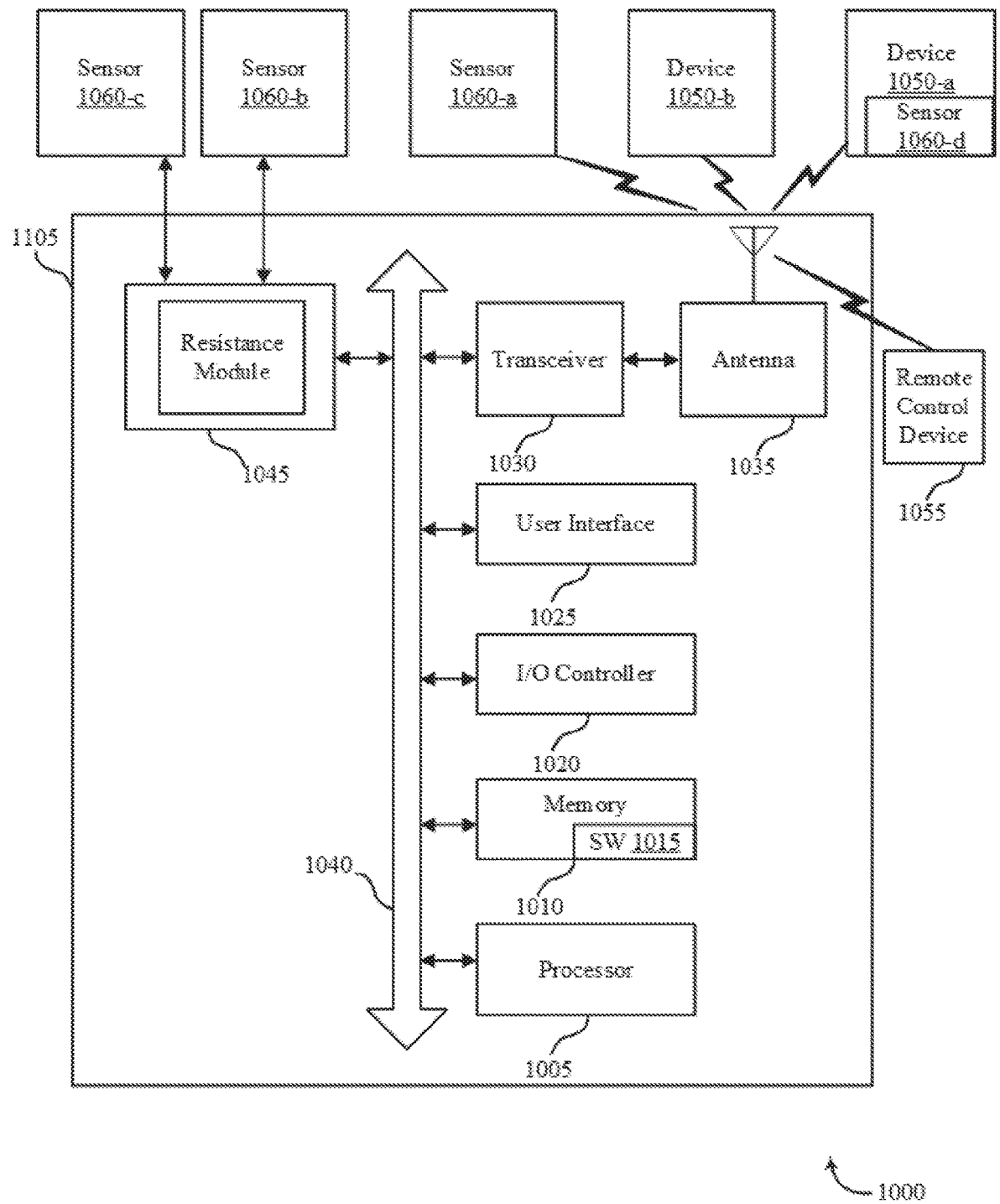
FIG. 40 shows schematically a control device for use with the orthotic and prosthetic devices of FIGS. 1-39.

FIG. 40 shows a system 1000 for use with or representative of certain aspects of the devices shown in FIGS. 1-39. System 1000 may include a control panel 1105. Control panel 1105 may be equivalent at least in part to the control device 80 described above. Control panel 1105 may include flow module 1045. The flow module 1045 may relate to certain operational features of the devices described with reference to FIGS. 1-39, such as control and/or operation of various valves. The flow module 1045 may provide communications with one or more sensors 1060 directly or via other communication components, such as a transceiver 1030 and/or antenna 1035. The sensors 1060 may represent one or more of the sensors 85 and/or 997-999 described above. The flow module 1045 may perform or control various operations associated with, for example, the control valves 21-23, the non-return valve 24, the 3-way valves 25-27, the auxiliary valves 21'-23', and the pressure control valve 82, and other components of the actuator-damper units 100, as described above with reference to FIGS. 1-39.

Control panel 1105 may also include a processor module 1005, and memory 1010 (including software/firmware code (SW) 1015), an input/output controller module 1020, a user interface module 1025, a transceiver module 1030, and one or more antennas 1035 each of which may communicate, directly or indirectly, with one another (e.g., via one or more buses 1040). The transceiver module 1030 may communicate bi-directionally, via the one or more antennas 1035, wired links, and/or wireless links, with one or more networks or remote devices. For example, the transceiver module 1030 may communicate bi-directionally with one or more of device 1050-a, device 1050-b, remote control device 1055, and/or sensors 1060-a, 1060-d. The devices 1050-a, 1050-b may be components of the actuator-damper units 100, or other devices in communication with the actuator-damper unit 100. The transceiver module 1030 may include a modem to modulate the packets and provide the modulated packets to the one or more antennas 1035 for transmission, and to demodulate packets received from the one or more antennas 1035. In some embodiments (not shown) the transceiver may be communicate bi-directionally with one or more of device 1050-a, device 1050-b, remote control device 1055, and/or sensors 1060-a, 1060-d through a hardwired connection without necessarily using antenna 1035. While a control panel or a control device (e.g., 1105) may include a single antenna 1035, the control panel or the control device may also have multiple antennas 1035 capable of concurrently transmitting or receiving multiple wired and/or wireless transmissions. In some embodiments, one element of control panel 1105 (e.g., one or more antennas 1035, transceiver module 1030, etc.) may provide a connection using wireless techniques, including digital cellular telephone connection, Cellular Digital Packet Data (CDPD) connection, digital satellite data connection, and/or another connection.

The signals associated with system 1000 may include wireless communication signals such as radio frequency, electromagnetics, local area network (LAN), wide area network (WAN), virtual private network (VPN), wireless network (using 802.11, for example), 345 MHz, Z-WAVE®, cellular network (using 3G and/or LTE, for example), and/or other signals. The one or more antennas 1035 and/or transceiver module 1030 may include or be related to, but are not limited to, WWAN (GSM, CDMA, and WCDMA), WLAN (including BLUETOOTH® and Wi-Fi), WMAN (WiMAX), antennas for mobile communications, antennas for Wireless Personal Area Network (WPAN) applications (including RFID and UWB). In some embodiments, each antenna 1035 may receive signals or information specific and/or exclusive to itself. In other embodiments, each antenna 1035 may receive signals or information not specific or exclusive to itself.

In some embodiments, one or more sensor units 1060 (e.g., angle, velocity, acceleration, force, temperature, etc.) may connect to some element of system 1000 via a network using one or more wired and/or wireless connections. In some embodiments, the user interface module 1025 may include an audio device, such as an external speaker system, an external display device such as a display screen, vibration feedback, and/or an input device (e.g., remote control device interfaced with the user interface module 1025 directly and/or through I/O controller module 1020).

One or more buses 1040 may allow data communication between one or more elements of control panel 1105 (e.g., processor module 1005, memory 1010, I/O controller module 1020, user interface module 1025, etc.).

The memory 1010 may include random access memory (RAM), read only memory (ROM), flash RAM, and/or other types. The memory 1010 may store computer-readable, computer-executable software/firmware code 1015 including instructions that, when executed, cause the processor module 1005 to perform various functions described in this disclosure (e.g., initiating an adjustment of a damping system, etc.). Alternatively, the software/firmware code 1015 may not be directly executable by the processor module 1005 but may cause a computer (e.g., when compiled and executed) to perform functions described herein. The processor module 1005 may include an intelligent hardware device, e.g., a central processing unit (CPU), a microcontroller, an application-specific integrated circuit (ASIC), etc.

In some embodiments, the memory 1010 can contain, among other things, the Basic Input-Output system (BIOS) which may control basic hardware and/or software operation such as the interaction with peripheral components or devices. For example, control strategies for the resistance module 1045, and other modules and operational components of the control panel 1105 used to implement the present systems and methods may be stored within the system memory 1010. Applications resident with system 1000 are generally stored on and accessed via a non-transitory computer readable medium, such as a hard disk drive, a solid state drive (SSD) or another storage medium. Additionally, applications can be in the form of electronic signals modulated in accordance with the application and data communication technology when accessed via a network interface (e.g., transceiver module 1030, one or more antennas 1035, etc.).

Many other devices and/or subsystems may be connected to one or may be included as one or more elements of system 1000. All of the elements shown in FIG. 40 need not be present to practice the present systems and methods. The devices and subsystems can be interconnected in different ways from that shown in FIG. 40. In some embodiments, an aspect of some operation of a system, such as that shown in FIG. 40, may be readily known in the art and are not discussed in detail in this application. Code to implement the present disclosure can be stored in a non-transitory computer-readable medium such as one or more of system memory 1010 or other memory. The operating system provided on I/O controller module 1020 may be iOS®, ANDROID®, MS-DOS®, MS-WINDOWS®, OS/2®, UNIX®, LINUX®, or another known operating system, e.g. real time operating systems RTOS.

The transceiver module 1030 may include a modem configured to modulate the packets and provide the modulated packets to the antennas 1035 for transmission and/or to demodulate packets received from the antennas 1035. While the control panel or control device (e.g., 1105) may include a single antenna 1035, the control panel or control device (e.g., 1105) may have multiple antennas 1035 capable of concurrently transmitting and/or receiving multiple wireless transmissions.

Figure 41:
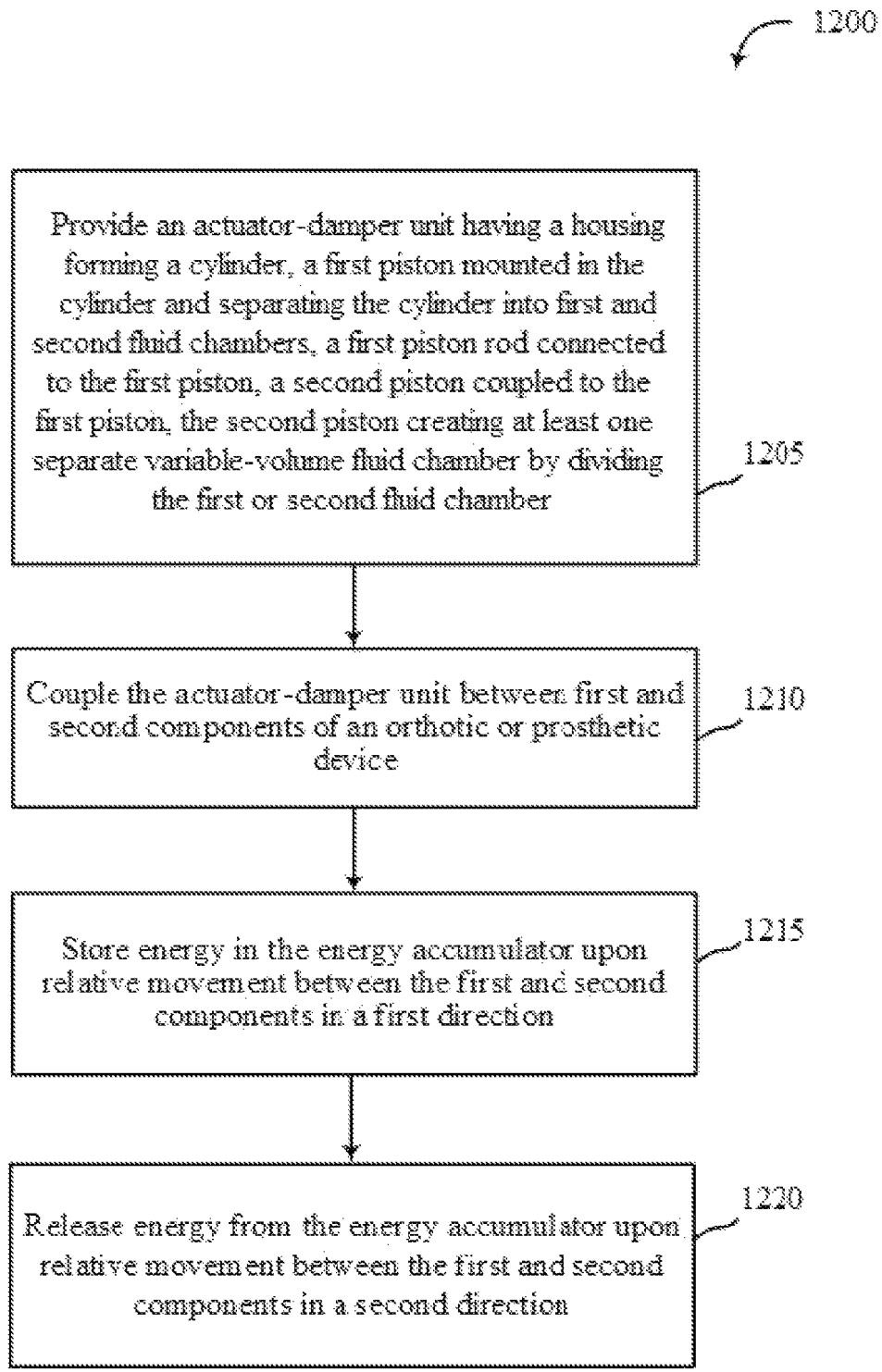
FIG. 41 is a flow diagram illustrate steps of a method in accordance with the present disclosure.

FIG. 41 is a flow chart illustrating an example of a method 1200 for storing and releasing energy using an actuator-damper unit, in accordance with various aspects of the present disclosure. One or more aspects of the method 1200 may be implemented in conjunction with actuator-damper units 100 of FIGS. 1-40, resistance module 1045 depicted in FIG. 40, and/or control panel 1105 shown in FIG. 40. In some examples, a computing device may execute one or more sets of codes to control the functional elements of the computing device or aspects of the actuator-damper units 100, resistance module 1045, and/or control panel 1105 to perform one or more of the functions described below. Additionally or alternatively, the computing device may perform one or more of the functions described below using special-purpose hardware.

At block 1205, method 1200 may include providing an actuator-damper unit having a housing forming a cylinder, a first piston mounted in the cylinder and separating the cylinder into a first fluid chamber and a second fluid chamber a first piston rod coupled to the first piston, the second piston creating at least one separate variable-volume fluid chamber by dividing the first or second fluid chamber. At block 1210, the method 1200 may include coupling the actuator-damper unit between first and second components of an orthotic or prosthetic device. Block 315 may include storing energy in the energy accumulator upon relative movement between the first and second components in a first direction and second components when energy is available due to the user's motion or the activation of an external power source. Method 1200 may also include, at block 1225, releasing energy from the energy accumulator upon relative movement between the first and second components in a second direction when needed to support the user's motion.

In other embodiments, methods according to the present disclosure may include further steps in addition to those shown in FIG. 41. In some embodiments, the methods may include variations of the steps shown in FIG. 41, or few steps than those shown in FIG. 41.

Figure 42:
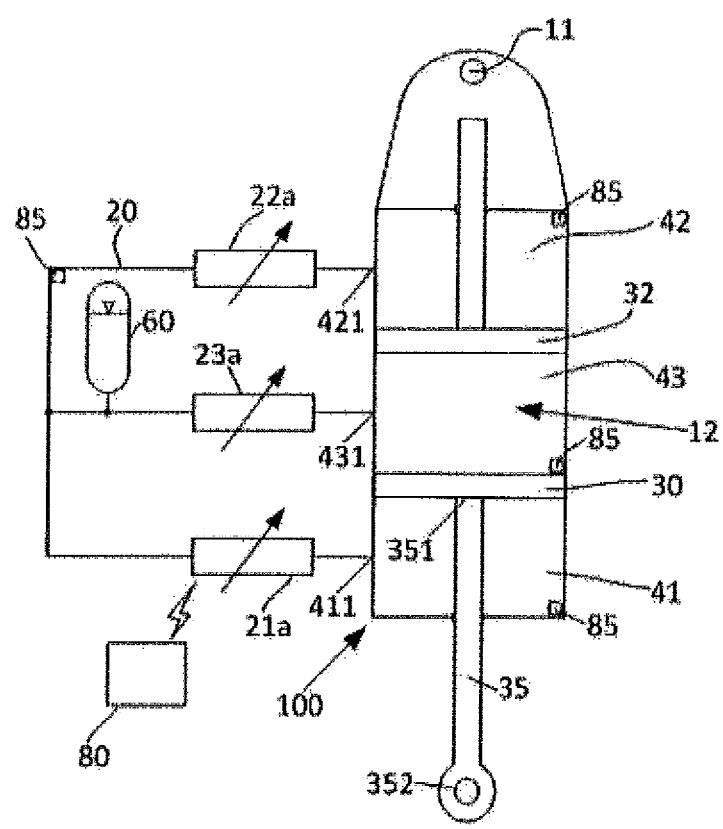
FIG. 42 shows a schematic representation of an exemplary embodiment of an actuator-damper unit with a viscosity change device.

FIG. 42 shows a schematic representation of an exemplary embodiment of an actuator-damper unit comprising appliances or devices 21a, 22a, 23a for changing the viscosity of the hydraulic fluid. In some embodiments, the appliances 21a, 22a, 23a can be electromagnets that generate magnetic fields in the cylinders or along the fluid lines, according to, for example, commands given by a control unit 80 to change the viscosity of a magnetorheological fluid used as a hydraulic fluid. In an alternative embodiment, the devices 21a, 22a, 23a are heating or cooling devices to change the temperature and by this the viscosity of the hydraulic fluid.

The detailed description set forth above in connection with the appended drawings describes examples and does not represent the only instances that may be implemented or that are within the scope of the claims. The terms "example" and "exemplary," when used in this description, mean "serving as an example, instance, or illustration," and not "preferred" or "advantageous over other examples." The detailed description includes specific details for the purpose of providing an understanding of the described techniques. These techniques, however, may be practiced without these specific details. In some instances, known structures and apparatuses are shown in block diagram form in order to avoid obscuring the concepts of the described examples.

Information and signals may be represented using any of a variety of different technologies and techniques. For example, data, instructions, commands, information, signals, bits, symbols, and chips that may be referenced throughout the above description may be represented by voltages, currents, electromagnetic waves, magnetic fields or particles, optical fields or particles, or any combination thereof.

The various illustrative blocks and components described in connection with this disclosure may be implemented or performed with a general-purpose processor, a digital signal processor (DSP), an ASIC, an FPGA or other programmable logic device, discrete gate or transistor logic, discrete hardware components, or any combination thereof designed to perform the functions described herein. A general-purpose processor may be a microprocessor, but in the alternative, the processor may be any conventional processor, controller, microcontroller, and/or state machine. A processor may also be implemented as a combination of computing devices, for example, a combination of a DSP and a microprocessor, multiple microprocessors, one or more microprocessors in conjunction with a DSP core, and/or any combination thereof.

The functions described herein may be implemented in hardware, software executed by a processor, firmware, or any combination thereof. If implemented in software executed by a processor, the functions may be stored on or transmitted over as one or more instructions or code on a computer-readable medium. Other examples and implementations are within the scope and spirit of the disclosure and appended claims. For example, due to the nature of software, functions described above can be implemented using software executed by a processor, hardware, firmware, hardwiring, or combinations of any of these. Features implementing functions may also be physically located at various positions, including being distributed such that portions of functions are implemented at different physical locations.

As used herein, including in the claims, the term "and/or," when used in a list of two or more items, means that any one of the listed items can be employed by itself, or any combination of two or more of the listed items can be employed. For example, if a composition is described as containing components A, B, and/or C, the composition can contain A alone; B alone; C alone; A and B in combination; A and C in combination; B and C in combination; or A, B, and C in combination. Also, as used herein, including in the claims, "or" as used in a list of items (for example, a list of items prefaced by a phrase such as "at least one of" or "one or more of") indicates a disjunctive list such that, for example, a list of "at least one of A, B, or C" means A or B or C or AB or AC or BC or ABC, or A and B and C.

In addition, any disclosure of components contained within other components or separate from other components should be considered exemplary because multiple other architectures may potentially be implemented to achieve the same functionality, including incorporating all, most, and/or some elements as part of one or more unitary structures and/or separate structures.

Computer-readable media includes both computer storage media and communication media including any medium that facilitates transfer of a computer program from one place to another. A storage medium may be any available medium that can be accessed by a general purpose or special purpose computer. By way of example, and not limitation, computer-readable media can comprise RAM, ROM, EEPROM, flash memory, CD-ROM, DVD, or other optical disk storage, magnetic disk storage or other magnetic storage devices, or any other medium that can be used to carry or store desired program code means in the form of instructions or data structures and that can be accessed by a general-purpose or special-purpose computer, or a general-purpose or special-purpose processor. Also, any connection is properly termed a computer-readable medium. For example, if the software is transmitted from a website, server, or other remote source using a coaxial cable, fiber optic cable, twisted pair, digital subscriber line (DSL), or wireless technologies such as infrared, radio, and microwave, or any combination thereof, then the coaxial cable, fiber optic cable, twisted pair, DSL, or wireless technologies such as infrared, radio, and/or microwave are included in the definition of medium. Disk and disc, as used herein, include any combination of compact disc (CD), laser disc, optical disc, digital versatile disc (DVD), floppy disk and Blu-ray disc where disks usually reproduce data magnetically, while discs reproduce data optically with lasers. Combinations of the above are also included within the scope of computer-readable media.

The previous description of the disclosure is provided to enable a person skilled in the art to make or use the disclosure. Various modifications to the disclosure will be readily apparent to those skilled in the art, and the generic principles defined herein may be applied to other variations without departing from the scope of the disclosure. Thus, the disclosure is not to be limited to the examples and designs described herein but is to be accorded the broadest scope consistent with the principles and novel features disclosed.

The process parameters, actions, and steps described and/or illustrated in this disclosure are given by way of example only and can be varied as desired. For example, while the steps illustrated and/or described may be shown or discussed in a particular order, these steps do not necessarily need to be performed in the order illustrated or discussed. The various exemplary methods described and/or illustrated here may also omit one or more of the steps described or illustrated here or include additional steps in addition to those disclosed.

Furthermore, while various embodiments have been described and/or illustrated here in the context of fully functional computing systems, one or more of these exemplary embodiments may be distributed as a program product in a variety of forms, regardless of the particular type of computer-readable media used to actually carry out the distribution. The embodiments disclosed herein may also be implemented using software modules that perform certain tasks. These software modules may include script, batch, or other executable files that may be stored on a computer-readable storage medium or in a computing system. In some embodiments, these software modules may permit and/or instruct a computing system to perform one or more of the exemplary embodiments disclosed here.

This description, for purposes of explanation, has been described with reference to specific embodiments. The illustrative discussions above, however, are not intended to be exhaustive or limit the present systems and methods to the precise forms discussed. Many modifications and variations are possible in view of the above teachings. The embodiments were chosen and described in order to explain the principles of the present systems and methods and their practical applications, to enable others skilled in the art to utilize the present systems, apparatus, and methods and various embodiments with various modifications as may be suited to the particular use contemplated.

We claim:

1. An actuator-damper unit for use between first and second components of an orthotic or prosthetic device, comprising:
   a first housing having a cylinder formed therein and configured to be coupled to the first component of the orthotic or prosthetic device;
   a first piston displaceably mounted in the cylinder, the first piston separating the cylinder into a first fluid chamber of the first piston and a second fluid chamber of the first piston, the first piston and cylinder defining a first piston-cylinder unit;
   a first piston rod coupled to the first piston at a first end, and configured to be coupled at a second end to the second component of the orthotic or prosthetic device;
   a second piston coupled to the first piston, the second piston defining a first fluid chamber of the second piston and a second fluid chamber of the second piston, wherein the second piston is free of mechanical connections to devices external to a second housing of the second piston, and wherein the first and second chambers of the second piston are both fluidly coupled to the first and second fluid chambers of the first piston;
   a compensation volume fluidly coupled to at least one of the first and second fluid chambers of the first piston to compensate for volume changes in the cylinder as the first piston rod move into and out of the cylinder;
   wherein an axial change in position of the first piston in the first cylinder in a first axial direction and in an opposite second axial direction causes a change in position of the second piston to store energy.

2. The actuator-damper unit according to claim 1, wherein the second piston is coupled to the first piston by at least one of an compressible energy accumulator and an expandable energy accumulator.

3. The actuator-damper unit according claim 2, wherein the energy accumulator is one of a spring, an elastomeric element, and a compressible fluid volume.

4. The actuator-damper unit according to claim 1, wherein at least one additional variable-volume fluid chamber is hydraulically coupled to at least one of the fluid chambers defined by the first and second pistons.

5. The actuator-damper unit according to claim 4, wherein the first fluid chamber, the second fluid chamber and the at least one variable-volume fluid chamber each has at least one access opening and is interconnected via fluid lines to at least one of the other fluid chambers.

6. The actuator-damper unit according to claim 1, further comprising at least one valve corresponding to at least one of the fluid chambers, the at least one valve controlling fluid flow into and out of the corresponding fluid chamber.

7. The actuator-damper unit according to claim 6, wherein the at least one valve is designed as one of a switching valve, a control valve, a non-return valve, or a relief valve.

8. The actuator-damper unit according claim 6, further comprising a control device, the control device connected to the at least one valve and operable to actuate a displacement or switching of the at least one valve.

9. The actuator-damper unit according to claim 8, wherein the control device is coupled to at least one sensor of the orthotic or prosthetic device, the at least one sensor operable to transmit state data from the actuator-damper unit or the components of the orthotic or prosthetic device to the control device.

10. The actuator-damper unit according to claim 9, wherein the at least one sensor determines one of a piston position, an applied force, a joint angle, or a pressure.

11. The actuator-damper unit according to claim 1, wherein a rate of fluid flow between two or more of the fluid chambers is controlled at least in part by a viscosity of the fluid.

12. The actuator-damper unit according to claim 1, wherein the at least one compensating volume is coupled to at least one of the fluid chambers though at least one valve.

13. The actuator-damper unit according to claim 1, wherein the at least one compensating volume comprises a pressure accumulator.

14. The actuator-damper unit according to claim 1, further comprising a pump operable to increase fluid pressure in the actuator-damper unit.

15. The actuator-damper unit according to claim 14, wherein the pump is coupled to an energy accumulator.

16. The actuator-damper unit according claim 1, wherein the fluid comprises a hydraulic fluid.

17. The actuator-damper unit according to claim 1, wherein only the second piston and no additional piston is coupled to the first piston.

18. The actuator-damper unit according to claim 17, further comprising a single spring operable to store energy in response to the change in position of the second piston.

19. An actuator-damper unit for use between first and second components of an orthotic or prosthetic device, comprising:
- a first housing having a cylinder formed therein and configured to be coupled to the first component of the orthotic or prosthetic device;
- a first piston displaceably mounted in the cylinder, the first piston separating the cylinder into a first fluid chamber of the first piston and a second fluid chamber of the first piston, the first piston and cylinder defining a first piston-cylinder unit;
- a first piston rod coupled to the first piston at a first end, and configured to be coupled at a second end to the second component of the orthotic or prosthetic device;
- a second piston coupled to the first piston, the second piston defining a first fluid chamber of the second piston and a second fluid chamber of the second piston, wherein the second piston is free of mechanical connections to devices external to a second housing of the second piston, and wherein the first and second chambers of the second piston are both fluidly coupled to the first and second fluid chambers of the first piston;
- a compensation volume fluidly coupled to at least one of the first and second fluid chambers of the first piston to compensate for volume changes in the cylinder as the first piston rod moves into and out of the cylinder;
- wherein an axial change in position of the first piston in the first cylinder in a first axial direction and in an opposite second axial direction causes a change in position of the second piston, and vice versa.

20. The actuator-damper unit according to claim 19, further comprising at least one valve corresponding to at least one of the fluid chambers, the at least one valve controlling fluid flow into and out of the corresponding fluid chamber.

21. The actuator-damper unit according to claim 19, wherein the second piston is coupled to the first piston by at least one of a compressible energy accumulator and an expandable energy accumulator.

22. The actuator-damper unit according claim 21, wherein the energy accumulator is one of a spring, an elastomeric element, and a compressible fluid volume.

23. The actuator-damper unit according claim 21, wherein the at least one of the compressible and the expandable energy accumulator has an impact on the movement of at least one of the first piston and the second piston or the first piston and the second piston act on the at least one of the compressible energy accumulator and the expandable energy accumulator.

24. The actuator-damper unit according to claim 19, further comprising a pump operable to increase fluid pressure in the actuator-damper unit.

25. An actuator-damper unit for use between first and second components of an orthotic or prosthetic device, comprising:
- a first cylinder configured to be coupled to the first component of the orthotic or prosthetic device;
- a first piston displaceably mounted in the first cylinder, the first piston separating the first cylinder into first and second variable fluid chambers, the first cylinder and first piston defining a first piston-cylinder unit;
- a first piston rod coupled to the first piston at a first end, and configured to be coupled at a second end to the second component of the orthotic or prosthetic device;
- a second cylinder;
- a second piston displaceably mounted in the second cylinder, the second piston separating the second cylinder into third and fourth variable fluid chambers, the third and fourth fluid chambers both being in fluid communication with the first and second variable fluid chambers, wherein the second piston is free of mechanical connections to devices external to the second cylinder;
- a compensation volume fluidly coupled to at least one of the first and second fluid chambers to compensate for volume changes in the first cylinder as the first piston rod moves into and out of the first cylinder;
- wherein an axial change in position of the first piston in the first cylinder can cause a change in position of the second piston in the second cylinder.

26. The actuator damper unit according to claim 25, wherein an axial change in position of the first piston in the first cylinder in a first axial direction and in an opposite second axial direction causes a change in position of the second piston to store energy.

* * * * *